(12) United States Patent
Jain et al.

(10) Patent No.: US 11,901,083 B1
(45) Date of Patent: Feb. 13, 2024

(54) USING GENETIC AND PHENOTYPIC DATA SETS FOR DRUG DISCOVERY CLINICAL TRIALS

(71) Applicant: VigNet Incorporated, Fairfax, VA (US)

(72) Inventors: Praduman Jain, Fairfax, VA (US); Josh Schilling, Salem, OR (US); Dave Klein, Oakton, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

(21) Appl. No.: 17/538,457

(22) Filed: Nov. 30, 2021

(51) Int. Cl.
*G16H 50/30* (2018.01)
*G16B 20/00* (2019.01)
*G16H 50/20* (2018.01)

(52) U.S. Cl.
CPC ............. *G16H 50/30* (2018.01); *G16B 20/00* (2019.02); *G16H 50/20* (2018.01)

(58) Field of Classification Search
CPC ......... G16H 50/30; G16H 50/20; G16B 20/00
See application file for complete search history.

(56) References Cited

U.S. PATENT DOCUMENTS

| | | | |
|---|---|---|---|
| 5,545,186 A | 8/1996 | Olson et al. |
| 5,547,878 A | 8/1996 | Kell |
| 6,019,777 A | 2/2000 | Mackenzie |
| 6,029,144 A | 2/2000 | Barrett et al. |
| 6,029,195 A | 2/2000 | Herz |
| 6,039,688 A | 3/2000 | Douglas et al. |
| 6,260,022 B1 | 7/2001 | Brown |
| 6,269,339 B1 | 7/2001 | Silver |
| 6,321,172 B1 | 11/2001 | Jakob et al. |
| 6,514,200 B1 | 2/2003 | Khouri |

(Continued)

FOREIGN PATENT DOCUMENTS

| CN | 106384321 | 2/2017 |
|---|---|---|
| EP | 2851820 | 3/2015 |

(Continued)

OTHER PUBLICATIONS

U.S. Appl. No. 15/803,556, filed Nov. 3, 2017, Jain et al.

(Continued)

*Primary Examiner* — Reginald R Reyes
(74) *Attorney, Agent, or Firm* — Fish & Richardson P.C.

(57) ABSTRACT

Methods, systems, and apparatus, including computer programs encoded on a computer storage medium, for adjusting monitoring profiles of end devices. In one aspect, a method generates a health profile for the user; determines, based on the health profile of the user, a particular health risk for the user; determines, for the particular health risk, a first monitoring profile for the user that causes one or more health monitoring devices to monitor the user for a first set of health data; provides the first monitoring profile to the one or more health monitoring devices; receives epigenetic data describing epigenetic factors for the user; determines that a health change event for the particular health risk has occurred for the user; and in response, determines a second monitoring profile for the user for the particular health risk and provides the second monitoring profile to the one or more health monitoring devices.

24 Claims, 11 Drawing Sheets

(56) References Cited

U.S. PATENT DOCUMENTS

| | | |
|---|---|---|
| 6,663,846 B1 | 12/2003 | McCombs et al. |
| 6,828,992 B1 | 12/2004 | Freeman |
| 6,879,970 B2 | 4/2005 | Shiffman et al. |
| 6,904,408 B1 | 6/2005 | McCarthy |
| 7,054,782 B2 | 5/2006 | Hartlaub |
| 7,076,534 B1 | 7/2006 | Cleron et al. |
| 7,086,007 B1 | 8/2006 | Bushey |
| 7,170,993 B2 | 1/2007 | Anderson et al. |
| 7,213,009 B2 | 5/2007 | Pstotnik et al. |
| 7,251,609 B1 | 7/2007 | McAlindon et al. |
| 7,330,717 B2 | 2/2008 | Gidron et al. |
| 7,415,447 B2 | 8/2008 | Shiffman et al. |
| 7,447,643 B1 | 11/2008 | Olson et al. |
| 7,730,063 B2 | 6/2010 | Eder |
| 7,752,059 B2 | 7/2010 | Sweeney et al. |
| 7,809,802 B2 | 10/2010 | Lerman et al. |
| 7,827,478 B2 | 11/2010 | Farr et al. |
| 7,827,495 B2 | 11/2010 | Bells et al. |
| 7,853,455 B2 | 12/2010 | Brown |
| 7,907,769 B2 | 3/2011 | Sammak et al. |
| 7,917,438 B2 | 3/2011 | Kenedy et al. |
| 7,953,613 B2 | 5/2011 | Gizewski |
| 8,056,100 B2 | 11/2011 | Herz et al. |
| 8,065,180 B2 | 11/2011 | Hufford et al. |
| 8,078,956 B1 | 12/2011 | Feldman |
| 8,180,688 B1 | 5/2012 | Velummylum et al. |
| 8,347,263 B1 | 1/2013 | Offer |
| 8,380,531 B2 | 2/2013 | Paty et al. |
| 8,433,605 B2 | 4/2013 | Hufford et al. |
| 8,533,029 B2 | 9/2013 | Hufford et al. |
| 8,583,453 B2 | 11/2013 | Plummer et al. |
| 8,589,175 B2 | 11/2013 | Glauser et al. |
| 8,655,915 B2 | 2/2014 | Kenedy et al. |
| 8,667,487 B1 | 3/2014 | Boodman et al. |
| 8,684,922 B2 | 4/2014 | Tran |
| 8,706,521 B2 | 4/2014 | Ramarajan et al. |
| 8,707,392 B2 | 4/2014 | Birtwhistle et al. |
| 8,775,415 B2 | 7/2014 | Jeon et al. |
| 8,799,666 B2 | 8/2014 | Kesanupalli et al. |
| 8,805,759 B1 | 8/2014 | Cha et al. |
| 8,825,775 B2 | 9/2014 | Bohner et al. |
| 8,850,304 B2 | 9/2014 | Ye et al. |
| 8,862,410 B2 | 10/2014 | Hatchwell et al. |
| 8,978,106 B2 | 3/2015 | Swamy et al. |
| 8,990,250 B1 | 3/2015 | Chowdry et al. |
| 8,997,038 B2 | 3/2015 | Becker |
| 9,134,964 B2 | 9/2015 | Hirsch |
| 9,135,445 B2 | 9/2015 | Kay et al. |
| 9,170,800 B2 | 10/2015 | Lang |
| 9,183,365 B2 | 11/2015 | Taveau et al. |
| 9,256,698 B2 | 2/2016 | Vincent, III |
| 9,286,442 B2 | 3/2016 | Csoma et al. |
| 9,361,011 B1 | 6/2016 | Burns |
| 9,426,433 B1 | 8/2016 | Mazzarella |
| 9,461,972 B1 | 10/2016 | Mehta |
| 9,514,655 B1 | 12/2016 | Nusbaum et al. |
| 9,542,649 B2 | 1/2017 | Su |
| 9,582,529 B2 | 2/2017 | Bruestle |
| 9,715,370 B2 | 7/2017 | Friedman |
| 9,753,618 B1 | 9/2017 | Jain |
| 9,760,343 B2 | 9/2017 | Noens et al. |
| 9,767,230 B2 | 9/2017 | Kimchi et al. |
| 9,773,308 B2 | 9/2017 | Silbersweig et al. |
| 9,824,606 B2 | 11/2017 | Basson et al. |
| 9,844,725 B1 | 12/2017 | Durkin et al. |
| 9,848,061 B1 | 12/2017 | Jain et al. |
| 9,858,063 B2 | 1/2018 | Jain et al. |
| 9,928,230 B1 | 3/2018 | Jain et al. |
| 9,940,454 B2 | 4/2018 | Richardson et al. |
| 9,942,358 B2 | 4/2018 | Babu et al. |
| 9,983,775 B2 | 5/2018 | Jain et al. |
| 10,002,199 B2 | 6/2018 | Matamala et al. |
| 10,068,270 B1 | 9/2018 | Kay et al. |
| 10,068,422 B2 | 9/2018 | Gadher et al. |
| 10,069,934 B2 | 9/2018 | Jain et al. |
| 10,095,688 B1 | 10/2018 | Jain et al. |
| 10,152,761 B2 | 12/2018 | Kress et al. |
| 10,202,769 B2 | 2/2019 | Gya |
| 10,205,769 B2 | 2/2019 | Sehgal |
| 10,231,622 B2 | 3/2019 | Soyao et al. |
| 10,248,401 B1 | 4/2019 | Chen et al. |
| 10,249,389 B2 | 4/2019 | Athey et al. |
| 10,304,000 B2 | 5/2019 | Birnbaum et al. |
| 10,311,478 B2 | 6/2019 | Dai et al. |
| 10,452,816 B2 | 10/2019 | Kidd et al. |
| 10,482,135 B2 | 11/2019 | Rychikhin |
| 10,521,557 B2 | 12/2019 | Jain et al. |
| 10,546,339 B2 | 1/2020 | Jiao et al. |
| 10,559,048 B2 | 2/2020 | Giusti et al. |
| 10,565,894 B1 | 2/2020 | Jain et al. |
| 10,580,531 B2 | 3/2020 | Jiao et al. |
| 10,636,525 B2 | 4/2020 | Jiao et al. |
| 10,650,474 B2 | 5/2020 | Jiao et al. |
| 10,672,519 B2 | 6/2020 | Jiao et al. |
| 10,705,816 B2 | 7/2020 | Jain et al. |
| 10,726,945 B2 | 7/2020 | Sanborn et al. |
| 10,733,116 B2 | 8/2020 | Litichever et al. |
| 10,733,266 B2 | 8/2020 | Whitehurst |
| 10,756,957 B2 | 8/2020 | Jain et al. |
| 10,762,990 B1 | 9/2020 | Jain et al. |
| 10,775,974 B2 | 9/2020 | Schilling et al. |
| 10,938,651 B2 | 3/2021 | Jain et al. |
| 10,991,448 B2 | 4/2021 | Vaske et al. |
| 10,998,101 B1 | 5/2021 | Tran et al. |
| 11,056,242 B1 | 7/2021 | Jain et al. |
| 11,061,798 B1 | 7/2021 | Jain et al. |
| 11,069,431 B2 | 7/2021 | Giusti et al. |
| 11,082,487 B1 | 8/2021 | Jain et al. |
| 11,102,304 B1 | 8/2021 | Jain et al. |
| 11,145,416 B1 * | 10/2021 | Hafez .................. G16H 50/30 |
| 2001/0019338 A1 | 9/2001 | Roth |
| 2002/0010596 A1 | 1/2002 | Matory |
| 2002/0022973 A1 | 2/2002 | Sun |
| 2002/0099570 A1 | 7/2002 | Knight |
| 2002/0143595 A1 | 10/2002 | Frank et al. |
| 2002/0157091 A1 | 10/2002 | DeMello et al. |
| 2003/0065669 A1 | 4/2003 | Kahn et al. |
| 2003/0078960 A1 | 4/2003 | Murren et al. |
| 2003/0130871 A1 | 7/2003 | Rao et al. |
| 2003/0165954 A1 | 9/2003 | Katagiri et al. |
| 2003/0182429 A1 | 9/2003 | Jagels |
| 2003/0229522 A1 | 12/2003 | Thompson et al. |
| 2004/0030424 A1 | 2/2004 | Corl |
| 2004/0073868 A1 | 4/2004 | Easter et al. |
| 2004/0122715 A1 | 6/2004 | McAuliffe |
| 2004/0172447 A1 | 9/2004 | Miller |
| 2004/0203755 A1 | 10/2004 | Brunet et al. |
| 2004/0210457 A1 | 10/2004 | Sameh |
| 2004/0216054 A1 | 10/2004 | Matthews |
| 2005/0050320 A1 | 3/2005 | Wassmann et al. |
| 2005/0055687 A1 | 3/2005 | Mayer |
| 2005/0086587 A1 | 4/2005 | Balz |
| 2005/0144072 A1 | 6/2005 | Perkowski et al. |
| 2005/0165626 A1 | 7/2005 | Karpf |
| 2005/0186550 A1 | 8/2005 | Gillani |
| 2005/0246304 A1 | 11/2005 | Knight et al. |
| 2006/0004603 A1 | 1/2006 | Peterka et al. |
| 2006/0041452 A1 | 2/2006 | Kukarni |
| 2006/0107219 A1 | 5/2006 | Ahya |
| 2006/0184493 A1 | 8/2006 | Shiffman et al. |
| 2006/0205564 A1 | 9/2006 | Peterson |
| 2006/0206861 A1 | 9/2006 | Shenfield |
| 2006/0282516 A1 | 12/2006 | Taylor |
| 2007/0021984 A1 | 1/2007 | Brown |
| 2007/0072156 A1 | 3/2007 | Kaufman et al. |
| 2007/0136093 A1 | 6/2007 | Rankin et al. |
| 2007/0172844 A1 | 7/2007 | Lancaster et al. |
| 2007/0179361 A1 | 8/2007 | Brown et al. |
| 2007/0231828 A1 | 10/2007 | Beachy et al. |
| 2007/0250429 A1 | 10/2007 | Walser et al. |
| 2007/0259351 A1 | 11/2007 | Chinitz et al. |
| 2007/0276270 A1 | 11/2007 | Tran |
| 2007/0281285 A1 | 12/2007 | Jayaweera |
| 2008/0005679 A1 | 1/2008 | Rimas-Ribikauskas |

(56) References Cited

U.S. PATENT DOCUMENTS

| | | |
|---|---|---|
| 2008/0010254 A1 | 1/2008 | Settimi |
| 2008/0021287 A1 | 1/2008 | Woellenstein et al. |
| 2008/0034314 A1 | 2/2008 | Louch et al. |
| 2008/0126110 A1 | 5/2008 | Haeberle |
| 2008/0127040 A1 | 5/2008 | Barcellona |
| 2008/0140444 A1 | 6/2008 | Karkanias |
| 2008/0177638 A1 | 7/2008 | Butler |
| 2008/0201174 A1 | 8/2008 | Ramsubramanian |
| 2008/0242221 A1 | 10/2008 | Shapiro et al. |
| 2008/0243038 A1 | 10/2008 | Bennett |
| 2008/0254429 A1 | 10/2008 | Woolf et al. |
| 2008/0261191 A1 | 10/2008 | Woolf et al. |
| 2008/0301118 A1 | 12/2008 | Chien |
| 2008/0311968 A1 | 12/2008 | Hunter |
| 2009/0023555 A1 | 1/2009 | Raymond |
| 2009/0024944 A1 | 1/2009 | Louch |
| 2009/0031215 A1 | 1/2009 | Collier |
| 2009/0035733 A1 | 2/2009 | Meitar |
| 2009/0043689 A1 | 2/2009 | Yang |
| 2009/0076856 A1 | 3/2009 | Darby et al. |
| 2009/0094052 A1 | 4/2009 | James et al. |
| 2009/0119678 A1 | 5/2009 | Shih |
| 2009/0125333 A1 | 5/2009 | Heywood |
| 2009/0150814 A1 | 6/2009 | Eyer |
| 2009/0156190 A1 | 6/2009 | Fisher |
| 2009/0163182 A1 | 6/2009 | Gatti |
| 2009/0170715 A1 | 7/2009 | Glinsky |
| 2009/0172002 A1 | 7/2009 | Bathiche |
| 2009/0248883 A1 | 10/2009 | Suryanarayana et al. |
| 2009/0276771 A1 | 11/2009 | Nickolov et al. |
| 2010/0036681 A1 | 2/2010 | Naik et al. |
| 2010/0041378 A1 | 2/2010 | Aceves |
| 2010/0082367 A1 | 4/2010 | Hains et al. |
| 2010/0088245 A1 | 4/2010 | Harrison et al. |
| 2010/0122286 A1 | 5/2010 | Begeja |
| 2010/0131482 A1 | 5/2010 | Linthicum |
| 2010/0179833 A1 | 7/2010 | Roizen et al. |
| 2010/0211941 A1 | 8/2010 | Roseborough |
| 2010/0218132 A1 | 8/2010 | Soni et al. |
| 2010/0250258 A1 | 9/2010 | Smithers et al. |
| 2010/0250341 A1 | 9/2010 | Hauser |
| 2010/0262664 A1 | 10/2010 | Brown et al. |
| 2010/0333037 A1 | 12/2010 | Pavlovski |
| 2011/0066934 A1 | 3/2011 | Treisman |
| 2011/0126119 A1 | 5/2011 | Young |
| 2011/0145747 A1 | 6/2011 | Wong et al. |
| 2011/0173308 A1 | 7/2011 | Gutekunst |
| 2011/0184748 A1 | 7/2011 | Fierro et al. |
| 2011/0200979 A1 | 8/2011 | Benson |
| 2011/0230360 A1 | 9/2011 | Stephan et al. |
| 2011/0273309 A1 | 11/2011 | Zhang et al. |
| 2011/0288900 A1 | 11/2011 | McQueen et al. |
| 2012/0035954 A1 | 2/2012 | Yeskel |
| 2012/0036220 A1 | 2/2012 | Dare et al. |
| 2012/0047029 A1 | 2/2012 | Veres et al. |
| 2012/0072232 A1 | 3/2012 | Frankham et al. |
| 2012/0084399 A1 | 4/2012 | Scharber et al. |
| 2012/0102050 A1 | 4/2012 | Button |
| 2012/0143694 A1 | 6/2012 | Zargahi |
| 2012/0143697 A1 | 6/2012 | Chopra |
| 2012/0215639 A1 | 8/2012 | Ramer et al. |
| 2012/0220835 A1 | 8/2012 | Chung |
| 2012/0260294 A1 | 10/2012 | Reichardt et al. |
| 2012/0266251 A1 | 10/2012 | Birtwhistle et al. |
| 2012/0272156 A1 | 10/2012 | Kerger |
| 2013/0060922 A1 | 3/2013 | Koponen et al. |
| 2013/0085744 A1 | 4/2013 | Arias |
| 2013/0103749 A1 | 4/2013 | Werth et al. |
| 2013/0110565 A1 | 5/2013 | Means |
| 2013/0145024 A1 | 6/2013 | Cao |
| 2013/0145457 A1 | 6/2013 | Papkipos et al. |
| 2013/0166494 A1 | 6/2013 | Davis |
| 2013/0172774 A1 | 7/2013 | Crowder |
| 2013/0179472 A1 | 7/2013 | Junqua |
| 2013/0212487 A1 | 8/2013 | Cote |
| 2013/0238686 A1 | 9/2013 | O'Donoghue |
| 2013/0283188 A1 | 10/2013 | Sanghvi |
| 2013/0326375 A1 | 12/2013 | Barak et al. |
| 2013/0329632 A1 | 12/2013 | Buyukkoc et al. |
| 2014/0017648 A1 | 1/2014 | Williams et al. |
| 2014/0019191 A1 | 1/2014 | Mulji |
| 2014/0019480 A1 | 1/2014 | Rychikhin |
| 2014/0026113 A1 | 1/2014 | Farooqi |
| 2014/0033171 A1 | 1/2014 | Lorenz |
| 2014/0052681 A1 | 2/2014 | Nitz et al. |
| 2014/0058755 A1 | 2/2014 | Macoviak et al. |
| 2014/0088995 A1 | 3/2014 | Damani |
| 2014/0100883 A1 | 4/2014 | Hamilton |
| 2014/0101628 A1 | 4/2014 | Almog |
| 2014/0109072 A1 | 4/2014 | Lang et al. |
| 2014/0109115 A1 | 4/2014 | Low |
| 2014/0109177 A1 | 4/2014 | Barton et al. |
| 2014/0156645 A1 | 6/2014 | Brust |
| 2014/0156823 A1 | 6/2014 | Liu |
| 2014/0157171 A1 | 6/2014 | Brust et al. |
| 2014/0173405 A1 | 6/2014 | Ferrara |
| 2014/0181715 A1 | 6/2014 | Axelrod |
| 2014/0187228 A1 | 7/2014 | Fisher |
| 2014/0240122 A1 | 8/2014 | Roberts |
| 2014/0257058 A1 | 9/2014 | Clarysse et al. |
| 2014/0257852 A1 | 9/2014 | Walker et al. |
| 2014/0258827 A1 | 9/2014 | Gormish |
| 2014/0273913 A1 | 9/2014 | Michel |
| 2014/0278474 A1 | 9/2014 | McClure et al. |
| 2014/0278536 A1 | 9/2014 | Zhang |
| 2014/0282061 A1 | 9/2014 | Wheatley et al. |
| 2014/0288955 A1 | 9/2014 | Zhou et al. |
| 2014/0297311 A1* | 10/2014 | Jackson ............ G06Q 30/0201 705/2 |
| 2014/0309868 A1 | 10/2014 | Ricci |
| 2014/0317595 A1 | 10/2014 | Kilby |
| 2014/0344208 A1 | 11/2014 | Ghasemzadeh et al. |
| 2014/0344397 A1 | 11/2014 | Kostof |
| 2014/0358482 A1 | 12/2014 | Sehgal |
| 2014/0365961 A1 | 12/2014 | Lefor et al. |
| 2015/0006214 A1 | 1/2015 | Lavoie et al. |
| 2015/0012301 A1 | 1/2015 | Weschler et al. |
| 2015/0019342 A1 | 1/2015 | Gupta |
| 2015/0025917 A1 | 1/2015 | Stempora |
| 2015/0025997 A1 | 1/2015 | Tilenius et al. |
| 2015/0056589 A1 | 2/2015 | Zhang et al. |
| 2015/0074635 A1 | 3/2015 | Margiotta |
| 2015/0088955 A1 | 3/2015 | Hendrick et al. |
| 2015/0089224 A1 | 3/2015 | Beckman |
| 2015/0106449 A1 | 4/2015 | Cherry |
| 2015/0135160 A1 | 5/2015 | Gauvin |
| 2015/0143470 A1 | 5/2015 | Stiekes et al. |
| 2015/0148061 A1 | 5/2015 | Koukoumidis |
| 2015/0154002 A1 | 6/2015 | Weinstein et al. |
| 2015/0163121 A1 | 6/2015 | Mahaffey |
| 2015/0178473 A1 | 6/2015 | Hufford et al. |
| 2015/0178474 A1 | 6/2015 | Hufford et al. |
| 2015/0199490 A1 | 7/2015 | Iancu et al. |
| 2015/0212714 A1 | 7/2015 | Hua |
| 2015/0220233 A1 | 8/2015 | Kok et al. |
| 2015/0248473 A1 | 9/2015 | Kenedy et al. |
| 2015/0286802 A1 | 10/2015 | Kansara |
| 2015/0294090 A1 | 10/2015 | Kodiyan |
| 2015/0347088 A1 | 12/2015 | Bruestle |
| 2015/0356701 A1 | 12/2015 | Gandy |
| 2016/0048652 A1 | 2/2016 | Spivey |
| 2016/0058287 A1 | 3/2016 | Dyell |
| 2016/0085754 A1 | 3/2016 | Gifford et al. |
| 2016/0085909 A1 | 3/2016 | Reese et al. |
| 2016/0086505 A1 | 3/2016 | Hanlon |
| 2016/0092339 A1 | 3/2016 | Straub |
| 2016/0092631 A1 | 3/2016 | Yandell et al. |
| 2016/0124930 A1 | 5/2016 | Dhawan |
| 2016/0140320 A1 | 5/2016 | Moturu et al. |
| 2016/0189317 A1 | 6/2016 | Papandrea |
| 2016/0196389 A1 | 7/2016 | Moturu et al. |
| 2016/0203663 A1 | 7/2016 | Proctor |
| 2016/0217118 A1 | 7/2016 | Singh |
| 2016/0234624 A1 | 8/2016 | Riva et al. |

(56) References Cited

U.S. PATENT DOCUMENTS

| | | |
|---|---|---|
| 2016/0300570 A1 | 10/2016 | Gustafson et al. |
| 2016/0312287 A1 | 10/2016 | Cottrell et al. |
| 2016/0357794 A1 | 12/2016 | Liang et al. |
| 2016/0357944 A1 | 12/2016 | Iyer et al. |
| 2017/0000422 A1 | 1/2017 | Moturu et al. |
| 2017/0004260 A1 | 1/2017 | Moturu et al. |
| 2017/0011200 A1 | 1/2017 | Arshad et al. |
| 2017/0020444 A1 | 1/2017 | Lurie |
| 2017/0024546 A1 | 1/2017 | Schmidt |
| 2017/0039324 A1 | 2/2017 | Francois et al. |
| 2017/0048215 A1 | 2/2017 | Straub |
| 2017/0097743 A1 | 4/2017 | Hameed et al. |
| 2017/0116379 A1 | 4/2017 | Scott et al. |
| 2017/0124276 A1 | 5/2017 | Tee |
| 2017/0132395 A1 | 5/2017 | Futch |
| 2017/0169343 A1 | 6/2017 | Kirkham et al. |
| 2017/0118159 A1 | 7/2017 | Ratiu et al. |
| 2017/0213007 A1 | 7/2017 | Moturu et al. |
| 2017/0228229 A1 | 8/2017 | Jain et al. |
| 2017/0231528 A1 | 8/2017 | Nathan |
| 2017/0235912 A1 | 8/2017 | Moturu et al. |
| 2017/0262606 A1 | 9/2017 | Abdullah |
| 2017/0286389 A1 | 10/2017 | Ceneviva |
| 2017/0303187 A1 | 10/2017 | Crouthamel et al. |
| 2017/0308669 A1 | 10/2017 | Apte et al. |
| 2017/0308680 A1 | 10/2017 | Efros et al. |
| 2017/0323064 A1 | 11/2017 | Bates |
| 2017/0329483 A1 | 11/2017 | Jann et al. |
| 2017/0329500 A1 | 11/2017 | Grammatikakis et al. |
| 2017/0330297 A1 | 11/2017 | Cronin et al. |
| 2017/0344895 A1 | 11/2017 | Roy |
| 2017/0374178 A1 | 12/2017 | Sharma et al. |
| 2018/0001184 A1 | 1/2018 | Tran et al. |
| 2018/0025125 A1 | 1/2018 | Crane et al. |
| 2018/0046780 A1 | 2/2018 | Graiver et al. |
| 2018/0052971 A1 | 2/2018 | Hanina |
| 2018/0068083 A1 | 3/2018 | Cohen et al. |
| 2018/0089159 A1 | 3/2018 | Jain et al. |
| 2018/0090229 A1 | 3/2018 | Sanyal |
| 2018/0096740 A1 | 4/2018 | Moturu et al. |
| 2018/0114596 A1 | 4/2018 | Churchwell et al. |
| 2018/0121187 A1 | 5/2018 | Jain et al. |
| 2018/0122509 A1 | 5/2018 | Christiansson |
| 2018/0144100 A1 | 5/2018 | Chalas et al. |
| 2018/0150523 A1 | 5/2018 | Shiffman et al. |
| 2018/0176331 A1 | 6/2018 | Jain et al. |
| 2018/0197624 A1 | 7/2018 | Robaina et al. |
| 2018/0206775 A1 | 7/2018 | Saria et al. |
| 2018/0210870 A1 | 7/2018 | Jain et al. |
| 2018/0286509 A1 | 10/2018 | Shah |
| 2018/0308569 A1 | 10/2018 | Luellen |
| 2018/0335939 A1 | 11/2018 | Karunamuni |
| 2018/0365028 A1 | 12/2018 | Hosabettu |
| 2018/0365316 A1 | 12/2018 | Liang et al. |
| 2019/0002982 A1 | 1/2019 | Wang |
| 2019/0019581 A1 | 1/2019 | Vaughan et al. |
| 2019/0026663 A1 | 1/2019 | Homeyer et al. |
| 2019/0043501 A1 | 2/2019 | Ramaci |
| 2019/0043610 A1 | 2/2019 | Vaughan |
| 2019/0043619 A1 | 2/2019 | Vaughan et al. |
| 2019/0068753 A1 | 2/2019 | Jain et al. |
| 2019/0074080 A1 | 3/2019 | Appelbaum et al. |
| 2019/0102670 A1 | 4/2019 | Ceulemans |
| 2019/0122266 A1 | 4/2019 | Ramer et al. |
| 2019/0140892 A1 | 5/2019 | Jain et al. |
| 2019/0147043 A1 | 5/2019 | Moskowitz |
| 2019/0172588 A1 | 6/2019 | Tran et al. |
| 2019/0180862 A1 | 6/2019 | Wisser et al. |
| 2019/0201123 A1 | 7/2019 | Shelton |
| 2019/0207814 A1 | 7/2019 | Jain |
| 2019/0214116 A1 | 7/2019 | Eberting |
| 2019/0243944 A1 | 8/2019 | Jain et al. |
| 2019/0286086 A1 | 9/2019 | Gardner et al. |
| 2019/0306093 A1 | 10/2019 | Schilling et al. |
| 2019/0313934 A1 | 10/2019 | Lee et al. |
| 2019/0320310 A1 | 10/2019 | Horelik et al. |
| 2019/0361579 A1 | 11/2019 | Srivastava |
| 2020/0019995 A1 | 1/2020 | Krishnan et al. |
| 2020/0035341 A1 | 1/2020 | Kain et al. |
| 2020/0050330 A1 | 2/2020 | Schilling et al. |
| 2020/0077942 A1 | 3/2020 | Youngblood |
| 2020/0082918 A1 | 3/2020 | Simhon |
| 2020/0112479 A1 | 4/2020 | Jain et al. |
| 2020/0119986 A1 | 4/2020 | Jain et al. |
| 2020/0131581 A1 | 4/2020 | Jain et al. |
| 2020/0135331 A1 | 4/2020 | Mohebbi |
| 2020/0203012 A1 | 6/2020 | Kamath et al. |
| 2020/0227135 A1 | 7/2020 | Yandell et al. |
| 2020/0227152 A1 | 7/2020 | Moturu et al. |
| 2020/0241859 A1 | 7/2020 | Jain et al. |
| 2020/0241860 A1 | 7/2020 | Jain et al. |
| 2020/0242557 A1 | 7/2020 | Carey et al. |
| 2020/0243167 A1 | 7/2020 | Will et al. |
| 2020/0250508 A1 | 8/2020 | De Magalhaes |
| 2020/0267110 A1 | 8/2020 | Nolan et al. |
| 2020/0278852 A1 | 9/2020 | Jain et al. |
| 2020/0279622 A1 | 9/2020 | Heywood et al. |
| 2020/0303074 A1 | 9/2020 | Mueller-Wolf |
| 2020/0336450 A1 | 10/2020 | Gao et al. |
| 2020/0348919 A1 | 11/2020 | Jain |
| 2020/0356353 A1 | 11/2020 | Jain |
| 2020/0407778 A1 | 12/2020 | Locke et al. |
| 2021/0026615 A1 | 1/2021 | Jain |
| 2021/0057091 A1 | 2/2021 | Gutekunst et al. |
| 2021/0058490 A1 | 2/2021 | Jain |
| 2021/0090694 A1* | 3/2021 | Colley ............... G16H 50/70 |
| 2021/0144058 A1 | 5/2021 | Jain |
| 2021/0375412 A1 | 12/2021 | Giusti et al. |
| 2022/0093224 A1* | 3/2022 | Rigby ............... G16H 10/40 |

FOREIGN PATENT DOCUMENTS

| | | |
|---|---|---|
| EP | 2545468 | 1/2016 |
| WO | WO1995012812 | 5/1995 |
| WO | WO2011112556 | 9/2011 |
| WO | WO2012078753 | 6/2012 |
| WO | WO2013144769 | 10/2013 |
| WO | WO2016161416 | 10/2016 |
| WO | WO2017106770 | 6/2017 |

OTHER PUBLICATIONS

[No Author Listed] "Cancer Care Patient Navigation. A practical guide for community cancer centers," Association of Community Cancer Centers, 2009, [retrieved on Jan. 2, 2018], retrieved from: URL <https://www.accc-cancer.org/resources/pdf/Patient-Navigation-Guide.pdf>, 40 pages.

[No Author Listed] "Digital therapeutics," Wikipedia, Nov. 20, 2017, [retrievedon Jan. 2, 2018], retrieved from: URL <https://en.wikipedia.org/wiki/Digital_therapeutics>, 4 pages.

[No Author] "Methods for JITAIs Just in Time Adaptive Intervention," Nov. 9, 2016, retrieved on Nov. 9, 2016, retrieved from URL<https://community.isr.umich.edu/public/Default.aspx?alias=community.isr.umich.edu/public/jitai&>, 1 page.

[No Author], "KhanAcademic.org," retrieved on May 12, 2017, retrieved from URL<http://www.khanacademic.org>, 1 page.

Airwatch: "AirWatch Enterprise Mobility Management Demo," YouTube, Jul. 22, 2014, retrieved on May 3, 2017, retrieved from URL <https://www.youtube.com/watch?v=ucV1n4-tgk>, 1 page.

Airwatch: "Airwatch Laptop Management Demo," YouTube, Oct. 3, 2014, retrieved on May 3, 2017, retrieved from URL<https://www.youtube.com/watch?v=3gHfmdVZECM>, 1 page.

alphr.com [online], "How to Write a Chrome Extension", published on Nov. 22, 2010, retrieved on Oct. 18, 2021, retrieved from URL<https://www.alphr.com/tutorials/363031/how-to-write-a-chrome-extension/>, 12 pages.

Boulos et al., "How smartphones are changing the face of mobile and participatory healthcare: An overview, with example from eCAALYX", Biomedical Engineering Online, Dec. 2011, 10(10:24.

(56) References Cited

OTHER PUBLICATIONS

Braun et al., "Cancer Patient Navigator Tasks across the Cancer Care Continuum," J Health Care Poor Underserved, Feb. 1, 2012, 23(1):398-413.

Cazaly et al., "Making Sense of the Epigenome Using Data Integration Approaches", Frontiers in Pharmacology, Feb. 19, 2019, 15 pages.

CDC.gov [online], "Precision Medicine", published on Aug. 14, 2020, retrieved on Jan. 3, 2022, retrieved from URL<https://www.cdc.gov/genomics/about/precision_med.htm>, 4 pages.

CDC.gov [online], "What is Epigenetics", published on Aug. 3, 2020, retrieved on Jan. 3, 2022, retrieved from URL<https://www.cdc.gov/genomics/disease/epigenetics.htm>, 3 pages.

Conner, "Experience Sampling and Ecological Momentary Assessment with Mobile Phones," 2015, retrieved on May 3, 2017, retrieved from URL<http://www.otago.ac.nz/psychology/otago047475.pdf>, 4 pages.

Disgenet.org [online], "DisGeNET", published on or before Nov. 29, 2021, retrieved on Jan. 3, 2022, retrieved from URL<https://www.disgenet.org/>, 10 pages.

ditoweb.com [online], "What is the Google Chrome Web Store?", published in Aug. 2012, retrieved on Oct. 18, 2021, retrieved from URL<https://www.ditoweb.com/2012/08/what-is-google-chrome-web-store/>, 8 pages.

edsurge.com [online], "Extensions, Add-Ons and Apps, Oh My! How to Utilize Google in Your Classroom", published on Oct. 13, 2014, retrieved on Oct. 18, 2021, retrieved from URL<https://www.edsurge.com/news/2014-10-13-extensions-add-ons-and-apps-oh-my-how-to-utilize-google-in-your-classroom>, 5 pages.

En.Wikipedia.org [online], "Comparative Toxicogenomics Database", published on Dec. 21, 2021, retrieved on Jan. 3, 2022, retrieved from URL<https://en.wikipedia.org/wiki/Comparative_Toxicogenomics_Database>, 4 pages.

En.Wikipedia.org [online], "DisGeNET", published on Jan. 1, 2022, retrieved on Jan. 3, 2022, retrieved from URL<https://en.wikipedia.org/wiki/DisGeNET>, 4 pages.

En.Wikipedia.org [online], "Epigenetic Therapy", published on Oct. 17, 2021, retrieved on Jan. 3, 2022, retrieved from URL<https://en.wikipedia.org/wiki/Epigenetic_therapy>, 7 pages.

En.Wikipedia.org [online], "Epigenetics", published on Dec. 23, 2021, retrieved on Jan. 3, 2022, retrieved from URL<https://en.wikipedia.org/wiki/Epigenetics>, 37 pages.

En.Wikipedia.org [online], "Gene Disease Database", published on Nov. 4, 2021, retrieved on Jan. 3, 2022, retrieved from URL<https://en.wikipedia.org/wiki/Gene_Disease_Database>, 16 pages.

EP Search Report in European Appln. No. 17706938.2, dated Nov. 6, 2019, 7 pages.

Epigenie.com [online], "Epigenetic Tools and Databases", published on or before Nov. 29, 2021, retrieved on Jan. 3, 2022, retrieved from URL<https://epigenie.com/epigenetic-tools-and-databases/>, 9 pages.

Farr, "Can "Digital Therapeutics" Be as Good as Drugs?," MIT Technology Review, Apr. 7, 2017, [retrieved on Jan. 2, 2018], retrieved from: URL <https://www.technologyreview.com/s/604053/can-digital-therapeutics-be-as-good-as-drugs/>, 8 pages.

ghacks.net [online], "The Best Way to Find New Extensions on the Chrome Web Store", published on May 12, 2014, retrieved on Oct. 18, 2021, retrieved from URL<https://www.ghacks.net/2014/05/12/best-way-find-new-extensions-chrome-web-store/>, 6 pages.

Goldsack et al., "Verification, analytical validation and clinical validation (V3): the foundation of determining fit-for-purpose for Biometric Monitoring Technologies (BioMeTs)", NPJ Digital Medicine, Apr. 14, 2020, 3(55):1-15.

groovypost.com [online], "How Safe is it to Download Chrome Extensions", published on Mar. 4, 2011, retrieved on Oct. 18, 2021, retrieved from URL<https://www.groovypost.com/howto/reviews/chrome-extensions-privacy-security/>, 7 pages.

Guyot, "Apple's ResearchKit: Our Complete Overview," Mar. 9, 2015, retrieved on Mar. 30, 2020, retrieved from URL<https://www.macstories.net/news/apples-researchkit-our-complete-overview/>, 8 pages.

Hematology.org [online], "Antithrombotic Therapy", published on Dec. 1, 2008, retrieved on Jan. 3, 2022, retrieved from URL<https://www.hematology.org/about/history/50-years/antithrombotic-therapy>, 2 pages.

Henze et al., "Push the study to the App store: evaluating off-screen visualizations for maps in the android market," Proceedings of the 12th Conference on Human-Computer Interaction with Mobile Devices and Services, Lisbon, Portugal, Sep. 7-10, 2010, 373-374.

Heron, "Ecological Momentary Intervention [EMI]: Incorporating mobile technology into a disordered eating treatment program for college women," Psychology—Dissertations, paper 157, 2011.

Illumina.com [online], "Understanding Epigenetic Modifications and Their Impact on Gene Regulation", published on or before Nov. 29, 2021, retrieved on Jan. 3, 2022, retrieved from URL<https://www.illumina.com/techniques/popular-applications/epigenetics.html>, 4 pages.

Kotsiantis, "Supervised Machine Learning: A Review of Classification Techniques", Informatica 31, Jul. 2007, pp. 249-268.

Lunn et al., "Using Mobile Technology to Engage Sexual and Gender Minorities in Clinical Research," PLOS ONE, May 2, 2019, 14(5), 19 pages.

makeuseof.com [online], "How Safe Is the Chrome Web Store Anyway?", published on Apr. 10, 2015, retrieved on Oct. 18, 2021, retrieved from URL<https://www.makeuseof.com/tag/secure-chrome-web-store-anyway/>, 16 pages.

Matthews, "Johns Hopkins Researchers to Use Apple Watch Data to Study Epilepsy," Oct. 15, 2015, retrieved on Mar. 30, 2020, retrieved from URL<https://hub.jhu.edu/2015/10/15/apple-watch-epi-watch/>, 3 pages.

Medvedeva et al., "EpiFactors: A Comprehensive Database of Human Epigenetic Factors and Complexes", Database, 2015, 10 pages.

Milward, "Ecological momentary assessment," Jul. 2015, retrieved on May 12, 2017, retrieved from URL <https://www.addiction-ssa.org/commentary/emerging-research-methods-series-ecological-momentary-assessment>, 3 pages.

Nanda et al., "dbEM: A Database of Epigenetic Modifiers Curated from Cancerous and Normal Genomes", Scientific Reports, Jan. 18, 2016, 6 pages.

Ncbi.nlm.nih.gov [online], "SERPINC1 Serpin Family C Member 1 [*Homo sapiens* (human)]", updated on Jan. 2, 2022, retrieved on Jan. 3, 2022, retrieved from URL<https://www.ncbi.nlm.nih.gov/gene/462>, 13 pages.

Obgyn.com [online], "Neural Networks", published in 2002, retrieved on Jan. 19, 2021, 34 pages.

PCT International Preliminary Report on Patentability in International Appln No. PCT/US2017/017480, dated Aug. 23, 2018, 13 pages.

PCT International Search Report and Written Opinion in International Appln. No. PCT/US2017/017480, dated May 17, 2017, 19 pages.

Pogue, "Apple's First 5 Health ResearchKit Apps in Brief," Jul. 1, 2015, retrieved on Mar. 30, 2020, retrieved from URL<https://www.scientificamerican.com/article/pogue-apples-first-5-health-researchkit-apps-in-brief/>, 4 pages.

Rabelo et al., "Development of a real-time learning scheduler using reinforcement learning concepts", Proceedings of the 1994 9th IEEE International Symposium on Intelligent Control, 1994, pp. 291-296.

Rauschert et al., "Machine Learning and Clinical Epigenetics: A Review of Challeneges for Diagnosis and Classification", Clinical Epigenetics, Apr. 3, 2020, 11 pages.

Runyan et al., "Virtues, ecological momentary assessment/intervention and smartphone technology," Frontiers in Psychology, May 2015, 6:481, 24 pages.

Sadilek et al., "Machine-Learned Epidemiology: Real-Time Detection of Foodborne Illness at Scale", Digital Medicine, Nov. 6, 2018, 7 pages.

(56) References Cited

OTHER PUBLICATIONS sbir.cancer.gov [online], "322 Real-Time Integration of Sensor and Self-Report Data for Clinical and Research Applications", published on Jun. 24, 2015, retrieved on Oct. 18, 2021, retrieved from URL<https://sbir.cancer.gov/funding/contracts/pastcontracts/322>, 3 pages.

sbir.cancer.gov [online], "340 Validation of Mobile Technologies for Clinical Assessment, Monitoring and Intervention", published on Jun. 24, 2015, retrieved on Oct. 18, 2021, retrieved from URL<https://sbir.cancer.gov/funding/contracts/pastcontracts/340>, 3 pages.

sbir.cancer.gov [online], "NIH/NCI 342: Validation of Mobile Technologies for Clinical Assessment, Monitoring and Intervention", published on Jul. 24, 2015, retrieved on Oct. 24, 2015, retrieved from URL<https://sbir.cancer.gov/funding/contracts/nihnci342>, 4 pages.

Shockney, "The Value of Patient Navigators as Members of the Multidisciplinary Oncology Care Team," 2017 ASCO Annual Meeting, ASCO Daily News, Jun. 6, 2016, [retrieved on Jan. 2, 2018], retrieved from: URL <https://am.asco.org/value-patient-navigators-members-multidisciplinary-oncology-care-team>, 3 pages.

Simon, "Patient Navigators Help Cancer Patients Manage Care," American Cancer Society, Feb. 24, 2017, [retrieved on Jan. 2, 2018], retrieved from: URL <https://www.cancer.org/latest-news/navigators-help-cancer-patients-manage-their-care.html>, 4 pages.

sitepoint.com [online], "How to Create a Chrome Extension in 10 Minutes Flat", published on Apr. 8, 2015, retrieved on Oct. 18, 2021, retrieved from URL<https://www.sitepoint.com/create-chrome-extension-10-minutes-flat/>, 11 pages.

smallbusiness.chron.com [online], "What Is the Chrome Web Store", published on Oct. 6, 2011, retrieved on Oct. 18, 2021, retrieved from URL<https://smallbusiness.chron.com/chrome-store-26652.html>, 5 pages.

Srivastava, Swati., "Understanding Genetic Variation as Risk Factors for Development Venous Thrombo-Embolism (VTE)", Advancements in Genetic Engineering, Feb. 10, 2016, 7 pages.

Taivan et al., "Application Diversity in Open Display Networks," Proceedings of the International Symposium on Pervasive Displays, Copenhagen, Denmark, Jun. 2014, 68-73.

techcrunch.com [online], "Google Gives Chrome Web Store a Welcome New Lick of Paint", published on Oct. 15, 2011, retrieved on Oct. 18, 2021, retrieved from URL<https://techcrunch.com/2011/10/25/google-gives-chrome-web-store-a-welcome-new-lick-of-paint/>, 8 pages.

Teems, "Automated Patient Navigation: Commission on Cancer and Other Requirements," Cordata Healthcare Innovations; Cordata Blog, Oct. 13, 2014, [retrieved on Jan. 2, 2018], retrieved from: URL <http://www.cordatahealth.com/blog/automated-patient-navigation-commission-on-cancer-and-other-requirements>, 4 pages.

Tiffin et al., "Linking Genes to Diseases: It's All in the Data", Genome Medicine, 2009, 77.1-77.7.

Tourous et al., "Empowering the Digital Therapeutic Relationship: Virtual Clinics for Digital Health Interventions," NPJ Digital Medicine, May 2018, 1(16):1-3.

web.archive.com [online], "Extension Templates and Samples", published on Jul. 15, 2020, retrieved on Oct. 18, 2021, retrieved from URL<https://web.archive.org/web/20200715011834/https:/dev.opera.com/extensions/extension-samples/>, 5 pages.

West et al., "There's an App for That: Content Analysis of Paid Health and Fitness Apps," Journal of Medical Internet Research, May-Jun. 2012, 14(3): e72, 12 pages.

U.S. Appl. No. 17/538,628, dated Nov. 30, 2021, 92 pages.

fabricgenomics.com [online], "Streamlined whole genome analysis for hereditary rare disease," Feb. 16, 2021, retrieved on Sep. 1, 2022, retrieved from URL<https://fabricgenomics.com/rare-disease-diagnostics/>, 5 pages.

* cited by examiner

USING GENETIC AND PHENOTYPIC DATA SETS FOR DRUG DISCOVERY CLINICAL TRIALS

BACKGROUND

Different types of monitoring and analysis involve sampling data from end devices (e.g., end user devices, endpoint devices, client devices, or user devices) that monitor subjects. The subject may be, for example, participants in a cohort of a clinical trial or patients undergoing therapeutic treatment or health monitoring. In such situations, the subjects or patients are typically administered a therapeutic, e.g., a pharmaceutical or pharmaceuticals, a treatment, a therapy, or some other combination of actions or substances to treat a medical condition, according to an administration schedule.

The data collected may be used for different purposes, depending on the objective of the monitoring. Data collection, however, is not a static endeavor. Depending on conditions indicated by the collected data, and emerging trends and patterns detected in data in a relevant knowledge base, the types of data and parameters for collecting data may need to be changed. For example, more of certain types of data may need to be collected, or, alternatively, certain types of data may no longer need to be collected. Data collection systems that fail to take into account the dynamic nature of both subject responses and an ever-evolving knowledge base are often subject to significant resource waste and inefficiency, as resources may be expended in monitoring that is ineffective or that fails to achieve the monitoring objectives. As a consequence of not considering dynamic nature of subject responses and the knowledge base, clinical trials may have to be extended or started over, at significant detriment to researchers and participants. In the case of therapeutic treatment, the lack of adaptive monitoring may result in patients being monitored in a manner that may negatively affect the quality of care the patients receive. For example, monitoring that exceeds the needs for a user may cause excessive intrusion, disruption, and burden on patients to collect data that ultimately is not needed or does not affect patient care, while monitoring that omits relevant types of data may result in inaccurate assessment of health risks, incorrect diagnosis, treatment selection, treatment dosage, and other types of suboptimal care. In particular, whether used for research or treatment, generalized monitoring schemes that do not take into account an individual's unique genetic profile and situation (e.g., behaviors, environment, and other epigenetic factors) may fail to collect the information needed to accurately detect and assess health risks, to select and configure preventative measures and therapies, and to accurately monitor patient responses to interventions.

Moreover, failure to adjust end-device monitoring dynamically may also result in collections of a vast amount of data that is irrelevant, which, in turn, results in noise that may obscure relevant data. Such lack of data hygiene creates difficulties in data mining and machine learning, as larger data sets are more difficult to analyze and may result in false-positive detection of signals, or false-negative omission of signals. Moreover, large data sets demand computational resources that otherwise could have been reduced by dynamic, adjustable end-device monitoring that is customized for an individual or device.

Additionally, as risks are identified and/or as additional data are collected, the administration profile for treatment or other interventions may require adjustment. However, it can be difficult, if not impossible, for a person to discern when such changes are necessary or recommended. Accordingly, the failure to timely change an administration profile may result in risk to the subjects or patients, and may also result in data collection of a data set that is susceptible to false-positive detection of signals or false-negative omission of signals.

SUMMARY

This specification describes a system that can provide dynamic end device monitoring of a subject according to a variety of adjustment factors. The system may be implemented using computer programs on one or more computers in one or more locations, including software executed on servers and/or client devices. Unlike many prior approaches, the present system is designed to customize monitoring performed for specific individuals and devices, including dynamically adjusting or adapting over time the monitoring profiles that direct how end devices (e.g., user devices) operate to collect monitoring data. The system can then cause end devices to implement the changes in monitoring, for example, by transmitting an updated monitoring profile to a device. The monitoring profile and related information can including instructions, monitoring parameter values, device configuration data, software, data collection rules, interactive elements, or other elements that change the way a device activates its sensors, interacts with users (e.g., through surveys, user interfaces, etc.), and transmits collected monitoring data to a server. The changes in monitoring, which can be customized for individual users or groups of similar individuals, can ensure that data collection operations performed are relevant for the individuals, in order to provide accurate and useful health data in an efficient manner that conserves battery life, network bandwidth, and processing resources of the end devices.

Health monitoring is an activity that is critical to the effectiveness of research in clinical trials as well as the effectiveness of prevention, management, and treatment of many health conditions. This is true in health research (e.g., clinical trials) as in healthcare delivery for individual. The medical field is increasingly recognizing the need to adopt precision health and precision medicine techniques to improve outcomes for patients. However, traditional monitoring approaches rarely provide the monitoring that meets the needs of different individuals. In particular, the static, generalized approaches many conventional systems result in over-monitoring for some patients and under-monitoring for others. In some cases, systems demonstrate both flaws by monitoring irrelevant aspects of health while not sufficiently monitoring the areas that relate to the user's actual health needs. The present system facilitates precision health and precision medicine by enabling a system to customize and personalize the scope of monitoring for individuals, including adjusting and adapting the monitoring over time as the individual's health and risks change. The monitoring that can be performed can include measurements of many types, including indicators of behavior (e.g., sleep, diet, physical activity, travel, social engagement, device usage, etc.), physiology (e.g., blood pressure, heart rate, respiration rate, body temperature, blood glucose level, blood oxygenation, body weight, etc.), mental health, and more. The monitoring can be performed by end device using a variety of techniques, including active sensing, passive sensing, user inputs (e.g., survey responses, ecological momentary assessments (EMAs)), interactive games, and more.

The systems described herein can dynamically adjust monitoring for an individual using genetic information and epigenetic information for a user. For example, the system can obtain genetic information for an individual as well as epigenetic information for the individual, e.g., data characterizing the behaviors, environment, context, and other factors that affect how the user's genes are expressed. The system uses the genetic information and epigenetic information for the individual to identify and evaluate health risks for the individual and the resulting monitoring needed to address those health risks. For example, the system can generate and store records (e.g., databases, models, etc.) indicating the known or predicted effects of genetic and epigenetic factors on health outcomes. These records may indicate that particular genetic characteristics increase the risk of a particular adverse health outcome (e.g., heart attack, stroke, onset of diabetes, etc.), and also that specific behaviors and environmental characteristics increase or decrease the likelihood or severity of the adverse health outcome. The system then customizes monitoring performed for different individuals based on these outcomes. For individuals that are determined to have the particular genetic characteristics, the system can configure monitoring to collect data to measure or detect the specific behaviors and environmental characteristics that are known or predicted to alter the risk in the context of the particular genetic characteristics. On the other hand, for individuals that are determined to not have the particular genetic characteristics, the system can configure monitoring performed to not collect data for those specific behaviors and environmental characteristics, thus avoiding an unnecessary burden on the individual and avoiding unnecessary consumption of limited battery power, network bandwidth, data storage space, and computational resources of the individuals' devices.

The use of genetic and epigenetic information in combination can be used to customize monitoring in various ways. For example, once monitoring data is set for an individual based on the user's genetic profile or health risks, the combination of genetic information and monitoring data (e.g., current monitored values and historical values) for epigenetic factors can enable a system to better assess health risks. For example, the system may determine that a particular gene variant provides increased susceptibility to deep vein thrombosis (DVT). Records of the system (e.g., models, rules, longitudinal data sets, etc.) can indicate that a low degree of movement increases the risk of DVT for people with the gene variant, much more so than for individuals without the gene variant. As a result, the system can identify individuals that have the particular gene variant and remotely set or adjust monitoring profiles for their devices (e.g., smart phones, smart watches, activity trackers, etc.) to monitor physical activity more intensely than for individuals that do not have the particular gene variant (e.g., monitoring step count hourly rather than daily, acquiring and reporting accelerometer data to a server instead of sending step count alone). With the monitoring data targeted to the known or predicted epigenetic factor of activity, the system can much more accurately personalize the assessment of DVT risk for individuals with the gene variant. For some, the system may determine that their monitoring data shows high or consistent activity, which reduces their risk of DVT compared to the average of individuals with the gene variant. For others, the system may determine that their monitoring data shows low or inconsistent activity, which increases their risk of DVT. The system can use each individual's combination of genetic profile and monitored data for epigenetic factors to calculate a risk level and update that risk level from time to time (e.g., periodically, continually, as new monitoring data is received, on demand, etc.). The system compares the risk levels to a threshold, and when the system determines that the risk exceeds a threshold, the system may adapt the monitoring further, for example, providing more intensive monitoring for factors that affect DVT risk or which indicate early signs or symptoms of DVT. This additional change in monitoring can include, for example, monitoring additional types of data, changing the parameters for data collection (e.g., to adjust the frequency, precision, triggers for collection, devices or sensors used, etc.), adding surveys or other interactions to collect data, and more. As a result, the system can adaptively tailor the monitoring performed for different individuals, based on the unique risk levels and situations shown by the combination of their genetic profiles and their monitored data for relevant epigenetic factors.

In addition to setting and adapting monitoring, the system can recommend or automatically carry out adjustments to treatments and interventions for an individual based on the same factors. For example, based on the genetic and epigenetic factors together indicating a DVT risk above a threshold, the system can implement a digital therapeutic intervention for a user. For example, the system can instruct a device of a high-risk individual to monitor physical activity of the user and intervene to promote movement if activity is below than a minimum level for more than a threshold amount of time (e.g., three hours). The system, through a rule processed by the user's end device or through instruction for intervention from a server, can cause the end device to provide various interactions (e.g., alerts, reminders, haptic feedback, media, etc.) to encourage the user to increase movement. Based on the user's monitoring data, and how the monitoring data indicates epigenetic factors that adjust the user's risk level, the system can also change the administration profile for a treatment, such as to change the dosage, intensity, frequency, or other parameters for treatment (e.g., adjusting the threshold for interaction from 3 hours of low activity to 2 hours of low activity; changing the form of intervention or the device used to supply the intervention). For example, the system can evaluate monitoring data to determine if the individual acted on the instruction to increase activity, potentially changing monitoring actions to better detect the extent that the user successfully completed the instructed actions and to provide real-time feedback to the individual.

As another example, the system can use genetic and epigenetic data for individuals to adjust monitoring for signs and symptoms of health effects as well as adjusting the administration of treatments. For example, the system may have databases or models that indicate that certain genetic characteristics may be known or predicted to affect the metabolism of certain medications or to affect the effectiveness of the medication or the likelihood or severity of side effects of the medication. In addition, the databases or models can characterize the ways that various patient attributes (e.g., demographic attributes), physiological characteristics, and behaviors individually or in combination provide differing levels of influence on outcomes of the medication depending on the genetic characteristics. With these data sets and health profiles for individuals, the system can select different data collection parameters (e.g., type of data to collect, frequency or collection schedule) for different individuals customized for their unique combination of genetic and epigenetic information. As a result, the monitoring can be adjusted to selectively collect data targeted to the particular risks and outcomes most applicable to each user. For example, when the user's genetic and epigenetic data indicate a high risk of a side effect, the system can adjust monitoring to measure physiological and behavioral characteristic that give early warning of onset of the side effects, quantify the frequency or severity of the side effects, or measure additional factors that stored data indicates can modulate (e.g., increase or decrease) the likelihood or severity of those side effects.

In medical and scientific literature, "genetics" often refers to study of individual genes while "genomics" often refers to study of multiple genes or even the entire genome of an individual. However, for ease of reference and to avoid repeating the phrase "genetic and/or genomic," the present document uses the term "genetic" in a broad sense to encompass the traditional meaning of both genetic (e.g., relating to individual genes) and genomic (e.g., relating to multiple genes or the genome as a whole). The term "genetic" as used herein thus refers to one or more aspects of the genome or an individual's genotype, whether relating one gene or genome characteristic or multiple. Consequently, "genetic data" may encompass information about a single gene, information about multiple genes, characteristics of genes individually or collectively, or other characteristics of a genotype. Thus, references to "genetic data" can include information about one gene of an individual, multiple genes (e.g., a subset of the genome that is less than the entire genome) of the individual, and/or the individual's genotype as a whole. References to "genetics" or "genetic" are not limited to a single gene and should be interpreted as also encompassing "genomics" or "genomic" unless context shows that only a single gene is involved (e.g., by reference to a specific gene or "single-gene genetic data" for example). In the disclosed systems, use of "genetics" or "genetic" data or analysis can refer interchangeably to "genomics" or "genomic" data or analysis.

In a similar manner, in medical and scientific literature, "epigenetics" often refers to processes that regulate how and when certain genes are turned on and turned off. Similarly, "epigenomics" often refers to analysis of epigenetic changes across multiple genes in a cell or in an entire organism. However, for ease of reference and to avoid repeating "epigenetic and/or epigenomic," the present document uses the term "epigenetic" in a broad sense to encompass the traditional meanings of both epigenetic (e.g., relating to influence on activity of individual genes) and epigenomic (e.g., relating to influence on activity of multiple genes). The term "epigenetic" as used herein thus refers to one or more aspects of the epigenome or an individual's epigenotype (e.g., relating to an effect on activity of at least one gene, but potentially relating to an effect on or across multiple genes). Consequently, "epigenetic data" may encompass information about influence on a single gene, on multiple genes, or other portions of a genotype. Thus, references to "epigenetic data" can include information about influence on expression or activity of a single gene of an individual, on multiple genes (but less than the entire genome), and/or on the individual's genotype as a whole. References to "epigenetics" or "epigenetic" are not limited to interactions with a single gene and should be interpreted as also encompassing the meaning of "epigenomics" or "epigenomic" unless context shows that influence or analysis for only a single gene (e.g., by reference to a specific gene or "single-gene epigenetic data"). In the disclosed systems, use of "epigenetics" or "epigenetic" data or analysis can refer interchangeably to "epigenomics" or "epigenomic" data or analysis. As an example, an "epigenetic factor" can be one that adjusts activity of one or more genes, and so the term can refer to a factor that affects expression of a single gene or may refer to a factor that affects expression of multiple genes or affects the interaction among multiple genes.

Health monitoring is an important part of health research, especially as clinical trials and other studies are increasingly performed remotely. For example, health research studies can involve remote monitoring of various aspects of the health of individuals, including physiological measures, behaviors, activities, mood or mental state, and so on. The monitoring can be carried out using various digital technologies (e.g., using sensors, patient surveys, user devices, and other data collection techniques). In particular, the adaptive and personalized monitoring techniques described herein are very effective in decentralized clinical trials. Decentralized clinical trials are often executed using telemedicine and mobile or local healthcare providers, using processes and technologies differing from the traditional clinical trial model. In many decentralized clinical trials, most or all of the monitoring and data collection occurs in the patient's normal daily environment rather than in a physician's office or other clinical setting, primarily using monitoring devices at each patient's home. As a result, the monitoring devices are distributed across a wide variety of geographical locations and the ability to adjust monitoring profiles remotely over a communication network is particularly important. In many cases, participants in decentralized trials visit a dedicated trial site (e.g., hospital or medical office) rarely or not at all. A decentralized clinical trial can use software and digital devices, such as smartphones and wearable devices, to provide monitoring and other interactions while participants proceed through their normal activities at home, at work, at school, etc. These studies are also sometimes referred to as "virtual trials" or "digital trials."

For example, in the example of a clinical trial, data may be collected from a variety of sources, including health history, electronic health records (EHR), data describing behaviors and lifestyles, genetic samples, medication history, and health monitoring data of individuals' information. The system evaluates drug indications and risks to support drug discovery. Such evaluation may include correlating/associating new findings (as relevant research relating to drug and genetic data are released), and predicting, based on a large sample distribution and participant responses, potential risks based on underlying health, environment, and genetics from a set of crowd-sourced participants. The system then delivers these evaluations and predictions to researchers for evaluating each participant with respect to inclusion or exclusion criteria for research/clinical trial participation, notifying participants in case of risk indicators, and providing interventions to help alleviate risks. The system also adjusts a monitoring profile of end devices (also referred to as "health monitoring devices") based on the latest evaluations and risks. The system can adjust the monitoring used in the clinical trial for individual participants in a cohort for the clinical trial, or may use aggregated information about the risks and circumstances of participants in the cohort to adjust monitoring for groups within the cohort (e.g., groups identified as having similar genetic or epigenetic data) or for the cohort as a whole. In the case of a therapeutic administration, the system may also adjust an end device to change such administration, e.g., a device that administers a pharmaceutical or provides a treatment stimulus.

The techniques described herein can enable pharmaceutical companies to develop more targeted or more precise drugs. The techniques enable researchers and clinicians to detect how individuals with different combinations of genetic and epigenetic factors. The data sets generated by the system allow a drug developer to tailor drug formulations and/or administration regimens for different subgroups or populations. For example, the developer can use the information learned by the system and the monitoring results generated by the system to determine that, for user having certain genetic features, a certain drug formulation, dosage, or administration regimen is most effective. Further, the data sets can demonstrate that even among individuals with a particular genetic feature (e.g., a certain gene variant), different formulations, dosages, or administration parameters are preferred when certain epigenetic factors are present (e.g., differences in environment, behavior, etc.).

Examples of end devices include mobile devices (e.g., smartphones, laptop computers, tablet computers, smart watches, activity trackers, wearable devices, digital assistant devices, body-worn sensors, etc.), exercise devices, and any other appropriate health monitoring devices. End devices can also be medical devices, such as glucometers, weight scales, assistive technology, medication administration equipment, and so on. In general, an end device or health monitoring device has the capability to collect information about the health of an individual, for example, information describing physiological properties (e.g., blood pressure, heart rate, respiration rate, etc.), behavioral properties (e.g., characteristics of sleep, diet, physical activity, etc.), mood or mental health, and so on. Health monitoring devices can collect health information using sensors (e.g., heart rate sensors, accelerometers, temperature sensors, gyroscope, camera, pressure sensor, etc.), user input (e.g., voice input, touchscreen input, interactions with buttons or other controls, or combinations of both, including sensing during user interactions with the device. One way that health monitoring devices collect data is through surveys presented at a health monitoring device, such as a smart phone or watch, which a user responds to in order to provide health information (e.g., mood, pain level, meal information, disease symptoms, etc.). Health monitoring devices can be configured, through parameter values, instructions, or other contents of a monitoring profile, to collect of specific types of health data in a specific manner (e.g., with a specific frequency, sensor type, etc.), including automatic collection of data in a repeated or periodic manner. This data collection may also include presentation of surveys, games, notifications, and other interactive elements through the user interface of a health monitoring device. User interactions, as with sensor data collection, can be set by a monitoring profile to occur at a consistent predetermined time or interval, in response to detection of a predetermined trigger or condition (e.g., detecting that a monitored measure satisfies a predetermined threshold), or in response to a user action or an instruction from a server over a communication network.

On a specific user (e.g., participant or patient) basis, the system receives genetic data (e.g., DNA sequencing) of the user and health data of the user (e.g., physiological data, behavior data, environmental data) monitored over a time period. The data can be monitored by one or more health monitoring devices. Using this data, the system generates a health profile for the user, and based on this health profile, determines a particular health risk for the user. The health risk is then used to determine a first monitoring profile for the user. This monitoring profile includes elements (e.g., parameter values, configuration data, instructions, rules, software, etc.) that cause the one or more health monitoring devices to monitor the user for a first set of types of health data in response to receiving the monitoring profile. The first health monitoring profile is then provided to the one or more health monitoring devices so that the health monitoring devices monitor the user according to the first health monitoring profile. For example, the health monitoring devices can each have an application installed that includes functionality to interact with various sensors and user interface elements of the health monitoring devices. The application can be configured to interpret and respond to received monitoring profiles, to selectively enable and configure the application's functionality to carry out the monitoring specified in a profile. As a result, the transmission of a monitoring profile can cause a device with the application to begin ongoing, repeated monitoring with the parameters specified in the monitoring profile.

The system can determine health risks in a variety of ways. For example, based on the health profile of the user, the system may determine a particular health risk such as arrhythmia, e.g., by comparing user health data with data describing genetic and health risk factors, using a machine learning system trained to determine a health risk, or by comparing user health data with the health profiles of a set of other users. The machine learning system can implement machine learning (e.g., convolutional neural network-based deep learning) algorithms to predict the health risk of the user. Such system can be trained on genetic and health risk factors of multiple users, e.g., by using them as training labels in a supervised machine learning.

In some implementations, the system initially enables a device to perform monitoring using a first health monitoring profile. While monitoring according the first health monitoring profile, the system receives, for the user, epigenetic data describing observations or measurements for epigenetic factors for the user. These epigenetic factors can be physiological, behavioral, environmental or other attributes that the system knows or predicts to affect a health risk. More specifically, the epigenetic factors can be characteristics or attributes that have been identified by the system as more likely to affect the health risk when certain genetic characteristics (e.g., presence or absence of a particular gene or gene variant, a predetermined combination of genetic traits) are present than when the genetic characteristics are not present. Based on the genetic data and the epigenetic data for the user, the system determines that health change event for the particular health risk has occurred for the user. In response, the system determines, for the particular health risk, a second monitoring profile for the user. The second monitoring profile is different from the first monitoring profile, and causes the one or more health monitoring devices to monitor the user to generate a second set of health data. For example, the second monitoring profile can change the types of data monitored (e.g., add or remove monitoring of a physiological attribute or behavioral attribute), change the manner of collecting data (e.g., changing which sensor or device is used, changing the collection technique from sensor data collection to survey data collection, changing the frequency that the data collection is repeated, etc.). The system then provides the second health monitoring profile to the one or more health monitoring devices so that the health monitoring devices monitor the user according to the second health monitoring profile.

The health change event that triggers the change in monitoring can include a change in the health risk that meets a change threshold based, at least in part, on the genetic data and the epigenetic data for the user. For example, a change in the user's sleeping behaviors (e.g., from sleeping 8 hours daily, on average, past month to sleeping 2 hours daily, on average, past three days) can prompt the system to determine such change constitutes as the health change event and adjusts the monitoring profile to monitor a set of health data (e.g., oxygen level) at an increased frequency from a frequency specified in the first monitoring profile, e.g., every 10 minutes instead of every hour. Alternatively or in addition, continuing this example, the system adjusts the monitoring profile to monitor additional health data (e.g., heart rate) not collected in the first set of health data.

In general, one innovative aspect of the subject matter described in this specification can be embodied in methods that include the actions of generating, for a user, a health profile for the user, a health profile based on one or more of genetic data of the user and health data of the user monitored over a time period, the health data received from one or more health monitoring devices over a time period; determining, based on the health profile of the user, a particular health risk for the user; determining, for the particular health risk, a first monitoring profile for the user that causes the one or more health monitoring devices to monitor the user for a first set of health data according to the first monitoring profile; providing, to the one or more health monitoring devices, the first monitoring profile; receiving, for the user, epigenetic data describing epigenetic factors for the user; determining that a health change event for the particular health risk has occurred for the user based, at least in part, on the genetic data and the epigenetic data for the user, and in response: determining, for the particular health risk, a second monitoring profile for the user that causes the one or more health monitoring devices to monitor the user for a second set of health data according to the second monitoring profile, wherein the second monitoring profile is different from the first monitoring profile; and providing, to the one or more health monitoring devices, the second monitoring profile. Other embodiments of this aspect include corresponding systems, apparatus, and computer programs, configured to perform the actions of the methods, encoded on computer storage devices.

Some implementations also include receiving the first set of health data from the one or more health monitoring devices; and determining that the health change event for the particular health risk has occurred for the user based, at least in part, on the genetic data and the epigenetic data for the user comprises determining that the health change event for the particular health risk has occurred for the user based on the genetic data, the epigenetic data, and the first set of health data.

Some implementations also include receiving, from the one or more health monitoring devices, the second set of health data monitored by the health monitoring devices according to the second monitoring profile, wherein the second set of health data monitored during a first time duration is different form the first set of health data monitored during the first time duration.

In some implementations, determining a particular health risk for the user includes comparing the health profile of the user with data specifying genetic and health risk factors and identifying a particular health risk for the user based on the comparison.

In some implementations, determining a particular health risk for the user includes receiving a set of health profiles of other users; comparing the health profile of the user with characteristics of health profiles in the set of health profiles of other users; and identifying a particular health risk for the user based on the comparison In some implementations, determining a particular health risk for the user includes providing data from the health profile as input to a trained machine learning model trained to determine a health risk based on the input; and receiving, from the trained machine learning model, data identifying the particular health risk.

In some implementations, determining that the health change event for the particular health risk has occurred for the user has occurred includes determining, based, at least in part, on the genetic data and the epigenetic data for the user, that a change in the health risk that meets a change threshold has occurred.

In some implementations, determining, based, at least in part, on the genetic data and the epigenetic data for the user, that a change in the health risk that meets a change threshold has occurred includes determining that the epigenetic data that indicates the epigenetic factor for the user has caused an increase in the health risk that meets an increase threshold, In some implementations, determining, for the particular health risk, the second monitoring profile for the user includes adjusting the first monitoring profile to cause the one or more health monitoring devices to monitor the user for a set of health data at an increased frequency from a frequency specified in the first monitoring profile.

In some implementations, determining, based, at least in part, on the genetic data and the epigenetic data for the user, that a change in the health risk that meets a change threshold has occurred includes determining that the epigenetic data that indicates the epigenetic factor for the user has caused an increase in the health risk that meets an increase threshold.

In some implementations, determining, for the particular health risk, the second monitoring profile for the user includes generating the monitoring profile to cause the one or more health monitoring devices to monitor the user for the first set of health data and additional health data not in the first set of health data, wherein the first set of health data and the additional health data not in the first set of health data comprise the second set of health data.

In some implementations, the method further includes: based on the genetic data for the user, identifying, by the one or more computers, a genetic characteristic that increases a likelihood of the particular health risk for the user; and selecting, by the one or more computers, a set of epigenetic factors for the user based on the identified genetic characteristic, wherein the epigenetic factors comprise environmental, behavioral, or physiological attributes that are determined to or are predicted to affect a likelihood or severity of the health risk for individuals having the genetic characteristic. Determining the first monitoring profile comprises generating or selecting the first monitoring profile to include monitoring of the set of epigenetic factors selected for the user; providing the first monitoring profile causes the one or more health monitoring devices to initiate measurements for the set of epigenetic factors using sensors or surveys presented by the one or more health monitoring devices; and receiving the epigenetic data comprises receiving data indicating measures of each of the epigenetic factors in the set of multiple epigenetic factors that were selected for the user.

Another innovative aspect of the subject matter described in this specification can be embodied in methods that include the actions of receiving, for each user of a plurality of users, a health profile for the user, the health profile for the user based on one or more of genetic data of the user and health data of the user describing health aspects of the user, wherein the health profile includes a description of an administration of a therapeutic according to a first administration profile; receiving over a first time period, for each of the users, a first set of health data from one or more health monitoring devices assigned to the user over the first time period, and storing, for each of the users, the first set of health data of the user in the health profile of the user; determining, based on the health profile of the users, therapeutic interaction data, and genetic data, genetic and epigenetic correlations of risks across the plurality of users; based on the determination of risks across the plurality of users, adjusting, for at least one of the users, the first administration profile to a second administration profile that is different from the first administration profile, and includes a description of an administration of the therapeutic that is different from the administration of the therapeutic described in the first administration profile; and receiving over a second time period after the adjustment of the first administration profile to the second administration profile, for the at least one of the users, a second set of health data from one or more health monitoring devices assigned to the at least one of the users and storing, for the at least one of the users, the second set of health data in the health profile of the at least one of the users.

In some implementations, the adjusting the first monitoring profile to a second monitoring profile for the user that causes the one or more health monitoring devices to monitor the user for a second set of health data according to the second monitoring profile, wherein the second monitoring profile is different from the first monitoring profile; and receiving, from the one or more health monitoring devices, the second set of health data monitored by the health monitoring devices according to the second monitoring profile and storing the second set of monitored health data of the user in the health profile of the user.

In some implementations, adjusting the first monitoring profile to the second monitoring profile comprises adjusting the first monitoring profile to cause the one or more health monitoring devices to monitor the user for a set of health data at an increased frequency from a frequency specified in the first monitoring profile.

In some implementations, the adjusting the first monitoring profile to the second monitoring profile includes adjusting the first monitoring profile to cause the one or more health monitoring devices to monitor the user for the first set of health data and additional health data not in the first set of health data, wherein the first set of health data and the additional health data not in the first set of health data comprise the second set of health data.

In some implementations, determining, based on the health profile of the users, drug interaction data, and genetic data, genetic and epigenetic correlations of risks across the plurality of users includes providing data from the health profiles of the users, drug interaction data, and genetic data as input to a trained machine learning model that has been trained to predict the genetic and epigenetic correlations; and receiving, from the trained machine learning model, predictions of the genetic and epigenetic correlations.

In some implementations, receiving, for each user of the plurality of users, the health profile for the user includes receiving data from electronic health records for the user; receiving DNA profile data of the user; and receiving data describing behavior and lifestyle information for the user.

In some implementations, the first administration profile specifies and administration of a drug according to a first schedule, and the second administration profile specifies an administration of the drug according to a second schedule that different from the first schedule.

In some implementations, the first administration profile describes an administration of only a first drug, and the second administration profile specifies an administration of the first drug and a second drug, wherein the second drug is not specified to be administered in the first administration profile.

The subject matter described in this specification can be implemented in particular embodiments so as to realize one or more of the following advantages. The system uses the health profile for an individual to determine a monitoring profile that specifies one or more health monitoring device parameters, such as what to monitor and how often to monitor. The system can adjust and adapt the monitoring performed by remote devices over time to account for the changes in epigenetic data (e.g., monitored changes in aspects of the behavior environment that are known to or are determined likely to alter health risks and health outcomes in the context of certain genetic characteristics). Using the health profile in determining the monitoring profile not only provides personalized health monitoring by monitoring the most relevant physiological, behavioral, and environmental factors for the individual, but also saves computational resources by monitoring only relevant attributes of the user. For example, an oxygen level can be monitored for users at increased risk for having a stroke due to certain genetic and epigenetic characteristics, but is not monitored for others whose genetic and epigenetic characteristics indicate low risk. Moreover, by tailoring the data monitored based on the user's condition, the data set that is collected will result in data that is tailored for specific conditions, resulting in data that is less likely to include irrelevant information and more likely to include relevant information for the condition that data that is simply monitored in a static manner. This results in a more efficient use of bandwidth, data storage, and data processing.

Much of medical monitoring is performed by small battery-powered devices that have limited power reserves. Many of these devices, including smart phones, smart watches, and activity trackers, are often expected to operate continuously for hours or days without recharging, and so need to conserve power to operate for the extended duration that users expect. Repeated data collection, through sensor operation or through on-screen interactions, is necessary, but it has the potential to quickly deplete a battery's energy stores if the data collection is not limited and managed appropriately. When devices perform excessive sensing and deplete battery reserves too quickly, they increase the risk that the device may run out of power and cease monitoring, or that the user may become frustrated and manually terminate monitoring or stop using the device. In health monitoring, the failure to conduct the needed monitoring can jeopardize the user's health, since conditions indicating increased risks or the onset of adverse events can no longer be detected. Similarly, in clinical trials, gaps in data collection may result in users failing to comply with the data collection requirements of the trial, which can jeopardize the validity of the study and cause months of monitoring to be wasted. As a result, the ability of the present system to alter and adjust the monitoring performed, and thus the power use and other resource use expended, is a significant improvement for monitoring devices. The present system can personalize monitoring based on an individual's genetic characteristics and the corresponding epigenetic data that is relevant to those genetic characteristics, enabling selective monitoring of the properties that are most important to determining the user's health risks and treatment while avoiding the inefficiency of monitoring of items that are not applicable to the user. In the same way that the selective monitoring reduced power consumption and battery life, the targeted selective monitoring also reduces network bandwidth consumption, reduces data storage space usage, and reduces processor utilization, all of which are also constrained in health monitoring devices which are often mobile, battery-operated devices.

In addition, the system achieves efficiency in monitoring by detecting health change events and adjusting monitoring in response. For example, the system determines a health change event (e.g., a change in behavior, a change in likelihood for a health risk, the occurrence of a new health risk, an existing health risk ending) based on the user's health data (including previous measurements by the health monitoring devices) and adjusts the monitoring profile of the user. This feedback loop optimizes the monitoring profile and enables computationally efficient health monitoring. For example, after determining that the user is no longer at increased risk for having a stroke (e.g., as a consequence of the system evaluating the user's recent sleeping pattern as indicated by movement sensors and/or user survey responses), the system causes the user's device to decrease the frequency of measuring the oxygen level, saving computational time and power.

The system further can build a knowledge graph to facilitate effective identification of health risks and to improve the user's understanding of his or her overall health and underlying risk factors. For example, the user can explore which risk factors contribute to his or her particular health risk. The knowledge graph can be utilized to train, or optimize, the machine learning model used to predict the health profile of the user. The user interface also allows the user to improve the user's health by identifying risk mediating factors, improving current treatment regimens, and connecting the user to appropriate healthcare providers.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
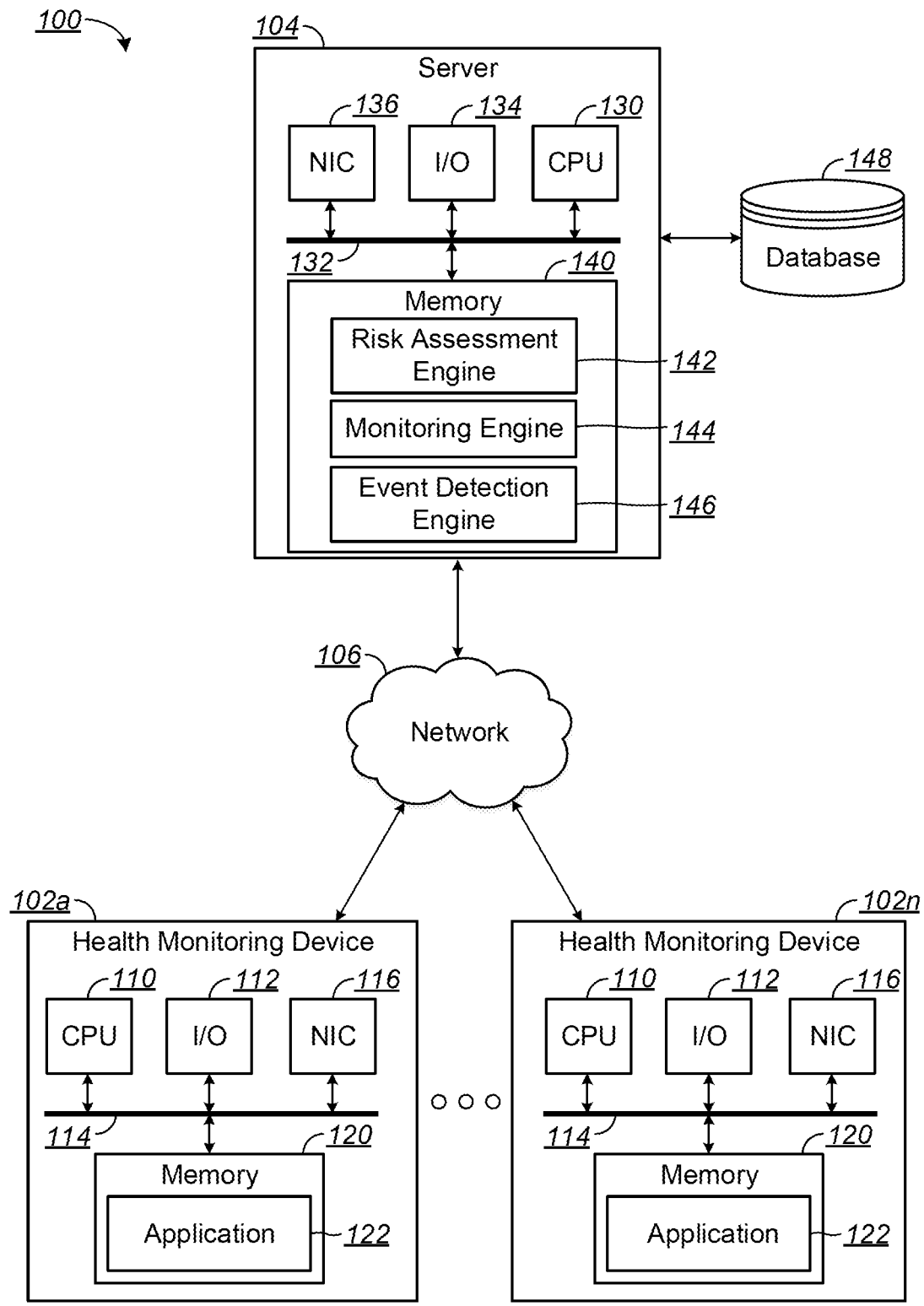
FIG. 1 is an illustration of an example computing system.

The subject matter of this specification relates to determining end dynamic device monitoring profiles and administration adjustments. In this specification, and example system and method are described in the context of a health monitoring system that can be used in a clinical trial setting or in a therapeutic setting. However, the systems and method described herein can be used in other contexts in which health is monitored or personalized risks are assessed.

As used in this specification, a monitoring profile for a set of end devices causes the end devices to monitor a user for a first set of health data according to the monitoring profile. An administration profile, on the other hand, specifies an administration of a therapeutic, e.g., according to a schedule or a set of rules. As used in this specification, a therapeutic can be a pharmaceutical or pharmaceuticals, a treatment, a therapy (e.g., physical therapy), digital therapeutics, or some other combination of actions or substances to treat a medical condition. These profiles, the data and processes underlying the profiles, and how the profiles are adjusted, are described in more detail below. In the examples that follow, the end devices are health monitoring devices, e.g., devices that can be used to monitor at least some aspects of a user's health. Health monitoring devices include smart phones, smart watches, activity trackers, laptop computers, medical devices (e.g., glucometers, pulse oximeters, thermometers, weight scales, etc.) and other devices that can be used to gather health information through sensors, user interfaces, or other means.

The example implementations include dynamic monitoring profile adjustments for particular users based on user-specific data, and dynamic monitoring profile adjustments and/or administration adjustments based on various information such as the health profile of the users, drug interaction data, and genetic data, genetic and epigenetic correlations of risks across the users.

A dynamic end device monitoring profile for a user is determined using the user's genetic data and epigenetic factors. Specifically, the system generates a health profile that aggregates genetic data, health data, and epigenetic data of the user and other users and determines health risks based on the health profile of the user. The system causes one or more health monitoring devices to monitor the user based on a monitoring profile that specifies a set of (health) data to be monitored and their corresponding frequencies. The system detects a health change event (also referred to as an event) for the particular health risk and adjusts the monitoring profile. The adjusted monitoring profile can include additional data not in the set of data to be monitored and different frequencies of monitoring the data. The system causes the health monitoring devices to monitor the user based on the adjusted monitoring profile.

The latter implementation is directed to adjusting one or more of an administration profile or a monitoring profile for end devices based on data across multiple users. In an example, a health profile for the user includes a description of an administration of a therapeutic according to a first administration profile. For each of the users the system receives a first set of health data from one or more health monitoring devices assigned to each the users, and then determines, based on the health profile of the users, drug interaction data, and genetic data, genetic and epigenetic correlations of risks across the users. Based on the determined risks, the system adjusts, for at least one user, the first administration profile to a second administration profile or the first monitoring profile to a second monitoring profile.

Genetic data refers to data that describes characteristics of an individual's genome, typically acquired through DNA or RNA analysis. As discussed above, the term "genetic data" is used to encompass both information about individual genes as well as genomic data about multiple genes and genome characteristics other than genes. This includes information about the genotype of the individual, whether considered as the individual's entire collection of genes or for one or more subsets of the individual's genes (e.g., whether the genotype may indicate particular alleles or variant forms of a gene that affect for particular traits or characteristics). Genetic data can include data describing the structure, function, mapping, and heredity of features of the genome. A genome is an organism's complete set of DNA, including all of its genes as well as its hierarchical, three-dimensional structural configuration. Genetic data can include genetic data relating to individual genes and their roles in inheritance. While genetic data can include information about individual genes or in some cases include only information about certain specific genes, genetic data as used herein can encompass more than single-gene determinations and can encompass intragenomic phenomena (e.g., occurring within the genome) such as epistasis (e.g., effect of one gene on another), pleiotropy (e.g., one gene affecting more than one trait), heterosis (e.g., hybrid vigor), and other interactions between loci and alleles within the genome.

Genetic data for an individual may include results of gene sequencing part or all of the individual's genome. While the genetic data for an individual may include the results of whole genome sequencing, genetic data may alternatively represent sequencing of only part of a user's DNA. Similarly, while genetic data may specify actual base pair sequences in some cases, the genetic data may alternatively be expressed in other forms derived from DNA or RNA analysis or sequencing, such as classification results, identifiers for gene variants present, a list of alleles present, a binary indication whether certain a genetic characteristic or combination of characteristics are present or absent, and so on. As another example, an individual's genome may be assigned to a particular class (e.g., classification, category, cluster, or profile) based on a combination of properties of the genome. The genetic data for the individual may indicate the class or classes that the user's genome is determined to fit in. These forms of genetic data can indicate or represent higher-level characteristics of one or more genes without directly including sequence data. For example, genetic data for an individual may indicate a set of gene variants present in the individual's genome, such as indicating a particular single-nucleotide polymorphism (SNP) (e.g., a germline substitution of a single nucleotide at a specific position in the genome) that an individual has. While one individual may have whole-genome sequence available in his genetic data, another individual may have only limited data indicating the presence or absence of a specific SNP. The systems described herein can be configured to use either or both types of data, as well as other indications of at least a portion of the genotype of the individual, to monitor health risks for the individual, detect health events for the individual, change monitoring profiles of devices of the individual, and change administration profiles for treatment of the individual.

Epigenetics and epigenomics involve the study of how behaviors and environment can cause changes that affect the way genes are used and expressed in the body. As discussed above, "epigenetic factors" and "epigenetic data" are used to broadly encompass influences on single genes as well as influences on or among multiple genes. Thus, epigenetic factors as discussed herein can be epigenomic factors, and are not limited to affecting individual genes. Epigenetic changes are genetic modifications that impact gene activity without changing the DNA sequence. Without changing an individual's DNA sequence, epigenetic changes can change how the body reads or uses a DNA sequence. For example, gene expression refers to how often or when proteins are created from the instructions within genes. Epigenetic factors can affect gene expression to turn genes "on" and "off." An individual's environment and behaviors, such as diet and exercise, can result in epigenetic changes and thus change how genes are expressed.

There are many different mechanisms through which epigenetic changes can affect gene expression, and additional mechanisms continue to be discovered. One example, is DNA methylation, which operates by adding a chemical group to DNA. Typically, this group is added to specific places on the DNA, where it blocks the proteins that attach to DNA to read the gene. This chemical group can be removed through demethylation. Typically, methylation turns genes "off" and demethylation turns genes "on." As another example, epigenetic changes can operate through histone modification. DNA wraps around proteins called histones. DNA wrapped tightly around histones cannot be accessed by proteins that read the gene. Some genes are wrapped around histones and are turned "off" while some genes are not wrapped around histones and are turned "on." Chemical groups can be added or removed from histones and change whether a gene is unwrapped or wrapped ("on" or "off"). As another example, non-coding RNA can help control gene expression by attaching to coding RNA, along with certain proteins, to break down the coding RNA so that it cannot be used to make proteins. Non-coding RNA may also recruit proteins to modify histones to turn genes "on" or "off."

Epigenetic factors are influences that affect (e.g., promote, inhibit, or change the likelihood of) the development of observable traits or health outcomes for an individual (e.g., phenotypes) through their interaction with or presence in combination with certain genetic characteristics (e.g., genes, gene variants, combinations of genetic sequences, etc.). In other words, epigenetic factors can be influences, whether external to the individual (e.g., the environment) or internal (e.g., age, disease state, physiological attributes, the individual's behavior), that can cause epigenetic changes that alter gene activity or gene expression. The factors that cause epigenetic changes for different genes (or for different combinations of genes or for different variants of genes) can be different, resulting in different epigenetic factors being identified and measured for different genes. For example, one gene may be strongly affected by diet and not exercise, while another gene may be strongly affected by exercise and not diet. Similarly, among various different variants for a specific gene, different variants may be affected by different environmental and behavioral factors, or some variants may be influenced more strongly by an environmental or behavioral factor than others.

Epigenetic factors can be factors that cause epigenetic changes or effects, especially for particular genetic characteristics (e.g., characteristics of at least a part of the genome). More generally, epigenetic factors can be those that alter the likelihood of certain phenotypes or changes in phenotype, even if not through a direct, known mechanism. Studies of epigenetics (including epigenomics) often assess the multitude of chemical compounds that affect expression of the genome. For example, the epigenome can be considered to include multitude of chemical compounds or other signals that instruct the genome what to do. The epigenome includes chemical compounds and proteins that can attach to DNA and direct such actions as turning genes on or off, controlling the production of proteins in particular cells. When epigenetic compounds attach to DNA and modify its function, they are said to have "marked" the genome. These marks do not change the sequence of the DNA. Rather, they change the way cells use the DNA's instructions. The marks are sometimes passed on from cell to cell as cells divide. Some marks can be passed down from one generation to the next. The epigenome can vary among different types of cells, for example, with different epigenetic marks for blood cells and liver cells. Thus, a single individual can have multiple epigenomes for different types of cells, where each epigenome is the collection of epigenetic marks on the DNA in a single cell.

The epigenetic factors discussed herein can include chemicals and the chemical modifications to DNA and DNA-associated proteins that alter gene expression, but epigenetic factors are not limited to those. More broadly, epigenetic factors can also include characteristics of the environment, an individual's behavior, or an individual's physiology or experience (e.g., age, weight, prior surgeries, chronic conditions) that can cause epigenetic changes or change the likelihood or manner in which genes are expressed, potentially by causing epigenetic change through a chemical route of action. For example, ambient light levels, sound levels, and other environmental conditions are not chemicals that mark DNA but nevertheless can be considered epigenetic factors for some genes, since exposure can cause processes or effects in the body that lead to epigenetic changes. Similarly, user behavior, health status measures, physiological states, and so on can be considered epigenetic factors when they affect the body or are indicators of conditions that do affect gene activity. Characteristics can be epigenetic factors for a gene or other genetic characteristic by affecting to the likelihood that a gene is expressed, whether or not there is a direct path for chemical alteration (e.g., methylation) of DNA. Indeed, the relationships between observable behaviors and gene expression are often complex and nonlinear.

Accordingly, the systems herein do not require knowledge or verification of the mechanism by which an environmental, behavioral, or physiological influence affects expression of a gene in order for the systems to be able to use the relationship in assessing health risks and adjusting monitoring and treatment for the patient. For example, a system can learn which characteristics and conditions are epigenetic factors for different genes through machine learning, using data sets of genetic data and longitudinal monitored health data for many individuals as training data for machine learning models. Using machine learning or other modeling techniques (e.g., statistical analysis, rule-based models), the system can identify which types of data (e.g., air quality, step count) have influence in the presence of specific genes. More particularly, the system can characterize the level of epigenetic effect of a measurable factor on gene expression or a health outcome, such as by quantifying the amount of effect (e.g., amount of change in likelihood or severity of a health risk) expected for different measurements of the factor. For example, the system can determine, for a given gene and epigenetic factor, a table, curve, equation, or model that relates the level of a measured factor (e.g., hours of sleep) with the increase in likelihood or expected severity for an adverse health condition. For example, the system can determine, for a given gene or for a particular gene variant, the levels or ranges of a measurable factor where an epigenetic effect begins or reaches a threshold level of influence (e.g., air particulate levels above 100 micrograms per cubic meter of air, step count less than 2000 steps).

As used herein, epigenetic factors include those that cause heritable or non-heritable epigenetic changes. While some epigenetic factors can cause changes to DNA that are passed on to offspring, other epigenetic factors that affect the development of or likelihood of a phenotype of an individual without being capable of being passed on the next generation are still used by the system to inform health risk assessment, monitoring, and treatment. In many cases, a health risk or adverse health event can be a phenotype of interest, and the epigenetic factors that are identified and monitored are those that are determined to be or are predicted (e.g., through machine learning modeling) to be factors that change the likelihood of or alter the magnitude or severity of those phenotypes.

Epigenetic factors can include environmental characteristics and behavioral characteristics for an individual. Measurement can be performed for a variety of aspects of a user's environment (e.g., air quality, sound levels, light, temperature, water quality, chemical exposure, etc.) and a user's behavior (e.g., sleep, diet, exercise, travel, social activity, etc.). Physiological measures (e.g., blood pressure, heart rate, respiration rate, blood oxygenation level, blood sugar level, weight, body temperature, etc.), demographic factors (e.g., age, sex, etc.), and other health measures (e.g., medications taken, chronic conditions, medical history, etc.) can also be epigenetic factors. However, in many cases, most of these aspects have low or no influence on the expression of most of an individual's genes. Consequently, measuring these factors arbitrarily or comprehensively would consume excessive resources (e.g., battery power, network bandwidth, data storage space, processing capability) while providing little benefit, if any, to the individual. As a result, to make monitoring more efficient and effective, monitoring can be performed selectively, targeted to collect the types of data that are identified by the system as the most significant epigenetic factors for the individual. These can be the items identified as strongest epigenetic factors for at least a portion of the individual's genome, e.g., scored or ranked by the system as having the greatest magnitude or likelihood of effect on expression of certain genes related to a health risk or health condition of interest for the user. In addition, or as an alternative, the epigenetic factors to monitor can be selected as the items that affect expression of genes for the most serious or likely health risks for the patient. As a result the system can adjust the monitoring performed for each individual to detect and characterize the most urgent or serious health risks for the individual, as determined through analysis of the individual's genetic data and through the use of mappings, models, or other data indicating which items act as epigenetic factors for different genetic characteristics.

Epigenetic data for an individual refers to the results of monitoring epigenetic factors. For example, epigenetic data can include measurements, sensor data, survey answers, or other indicators for types of data that the system identified as epigenetic factors for genetic characteristics (e.g., gene variants, gene sequences, etc.) in the genome of the individual. With genetic data for an individual, the system can identify that specific genome characteristics are present. The system can then select epigenetic factors to monitor for the user and use the resulting monitoring data (e.g., measurements, sensor data collection, survey results) as epigenetic data. In some cases, the system can identify, out of a set of existing data for a user or generalized monitoring for a user, the data elements that represent measures for epigenetic factors for the identified genome characteristics, and this extracted data can be used as epigenetic data. Thus, the epigenetic data for the individual can be monitoring data or measurement data that describes the values or state of epigenetic factors that the system has selected as relevant to the user's genome.

In some implementations, the epigenetic data can be the data that describes measured values for, or indicators of the state of the individual for, a set of epigenetic factors selected by the system as relevant to a particular health risk that the system has identified and is monitoring for the individual. Rather than including measures for an arbitrary or all-encompassing set of potential epigenetic factors, the epigenetic data used in the system can be measures for a limited set of epigenetic factors selected by the system for a particular health risk (e.g., DVT, heart attack, stroke, etc.) and the set of genes or genome characteristics identified as affecting that health risk. In some cases, the epigenetic data are results of monitoring an item selected to be monitored based on a determination by the system that the user had a particular genetic characteristic and that the item to be monitored affects expression of the genetic characteristic. In some implementations, epigenetic data represents measures of an item that the system determines to have at least a minimum level of correlation with, or magnitude or likelihood of effect on, occurrence of a phenotype of interest when one or more genome characteristics are present. For example, when a gene variant is known to or predicted to have at least a minimum level of effect on a phenotype (e.g., health risk, health condition, etc.), the system can consider a behavioral or environmental factor to be an epigenetic factor for the gene variant when it has at least a predetermined minimum threshold level of effect on occurrence of the phenotype in those that have the gene variant.

For example, the system may identify a user as being at risk of DVT due to genetic data for the user indicating the presence of a certain gene variant that records or models of the system indicate as increasing the likelihood of DVT. The epigenetic data for the user can be a set of measures (e.g., values) for each of multiple types of data (e.g., age, blood pressure, air quality level, average daily step count, average amount of sleep per night) that the system determines or predicts to be epigenetic factors due to their affecting DVT risk when the gene variant is present.

In many cases, these epigenetic factors that affect risk for those having the gene variant may be different from the general factors that are used for monitoring DVT risk generally or for those without the gene variant. For example, a certain factor, such as air quality level, may have a much stronger effect on the likelihood of DVT occurrence (e.g., increasing the risk level) for those that have the gene variant than for those who do not. As a result, while air quality level may not be a primary or significant factor to monitor for DVT risk assessment generally, the system can prioritize monitoring air quality level for the individual that has the gene variant, based on analysis of the genetic data for the individual and identifying the presence of the gene variant. Indeed, they system can manage monitoring of other individuals for DVT risk and omit air quality monitoring for individuals that do not have the gene variant, based on determining that air quality level has below a threshold level of effect on DVT risk for individuals that do not have the gene variant. Thus, the system can set the monitoring performed for individuals differently based on differences in their genetic data, even when monitoring for the same health risk or health condition (e.g., phenotype). The system customizes the monitoring for individuals to selectively measure the epigenetic factors, determined or selected based on the individual's particular genetic data, that affect health risks for the user.

While some prior systems may capture the information about environmental conditions and behavior, they typically do not have the ability to identify or predict factors as epigenetic influences on the particular genome of an individual and the health risks of that individual. Nor do prior systems apply the relationships between genetic data and epigenetic data to adjust and adapt the health monitoring performed for an individual. On the other hand, the systems described herein can customize monitoring to capture data for the items that serve as epigenetic influences for the individual's specific genome. This can include adding monitoring of items that typically would not be monitored for other individuals having the same health risks and health condition (e.g., where the presence of a gene variant makes certain environmental or behavioral factors more strongly influence phenotype than in those without the gene variant). Similarly, this can include omitting monitoring of items that typically would be monitored for other individuals having the same health risks and health condition (e.g., limiting monitoring where an individual's genetic data indicates a lowered risk or absence of high-risk genome characteristics, or where genome characteristics correspond to low epigenetic effect of some items that could be monitored). The present system can track behaviors such as sleep and exercise, and identify relationships between the tracked behaviors (e.g., the amount or quality of sleep, the amount and intensity of exercise) and aspects of the user's genotype (e.g., a specific gene variant present, a combinations of alleles present, etc.). This enables the system to assess health risks for the individual (e.g., identifying and quantifying risks) much more accurately through the combination of genetic data and corresponding epigenetic factors that are known to or are predicted to affect expression of genetic characteristics.

These features and additional features are described in more detail below.

FIG. 1 illustrates an example computing system 100 for an example implementation directed to dynamic monitoring profile adjustments for particular users. The system 100 includes a plurality of health monitoring devices 102a through 102n (referred to collectively as health monitoring devices 102) in communication with a server 104 via a network 106, which may be a wired or wireless network or any combination thereof.

In some implementations, each health monitoring device 102 is a mobile device (e.g., smartphone, laptop, tablet, wearable device, digital assistant device, etc.). The health monitoring device 102 can execute an application 122. The application 122 can include one or more electronic resources including a mobile application and a web environment displayed by a browser program.

In some implementations, the same user is associated with different health monitoring devices 102. For example, the user operates a smart watch or activity tracker that monitors the user's heart rate (e.g., through an application that causes sensor data from a heart rate sensor of the watch to be captured), a smart phone that monitors the user's exercise index (e.g., based on the number of steps taken daily), and a pulse oximeter that monitor the user's oxygen levels. In some implementations, multiple different users operate health monitoring devices 102 that use the same application 122. However, the different users can have different monitoring profiles sent to their respective devices, causing the monitoring to be different for different users (e.g., capturing different types of health data, capturing data at different times or frequencies, etc.).

The health monitoring devices 102 may each include a processor (e.g., central processing unit) 110 in communication with input/output devices 112 via a data bus 114. The input/output devices 112 can include a sensor, touch display, keyboard, mouse, and the like. A network interface circuit 116 is also connected to the bus 114 to provide wired and/or wireless connectivity to the network 106. A memory or other storage medium 120 is also connected to the bus 114. The memory 120 stores instructions executed by the processor 110. In particular, the memory 120 stores instructions for the application 122, which communicates with the server 104.

The server 104 includes a processor 130, data bus 132, input/output devices 134 and a network interface circuit 136 to provide connectivity to the network 106. A memory 140 is connected to the data bus 132. The memory 140 stores various software modules, such as a risk assessment engine 142, a monitoring engine 144, and an event detection engine 146 with instructions executed by the processor 130 to implement operations disclosed in connection with FIGS. 2 through 7. In some implementations, a processing engine can include multiple different engines (e.g., an engine encompassing both the risk assessment engine 142 and the monitoring engine 144) such that common components of different engines can be shared.

The system 100 includes the risk assessment engine 142 that generates a health profile for the user based on genetic data, health data, and/or monitoring data (which can include epigenetic data of the user). The risk assessment engine 142 also determines a particular health risk for the user based on the health profile of the user. For example, based on the user's genetic data (e.g., having risk genetic variant(s) for type 2 diabetes) in conjunction with the user's epigenetic data (e.g., having diet of high sugar intake), the risk assessment engine 142 determines that the user is at increased risk for developing type 2 diabetes. The risk assessment engine 142 is described in more detail below, referring FIG. 2.

The system 100 includes the monitoring engine 144 that determines a monitoring profile for the particular health risk of the user. The monitoring engine 144 species a set of health data to capture (e.g., blood sugar levels, weight, blood pressure, calorie consumption, daily step count) through monitoring by the health monitoring devices 102 and their corresponding parameters for monitoring (e.g., a frequency or rate of monitoring, such as monitoring every 10 minutes; a context or condition to trigger a measurement, such as monitoring each time the user operates a particular health monitoring device; a technique for capturing a measurement, such as a particular sensor or particular survey instrument to present). The monitoring engine 144 can also alert the user (e.g., via email, SMS text messages, notification through an application or device) to prompt collection of health data, in case the health monitoring device is unavailable or inoperable. The monitoring engine 144 is described in more detail below, referring FIG. 2.

The system 100 includes the event detection engine 146 that determines a health change event for the particular health risk of the user. The event detection engine 146 receives a set of health data from the health monitoring devices 102 and determines whether a health change event for the particular health risk has occurred for the user. For example, based on receiving the user's recent monitoring results or lifestyle information (e.g., step count measurements or survey results indicating lack of exercise), the event detection engine 146 detects that the user is subject to the increased risk for obesity or type 2 diabetes. The event detection engine 146 is described in more detail below, referring FIGS. 2 and 3.

In some implementations, the system 100 includes a database 148 in communication the server 104 that stores information for use by the application 122, the risk assessment engine 142, the monitoring engine 144, and/or the event detection engine 146. The database 148 can include user information (e.g., identifier of the user), genetic and health risk factors (e.g., to identify a health risk for the user; to be used to build a knowledge graph; described in more detail referring FIG. 5), and monitoring profiles for the user (e.g., instructions used by the health monitoring devices 102 to monitor the user).

In some implementations, the system 100 processes information in the database 148 (e.g., by generating fast-access identifiers or references) such that the access to the information is computationally efficient. For example, the system 100 can apply the filter of a particular user (or a particular health risk) to the database 148 to obtain records associated with the particular user (or a particular health risk). In some implementations, the system 100 optimizes a structure of the database 148 (e.g., a tabular format, a graph format) based on a data processing bandwidth to facilitate load balancing and efficient processing of data.

The techniques discussed herein can be used widely in digital health, digital therapeutics, precision medicine, personalized medicine, precision health. Precision medicine, also called personalized medicine, can involve determining the unique disease risks for an individual and the treatments that will be most effective for an individual. As discussed herein, the system can not only identify or predict the health risks an individual faces, but also characterize the likelihood or severity of those risks. For example, all people many have some non-zero risk of a heart attack, but some factors or combinations of factors can cause the level of risk to vary widely from one individual to the next. The system provides the ability to accurately quantify a risk level that is personalized for an individual, based on the person's unique genome and epigenetic data (e.g., the individual's behavior, environment, etc.), as well as other information such as the current context or situation of the user, the user's medical history, and so on.

Precision health includes precision medicine, and can include interactions that occur outside the setting of a doctor's office or hospital, such as disease prevention and health promotion activities. Precision health involves approaches that everyone can do on their own to protect their health as well as steps that public health systems can take.

Figure 2:
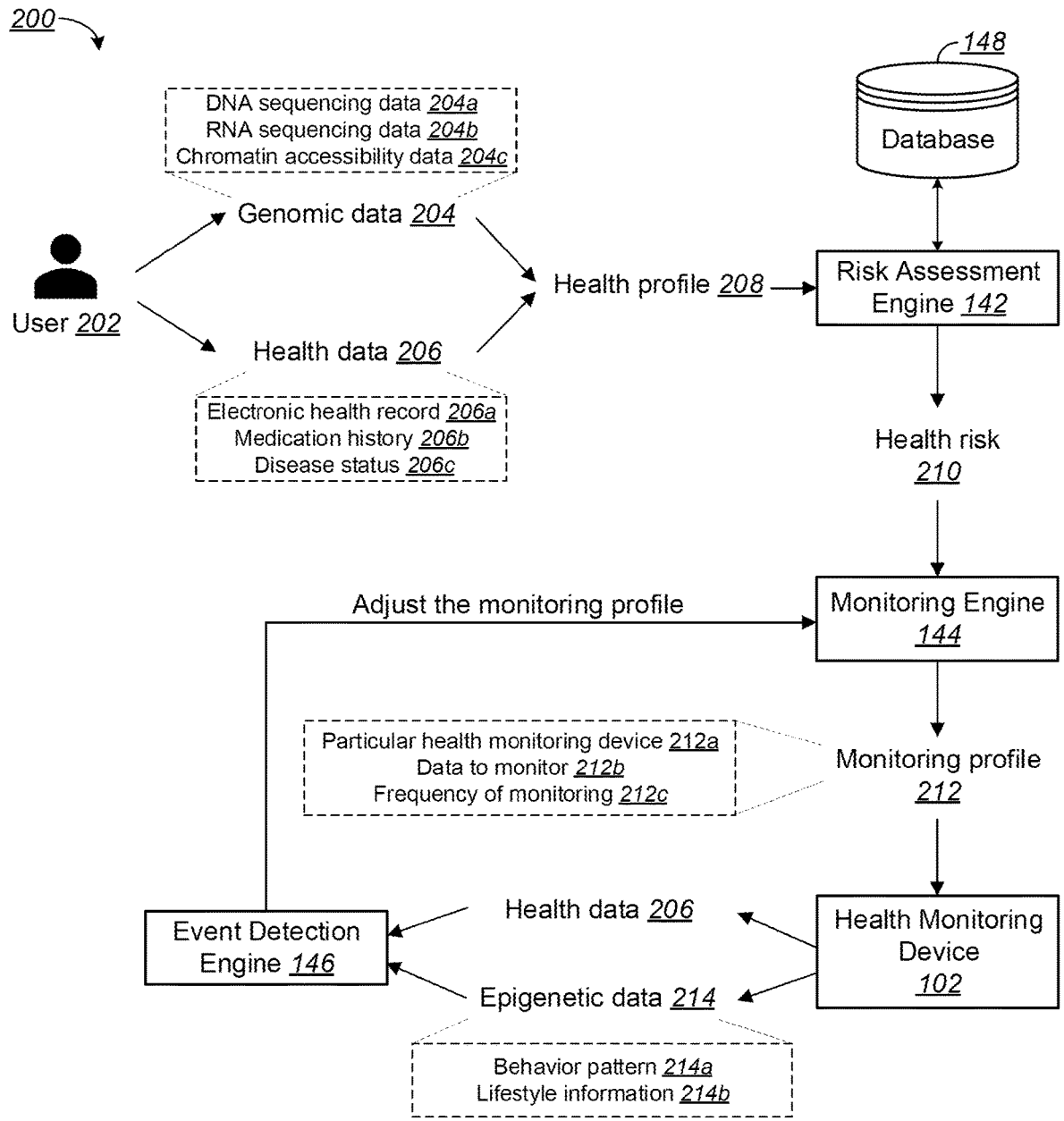
FIG. 2 is an illustration of an example system flow diagram.

FIG. 2 is an illustration of an example system flow diagram 200 of the system 100 of FIG. 1. The risk assessment engine 142 generates a health profile 208 of the user. The health profile 208 represents particular health risks for the user, e.g., increased risk for cardiovascular disease, decreased risk for breast cancer, neutral risk for type 2 diabetes. The health risks are not limited to diseases and include conditions, e.g., increased risk for risky behaviors and increased risk for tobacco usage. The health profile 208 can include a combination of quantitative (80% more likely to smoke than a general population) and qualitative (e.g., increased risk for stroke) health risks. The risk assessment engine 142 determines the health profile 208 based on one or more of genetic data 204 of the user and health data 206 of the user.

The genetic data 204 includes DNA sequencing data 204a (e.g., whole genome sequencing), RNA sequencing data 204b, chromatin accessibility data 204c (e.g., ATAC-seq), and other appropriate 'omic' data types (e.g., proteomics, epigenomics, metabolomics). In some implementations, the genetic data 204 includes quantitative attributes, e.g., the number of risk variants (SNPs) corresponding to a particular disease based on the genome sequencing of the user. In some implementations, the genetic data 204 includes qualitative attributes, e.g., high risk for a particular disease, whether the user genetic data includes a risk gene. As a particular example, in determining qualitative and quantitative attributes, the risk assessment engine 142 uses knowledge from research stored in a standardized format in the database 148. The risk assessment engine 142 can determine which attributes increase/decrease a particular health risk based on the data available in the database 148. The risk assessment engine 142 can also update the database 148 based on incoming data (e.g., discovery of new genetic risk variant) and analysis of other users' genetic data 204 (e.g., performing clustering on the user based on their genotypes and identifying attributes that contribute to the increased/decreased risk of the condition/disease).

In some implementations, the risk assessment engine 142 uses a knowledge graph stored in the database 148 in identifying health risks 210 of the user based on the health profile 208. The knowledge graph aggregates information about which factors increase/decrease each health risk, as well as interactions among health risks. The knowledge graph is described in more detail with reference to FIG. 6.

The health data 206 includes data received from monitoring the user over a time period (e.g., data received from one or more health monitoring devices) and health history data (e.g., electronic health record 206a, medication history 206b, and disease status 206c). For example, the health data 206 can indicate the user's health condition (e.g., hypertension), condition category (e.g., blood pressure), medication (e.g., ACE inhibitor), medication category (e.g., hypertension oral medicine), health provider's note (e.g., a disease prognosis), and physiological attributes (e.g., oxygen level) monitored by the health monitoring devices.

The system 200 includes the monitoring engine 144 that determines a monitoring profile 212 for the particular health risk of the user, based on the health risk 210. The monitoring engine 144 causes the health monitoring devices 102 to monitor the user for a set of health data according to the monitoring profile 212. The monitoring profile 212 includes particular health device 212a, data to monitor 212b, and their corresponding frequency of monitoring 212c. The health data 206 include attributes related to the user's health that can be monitored using a particular health monitoring device, including physiological levels (e.g., temperature). The epigenetic data 214 includes measured of attributes related to the user's behaviors and lifestyle, including a behavioral pattern 214a (e.g., average hours of sleep) and lifestyle information 214b.

The event detection engine 146 receives the health data 206 and the epigenetic data 214 and determines an event, where the event represents a change in the health risk that meets a change threshold. The event detection engine 146 instructs the monitoring engine 144 to adjust the monitoring profile 212. The adjusted monitoring profile can include modifying any of particular health device 212a, data to monitor 212b, and their corresponding frequency of monitoring 212c. For example, upon determining a new type of health data to monitor (e.g., blood pressure level), the monitoring engine 144 can ask the user to link a health monitoring device to collect the new health data. As another example, upon determining an increased risk of existing health risk 210, the monitoring engine 144 can increase the frequency of monitoring 212c. As yet another example, upon determining that the user is no longer at risk for a particular health risk 210, the monitoring engine 144 can remove one or more types of data 212b from monitoring.

In some implementations, the epigenetic data 214 monitored from the health monitoring devices 102 can be used in generating the health profile 208 of the user. For example, the system can determine health risk of obesity after receiving epigenetic data including lack of exercise monitored by the health monitoring device (e.g., average number of steps). Even in the absence of genetic data 204 or the health data 206, the risk assessment engine 142 can generate the health profile 208 of the user, e.g., by imputing unknown parameters by analyzing users with similar attributes among available data.

Figure 3:
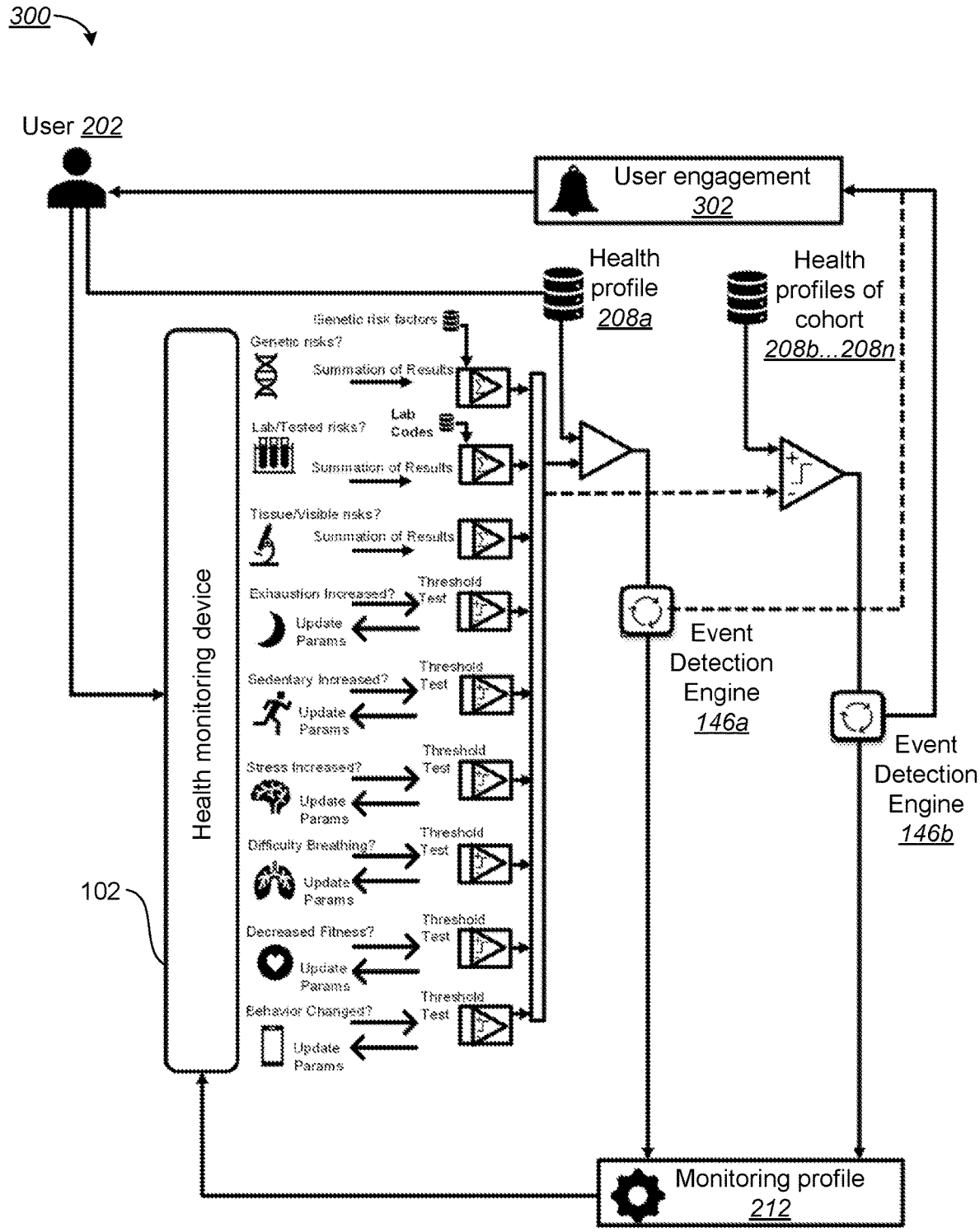
FIG. 3 is an illustration an example monitoring profile adjustment process.

FIG. 3 is an illustration of an example system flow diagram 300 for adjusting monitoring profiles. The flow diagram may be implemented in the system 100 of FIG. 1. The event detection engine 146a detects an event based on data from the health monitoring device 102 and the health profile 208a of the user. The health profile 208a includes the user's health risks. The event detection engine 146a applies a series of threshold tests, each for each of data (e.g., sedentary movement, stress level, difficulty of breathing, decreased fitness, behavior change) monitored from the health monitoring device 102. The event detection engine 146a can apply the threshold test on newly updated genetic and health data including risks identified from the lab and genetic test. Upon detecting the event, the event detection engine 146a adjusts the monitoring profile 212 and sends the adjusted monitoring profile 212 back to the health monitoring device 102. The user 202 is notified by a user engagement 302 system, e.g., a user interface (described in more detail below in reference to FIG. 5A).

The architecture includes an event detection engine 146b that uses health profiles of cohort (multiple users) in determining the event. The event detection engine 146b uses a machine learning model that predicts health risks based on the genetic data, health data, and epigenetic data. The machine learning model trained on health profiles of cohort 208b-208n and their corresponding genetic data, health data, and epigenetic data computes a likelihood of the user 202's health risk based on incoming data monitored by the health monitoring device 102. The machine learning model uses any appropriate machine learning and deep learning training architectures including convolutional neural networks.

Figure 4A:
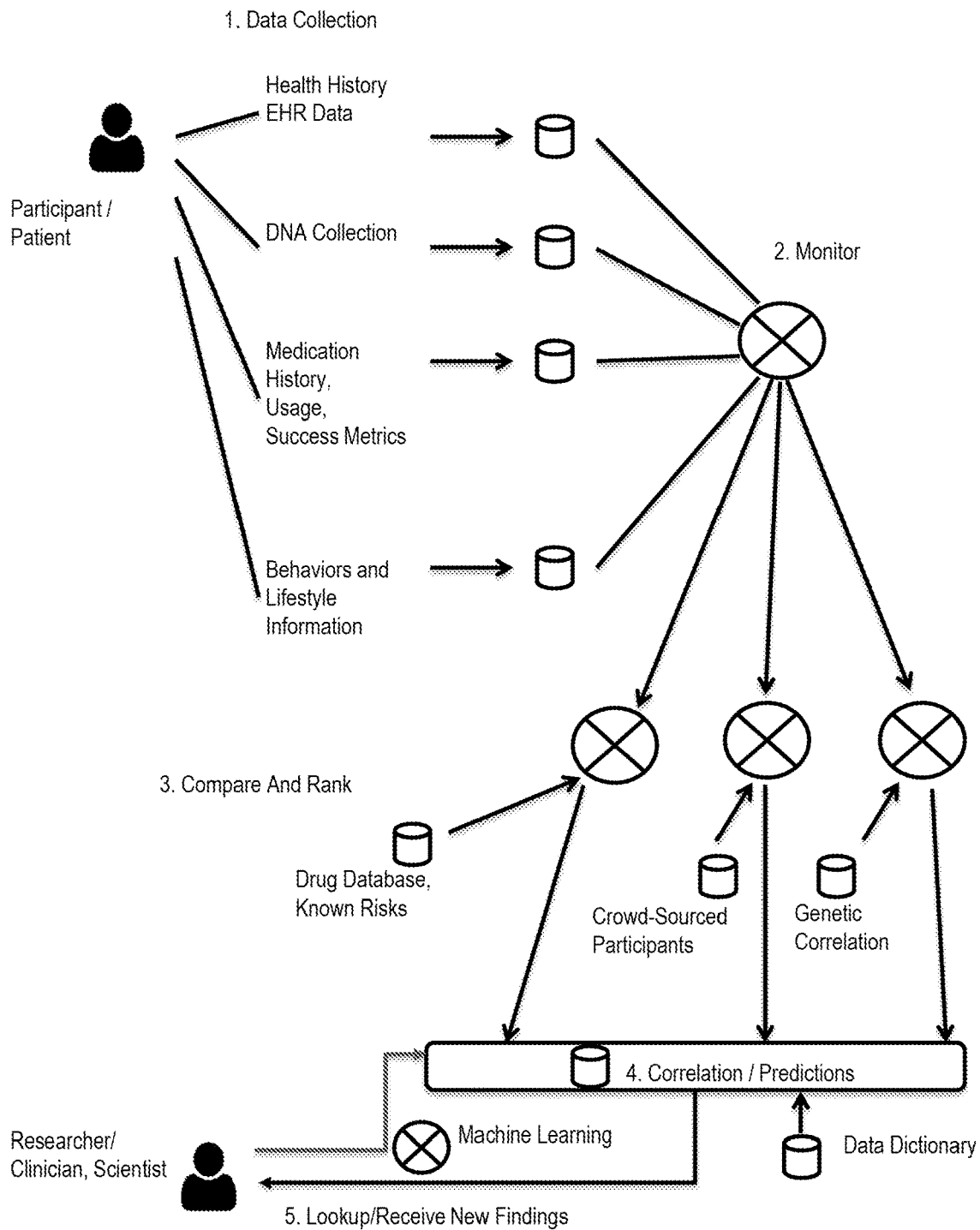
FIG. 4A is a system flow diagram for a data correlation and prediction process.

FIG. 4A is a system flow diagram showing an example of a process 400 for using genetic data and epigenetic data in research and/or healthcare delivery. The flow diagram can be implemented in a system of one or more computers, such as the server 104 interacting with remote health monitoring devices 102a-102n. The implementation of FIG. 4A is an example predictive genetic and epigenetic phenotyping system for evaluating drug indications and risks. In operation, the process 400 has five example phases: (1) data collection; (2) monitoring; (3) data comparison and risk ranking; (4) correlation and predictions; and (5) reporting of new findings.

For data collection, the system collects data for a variety of users across a variety of sources. For example, the users may be subjects of a clinical trial, and the data are collected upon enrollment. These sources may include health history, electronic health records (EHR), behaviors and lifestyles data, genetic samples, and medication history and usage information. Other data not illustrated can also be collected. The data collection results in a health profile for each user. The health profile for the user is based on genetic data of the user and health data of the user describing health aspects of the user. The health profile includes a description of an administration of a drug according to a first administration profile and a first monitoring profile for the user that causes health monitoring devices to monitor the user for a first set of health data according to the first monitoring profile.

The system monitors health data of the user(s). In particular, the process receives, over a time period, for each of the users, a first set of health data from one or more health monitoring devices assigned to the user over the time period, and stores, for each of the users, the first set of monitored health data of the user in the health profile of the user.

The system then compares the health monitoring data and the health profile data and ranks risks and factors. For example, genetic factors and risks as described by genes, gene variants, single nucleotide polymorphisms (SNPs) identifiers and variant attributes may be compared and ranked.

The system then performs determines correlations and makes predictions. For example, drug indications and risks may be evaluated as part of a drug discovery software tool for researchers during a clinical trial. Correlation may include correlation of new findings as new research is regularly released and as updated in drug databases and genetic databases. Accordingly, as knowledge emerges, the knowledge may be readily and quickly incorporated into an ongoing study.

For example, the system (e.g., the server 104) can use identified correlations to nominate potential new drug uses and/or identify potential drug side effects based on an individual's genetic markup. In this example, correlations between monitoring results for individuals and genetic information for the individuals (e.g., whole or partial genome sequencing results) reveal that particular SNPs are significantly associated with a particular drug response (e.g., depression after taking beta-blockers). From correlations of a significant repeatability and magnitude, the system may discover drug-genotype-phenotype relationships that can inform a drug recommendation system based on the individual's genotype and phenotype. The drug recommendation system can predict the individual's drug response, e.g., based on the response to the same drug by other people with similar genotype and phenotype profiles, where similarity is quantified by the system, in some cases using a machine learning approach to predict an appropriate drug or drug administration regimen based on a user's genetic data.

Predictions of the system may be based on a large sample distribution and responses from participants as to the potential for risk based on underlying health, environment, and genetics from a set of crowd-sourced participants.

The reporting phase includes delivering findings to researchers. Such findings may result in adjustment of inclusion or exclusion criteria for participation, notifying participants in case of risk indications, providing interventions to help alleviate risk, and adjusting medication or suggestion new guidance for risk reduction.

Figure 4B:
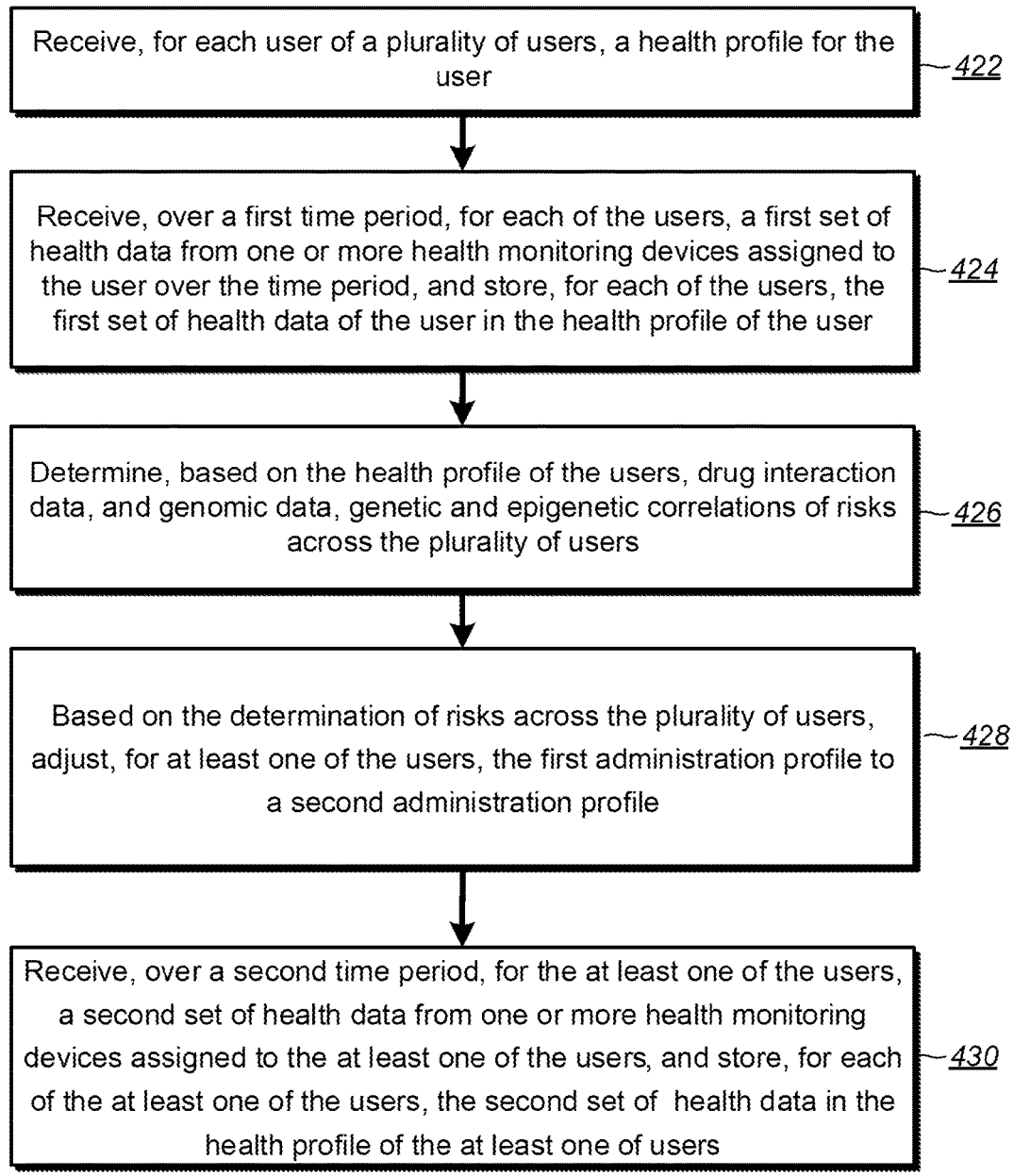
FIG. 4B is a flow diagram of another example process for data correlation and prediction.

FIG. 4B is a flow diagram of another example process 420 that can be used to monitor and adjust how a therapy is administered to an individual or group of individuals. The process 420 will be described as being performed by a system of one or more computers programmed appropriately in accordance with this specification. For example, the process 420 can be performed by the server 104 or other computer system. The process 420 can be used in, for example, a therapeutic setting or in a research setting, such as a clinical trial.

People often have very different responses to medical treatments. For a given set of individuals with the same health condition (e.g., diabetes), the same treatment may produce very different results for some individuals compared to others. A user's genome can have a significant impact on whether a user responds favorably to treatment or not, as well as the magnitude of effect of the treatment in managing disease or improving health, the duration of improvement, how well the treatment is tolerated (e.g., the likelihood and severity of side effects), and other factors. For example, different genetic factors may alter the rate of metabolism of a drug, the relative concentrations in different types of body tissues, and so on. In addition to genetic factors, epigenetic factors provide additional variables that add complexity and alter the likelihood and extent to which a user's genes are expressed. Prior systems have generally failed to account for the interdependence of genetic factors and epigenetic factors on treatment outcomes, both in the administration of treatment as well as the modeling of treatment outcomes. Even when relationships between genes and their corresponding epigenetic factors has been known, prior systems have not used genetic and epigenetic information to customize health monitoring for patients or to identify treatment parameters predicted to improve treatment results.

The present system leverages the identified correlations and modeling showing interaction among genetic and epigenetic factors to dynamically adjust treatment parameters for individuals and groups of individuals. For example, the system can identify epigenetic factors relevant to the respective genotypes of individuals, adjust monitoring to capture information for the epigenetic factors, and use the genetic data and monitoring data for the epigenetic factors to adjust therapy administered over time. The types of therapy that can be provided and adjusted are diverse, such as pharmacotherapy (e.g., administration of drugs, medications, etc.), physical therapy, digital therapeutics, mental health therapy (e.g., cognitive behavioral therapy), and more. The system uses its monitoring capabilities to track patients' responses to treatment (e.g., treatment outcomes, disease symptoms, health status) as well as environmental and behavioral factors that can serve as epigenetic influences for the patients. From the collected data, and genetic data for the patients, the system can characterize how combinations of genetic and epigenetic factors affect the success of different therapies, as well as how these combinations interact with specific treatment variables (e.g., frequency of treatment delivery, dosage of medication or interaction, duration that treatment continues, and so on). For example, the system can generate data in a database, set of rules, or machine learning model to store the relationships between genetic and epigenetic factors together on the effectiveness or efficacy of different treatments or treatment parameters in preventing, managing, or treating a disease.

As the system monitors additional patients, the system can use the generated information about genetic and epigenetic factors on treatment outcomes to adjust treatment for individuals or groups of individuals. For example, the database, rules, or machine learning model indicates, for each of different genetic profiles (e.g., gene variants, combinations of genes, etc.), the epigenetic factors that have the strongest influence on the success of a particular therapy (e.g., a blood pressure lowering medication) for individuals with that genetic profile. For patients that are provided the particular therapy, the system can use genetic data for each patient to determine which genetic profile or genetic category the user fits in (e.g., whether the user has gene variant 1, gene variant 2, etc.).

The system can then customize monitoring for each individual to capture data for the set of epigenetic factors that has the highest influence on treatment success for the characteristics of his or her genetic data. With the most impactful epigenetic influences tracked by the system for each patient, the system can also fine-tune the administration of the therapy. For example, in the example, of the blood pressure lowering medication, the system may have extracted from monitoring data of various individuals that, for patients with a particular gene variant, the effect on lowering blood pressure of the particular medication is strongly influenced by daily physical activity levels (e.g., more effective with at least moderate exercise, but lower effectiveness with low exercise) and air quality levels (e.g., higher effectiveness with lower particulate concentrations). Given this, for patients receiving the medication and which have the particular gene variant, the system can adjust the patient's device(s) to monitor physical activity (e.g., accelerometer data, step count) and to obtain air quality data (e.g., by connecting to an air quality monitor in the user's home, or using GPS location data to determine the user's location and retrieving air quality for the user's location from a third-party database). For individuals whose monitored activity level is low, the system can make further changes to adjust the administration of therapy for the user, such as to add digital therapeutic interactions to cause the patient to increase physical activity, or to indicate that increased dosage is needed to account for the lower effectiveness for patients with low physical activity. Similarly, if air quality is determined to be low, the system can recommend changes to the therapy to make it more robust against (e.g., less sensitive to) the effect of poor air quality (e.g., changing the timing or frequency of administration, changing the drug, etc.) or by causing interactions to improve air quality (e.g., instruct the user to open or close a window, causing an air purifier to increase its duty cycle, etc.).

In this process, the system assesses monitored results of the therapy, e.g., measured blood pressure in this example, to measure the effect of the therapy and determine whether the therapy is reaching or improving toward a health goal or target state of health. When treatment is not achieving the desired effect, however, the individual's genetic data and epigenetic data enable the system to determine how to improve the effectiveness of therapy for the patient. This can include altering the therapy provided in order to provide therapy calculated or predicted by the system to be more effective given the measures for epigenetic factors for the patient. For example, given monitoring data indicating low physical activity of a patient, the system can determine to change the regimen for the medication (e.g., change frequency, dosage, or other parameters), or change to a different drug, that has been observed to be less sensitive to or to provide better results in the context of low physical activity.

In addition or as an alternative, the system can address detected low effectiveness by interacting with the patient to change the status of the patient with respect to the epigenetic factors known to be relevant to the patient's genotype and the treatment effectiveness. For example, the strongest epigenetic factors indicated by the database, rules, or models indicate the areas where a patient can make changes to have the greatest impact on improving treatment results. In the example of the blood pressure medication, the system can identify air quality as a strong epigenetic factor (e.g., having at least a minimum threshold correlation or score for influence on treatment outcome; being among the highest-ranked set of environmental or behavioral factors, such as in the top 3, top 5, top 10, etc.) for the success of therapy on the genetic characteristics of the patient. When monitoring shows poor air quality (e.g., high particulate levels) and treatment does not achieve desired results, the system can identify improvement in air quality has having a high likelihood or magnitude of influence in increasing treatment success (e.g., lowering blood pressure).

As the system dynamically adjusts the items monitored for patients and the treatment parameters, the system monitors responses to treatment to generate treatment response data. Collectively, this data shows examples the impact of many combinations of genetic factors and epigenetic factors on many different variations in treatment regimens. With this data, the system updates its database, rules, and models that show relationships among genetic factors, epigenetic factors, and treatment parameters for addressing various health risks of diseases. The system can use the treatment interaction data to periodically or continually update its data and its models to identify new combinations of genetic and epigenetic factors that affect treatment parameters, adjust the strength or magnitude of correlations between epigenetic factors and treatment parameters (e.g., adjusting ranking or prioritization of different epigenetic factors for different therapies), and so on. This process can include machine learning training, where information about various specific examples of monitoring are used to generate feature vector input to a machine learning model, and the parameters of the model are incrementally and iteratively adjusted so the model more accurately makes predictions. The models can be trained to predict the outcomes of treatment given input of epigenetic and genetic data of an individual, or to predict the set of epigenetic factors for an individual for a particular treatment given input of genetic data for the individual. Models can be generated for specific treatments and/or health risks or health conditions. Alternatively, combined models can include information about multiple treatments and/or health risks or health conditions, and a value identifying the treatment and/or health risk or health condition of interest can be provided as an input to the model when training or making predictions.

With the information gained through the process, the system can determine which individuals with a health risk or disease are indicated for different treatments. With the information about epigenetic and genetic factors together, this enables the system to inform physicians, drug companies, and others about which treatments or treatment parameters are most appropriate (e.g., most likely to be effective, have the fewest or least severe side effects, act most quickly, etc.) based on both genetic characteristics and environmental and behavioral characteristics. For example, one drug may be identified as highly effective for patients with a particular gene variant, but only for where certain epigenetic factors fall in certain thresholds or ranges. As a result, the system can learn, from monitoring of users in different situations and across different variations of treatment, that the drug is indicated for patients with the particular gene variant as long as sleep duration and air quality levels meet corresponding threshold, but that the drug is not indicated (or that different administration parameters are needed) when sleep duration is lower than the threshold and/or when air quality levels are worse than the threshold level. The system can perform the monitoring and incremental adjustments to treatment in clinical trials or in clinical treatment settings, and can produce rules, models, and other outputs based on the treatment responses monitored for users with different combinations of genetic and epigenetic factors present.

The process 420 includes receiving, for each user of a plurality of users, a health profile for the user (422). The process 420 can involve monitoring and potentially adjusting treatment for each individual in a group. For example, the group can be a set of participants in a cohort of a clinical trial or another research study. As another example, the group may be a subset of the cohort for a research study or a sub-study of a research study. The group may also be a set of similarly situated patients, such as those that have a health condition or health risk in common (e.g., patients with type 2 diabetes, a group of cancer survivors that were previously diagnosed with leukemia, etc.). The group of individuals may be, but is not required to be, a group selected out of a larger pool based on the individual sharing certain genetic characteristics in common.

The health profile for each user can be based on genetic data of the user and health data of the user describing health aspects of the user. The health profile can include an indication of or description of a therapy that is or has been administered to the user. For example, the health profile can indicate administration of a drug according to a first administration profile. The administration profile can indicate various aspects about the treatment regimen used, e.g., timing of interventions, frequency of interventions, dose or intensity of therapy, goals or targets for therapy, administration route (e.g., for a drug, oral, topical, etc.), and so on. In addition, the health profile can indicate a monitoring scheme applied for the user, such as characteristics of a first monitoring profile for the user that causes one or more health monitoring devices to monitor the user to collect a first set of health data according to the first monitoring profile.

The health profile can store information about the current health status of the user and in some cases also health history for the user. The health profile can be describe any of various aspects of health, such as nutrition, sleep, exercise, medications, drug use, relationships, mental health, and more. The health profile includes information the system uses to evaluate the user's risks of acquiring diseases or other health conditions. The health profile can be generated by compiling information from various sources to describe characteristics such as the demographic characteristics, physiological state, behavior, mental health, medical history, or other aspects of health. For example, to generate the health profile, the system may obtain health data from one or more sources (e.g., an enrollment survey, EHR data, mobile device data, physician visit records, insurance records, medical history survey, etc.) and may convert or map the data to standardized data fields or to a predefined data schema for a database for storing health data. The health profile can store health data for the individual, as well as determinations that the system makes based on the health data (e.g., a likelihood or risk category for a disease, an indication of health conditions stated in or inferred from health data, etc.).

The health profile can be based on genetic data of the user. For example, from the genetic data, the system can identify genetic characteristics of the user that make the user more susceptible to or more resistant to different diseases or health conditions. As discussed above, the genetic data can provide various types of information about the genome of the user to indicate aspects of the genotype of the user. The genetic data can describe various types of genomic characteristics, such as including gene sequences (e.g., partial or whole genome sequencing results), indicating gene variants or SNPs present in the user's genome, indicating classifications or categories determined based on the user's genome, and so on.

The health profile may include indicators of health risks derived from the genetic data. For example, the system may store records that indicate different health conditions (e.g., heart attack, stroke, CVT, DVT, diabetes, lung cancer, etc.) and associate those health conditions with corresponding genomic characteristics (e.g., particular gene variants, particular SNPs, combinations of alleles, etc.) that affect the development of the health conditions. The records can indicate the strength of the relationship between health conditions and genomic characteristics (e.g., scores or statistics indicating how likely the genetic characteristics are to lead to the health condition), to capture the varying level of influence that genetic characteristics have on different health conditions. The relationships indicated in the records can be sourced from medical research databases, such as gene-disease databases such as The Online Mendelian Inheritance in Man (OMIM) database, the Ensembl genome database project, and the Gene Disease Associations Database (DisGeNET). The system may also mine records of longitudinal health studies that have genetic data for the subjects studied so that the system may identify correlations that indicate or at least suggest interactions of genes with specific health conditions.

The health profile can also be generated based on health data of the user captured through monitoring the user's health over a time period. For example, a user upon enrollment in a health management program, treatment program, or clinical trial may be instructed to begin health monitoring with a general (e.g., basic or default) or default monitoring procedure that captures a set of physiological and behavioral health indicators using surveys, sensors, and other techniques. Health data can be captured by and reported back to the system from one or more health monitoring devices (e.g., phone, watch, activity tracker, glucometer, weight scale, etc.) over an initial time period (e.g., a week, a month, etc.). This can provide the information to establish or confirm the current state of health of the user and to establish baseline measures for the user's physiological attributes, behaviors, environment, and so on.

The process 420 includes receiving, over a time period, for each of the users, a first set of health data from one or more health monitoring devices for the user over the time period (424). For example, during an initial period of treatment or during an initial period of a clinical trial, the users in the group can each be monitored using their respective devices, e.g., smart phones, smart watches, glucometer, weight scale, etc. The users in the group can each receive treatment interventions (e.g., behavioral, pharmacological, device-based interactions, etc.) according to a first administration profile, which can be stored in the health profiles, in study protocol data, or other records. The treatment regimen specified by the first administration profile can be the same for each of the users in the group. The first set of health data can thus include data describing the state of health of the individual during and after treatment according to the first administration profile. The first set of health data for each user can thus indicate the response to treatment (e.g., monitoring results at various times before and after a treatment dose is given to show changes in physiology or behavior, if any, after a treatment dose is given). The health data can also include monitoring results for epigenetic factors for genetic characteristics of the users.

The devices of users can perform monitoring according to a monitoring profile, which may be a the same for the members of the group or may be different for different individuals. For example, the monitoring profile may specify data collection to perform to meet the requirements of a study protocol for a research study for which the users in the group are participants. As another example, the monitoring profile may specify monitoring parameters indicating measurements for different epigenetic factors determined for individuals (or groups that share genetic features in common) based on genetic data. The monitoring profile may additionally or alternatively include instructions and parameters to cause monitoring of indicators of a health condition or health risk (e.g., to indicate the severity of disease, to detect whether a disease or other outcome has occurred), to monitor whether treatment occurs (e.g., to monitor compliance with a study protocol), and to monitor indicators of the effectiveness of therapy that was, is, or will be provided. For each of the users, the system can store the first set of health data for that user in the user's health profile.

The health data may include any of the various items discussed for monitoring herein, such as environmental data (e.g., measures or indicators of ambient temperature, light levels, sound levels, air quality, etc.), behavioral data (e.g., measures or indicators of movement, exercise, sleep, social activity, etc.), physiological state (e.g., blood pressure, heart rate, body weight, body temperature, blood glucose level, etc.), and more. Nevertheless, the monitoring performed is generally performed selectively, according to the study protocol for a study or the nature of the health condition or health risk being monitored.

The process 420 includes determining genetic and epigenetic correlations of risks across the plurality of users, based on the health profile of the users, interaction data, and genetic data (426). The system can determine health risks and characteristics of the health risks (e.g., likelihood of occurrence, predicted magnitude or severity, etc.) for each user. These risks can be risks of adverse health events (e.g., stroke, heart attack, etc.), worsening of a disease, acquiring a disease, a decrease in a physiological or behavioral measure, risk that treatment may be or become ineffective, etc. To characterize the health risks, the system can correlate multiple factors across multiple users to identify components that influence the risks, and the system can determine relative weightings of the factors identified from analysis of data for users in the group and/or other groups.

For example, the process 420 performs genome-wide association studies (GWAS) on a first cohort with a particular disease and a second cohort without the particular disease. In this example, GWAS utilizes genotypes and phenotypes of the first and second cohorts to identify disease-associated SNPs. The disease-associated SNPs, when present in a user's genome, can be used as indicators of a health risk for a user, e.g., increased risk for schizophrenia based on having numerous numbers of schizophrenia-associated SNPs.

As a second example, the process 420 can use each user's medication usage (e.g., type of mediation, dosage) to identify a relationship between the drug and the user's genotype. In this example, the process 420 performs pharmacogenetics analysis to identify drug response-associated SNPs. The drug response-associated SNPs can inform a choice of a particular drug based on the user's genotype and/or can predict the user's side effect when a particular drug is administrated.

In some implementations, the system evaluates the risks or likelihoods that treatment will be successful in meeting a goal or target for the health of the user, given the user's genetic and epigenetic data and the known or predicted influence of these factors on the effectiveness of the therapy defined in the first administration profile. In some implementations, the system uses the epigenetic and genetic data to evaluate the potential for additional health risks that may occur, whether as a result of the therapy being provided (e.g., medication side effects) or separately.

As discussed above, the system can use the therapeutic interaction data (e.g., monitoring data indicating the level of response of individuals to the treatment provided) in combination with genetic data and health data to determine how different epigenetic factors and genetic factors work together to influence the likelihood and degree of success of treatments. For example, although each of the users in the group may have the same underlying health risk or health condition and may receive treatment according to the same treatment administration profile, the responses to treatment (e.g., the health outcomes or phenotypes observed) may various significantly based on both differences in the genomes of the users and differences in values for epigenetic factors (e.g., differences in behavior and environment) for the users.

To facilitate the identification of health risks, the system may store records that indicate different health conditions (e.g., heart attack, stroke, CVT, DVT, diabetes, lung cancer, etc.) and associate those health conditions with corresponding genetic characteristics (e.g., particular gene variants, particular SNPs, combinations of alleles occurring together, etc.) that affect the development of the health conditions. The records can indicate the strength of the relationship between health conditions and genomic characteristics (e.g., scores or statistics indicating how likely the genetic characteristics are to lead to the health condition), to capture the varying level of influence that genetic characteristics have on different health conditions. The relationships indicated in the records can be sourced from medical research databases, such as gene-disease databases such as The Online Mendelian Inheritance in Man (OMIM) database, the Ensembl genome database project, and the Gene Disease Associations Database (DisGeNET). The system may also mine records of longitudinal health studies that have genetic data for the subjects studied so that the system may identify correlations that indicate or at least suggest interactions of genes with specific health conditions.

In some implementations, the system compares data in the health profile of the user with data specifying risk factors for different health risks (e.g., obesity, substance abuse, different diseases, impaired mental health, etc.). For each health risk, the system can aggregate or combine the contribution of different risk factors to determine the overall risk for a user for a particular health outcome. This can include taking into account genetic features or values for epigenetic factors that either increase or decrease a user's level of risk compared to the risk at a population or group level.

The system can store reference statistics or models (including predictive machine learning models) for different health risks, which enabling the system to (1) identify the attributes that affect different health risks, and (2) use values for those attributes, as specified in the health profile, to calculate scores or other measured for the risks. For example, the system can generate likelihood scores for each of various health conditions as well as scores for the potential severity or impact on the user if the health condition were to occur. The system can then assign a risk level or risk category to the different actual or potential health conditions for the user, based on the likelihood, severity, and other measures calculated. For health conditions that meet at least a minimum threshold risk level, by having at least a minimum likelihood and/or predicted severity, the system can determine that assessment and monitoring for the health condition is needed. The system may determine the health risks of a user at various points in time, including doing so repeatedly over time to dynamically adjust which health risks are assessed and monitored for by the system.

As an example, for individuals monitored for risk of stroke, increased blood pressure may be known to be a contributing factor generally (e.g., regardless of the user's genome). Nevertheless, the system can interpret a moderately high blood pressure level (e.g., 130/90) differently depending on the genomic characteristics of the individual. For some sets of genetic features, this may represent a low risk (e.g., +5% compared to an average blood pressure level). When certain genetic features are present, however, the system can determine that the same moderately high blood pressure may present a higher risk (e.g., +50%). As discussed above, the actual risk level may be determined from statistical analysis or machine learning analysis of data sets showing heath data, genetic data, and health outcomes for many individuals, enabling the system to determine how, when certain genetic features are present, certain environmental and behavioral attributes (or values or ranges of those attributes) have an outsized impact on risk, and so can be identified as epigenetic factors of particular relevance to specific genes, gene variants, SNPs, combinations of genetic features, etc.

In some implementations, the system identifies a health risk based on the health data for other individuals. For example, the system can have data describing longitudinal tracking of health status and health outcomes for individuals, or may have more discrete "snapshots" of health data indicating health status and outcomes at discrete times. From these records, the system can identify the ranges of values and combinations of values for different attributes that correspond to the current presence of, or future development of, different health conditions. For example, the system can identify individuals that have had a heart attack, and from records for these individuals determine the sets of attribute values that have been present for the individuals prior to a heart attack, by an amount of 1 month, 1 year, 5 years, or another time period. The system can determine the averages and distributions for these sets of attribute values, and then compare the similarity of the user's attributes (as stated in the health profile) with the composite or aggregate information about health states that preceded heart attacks. When the user's health profile has at least a minimum level of similarity, the user can be identified has having a sufficient level of heart attack risk to justify further monitoring and analysis of the health risk for the user.

In some implementations, the system receives a set of health profiles of other users and information about the health conditions of those other users. The system can compare the health profile of the user with health profiles of the other users, and can identify a particular health risk for the user based on the comparison. For example, the system can perform clustering based on similarity of various aspects in the health profiles, and can determine health conditions that indicated in profiles for users in the cluster. The user can be inferred by the system to have a health risk of developing a health condition indicated by the profiles of other users in the same cluster that the user's health profile is assigned.

In some implementations, the system stores machine learning models that have been trained to predict the likelihood of an individual developing a health condition. These models can be trained based on examples of individuals that did develop a health condition and individuals that did not develop the health condition. Once the model has been trained, the system provides data derived from the health profile as input (e.g., a vector of feature scores for a defined set of input features) to the machine learning model trained to determine a health risk based on the input. The system receives, as output of the trained machine learning model, data indicating the likelihood of the particular health risk for the user, such as a probability value, classification and confidence score, and so on.

The machine learning system can be trained on a subset of users' health profiles to predict health risks, e.g., using supervised machine learning to make predictions. The machine learning model can learn relationships between health profiles and health risks during training. For example, the model can learn to predict health risks associated with a certain combinations of genetic data, health data, and/or epigenetic data.

The machine learning models discussed herein can be, for example, neural networks or classifiers. Other types of models that may be used include support vector machines, regression models, reinforcement learning models, clustering models, decision trees, random forest models, genetic algorithms, Bayesian models, and Gaussian mixture models. Different types of models can be used together as an ensemble or for making different types of predictions. Other types of models can be used, even if they are not of the machine learning type. For example, statistical models and rule-based models can be used.

The system can analyze the examples in a database to determine relationships (e.g., between health attributes and likelihoods of health conditions, between genomic characteristics and likelihood of health conditions, between behavioral and environmental factors and genomic characteristics, etc.), either through explicit analysis or through machine learning training, e.g., so that a model implicitly learns the predictive value of different data items on current or future readiness. Training can incrementally or iteratively update the values of parameters in the models to learn the impact of different factors on predicted outputs. In the case of neural networks, backpropagation can be used to alter neural network weights for neurons or nodes at various layers of the neural network model.

The process 420 includes adjusting the first administration profile to a second administration profile for at least one of the users based on the determination of risks across the plurality of users (428). This can involve personalizing therapy for an individual in the group, a subset of the group that includes only a part of the group, or for the group as a whole. The second administration profile is different from the first administration profile, and so indicates changed therapy being administered. For example, the second administration profile can change the schedule for taking drug can be changed, the dosage or formulation of the drug can be changed, a second drug may be recommended to be taken with the first drug, a second drug may be used in place of the first drug, and so on. In some cases, the administration profiles automatically change the provision of medical treatment to an individual, for example, by changing digital therapeutic interventions provided by devices, altering administration of a pharmaceutical by a drug delivery device, etc.

As an example, after the members of the group (e.g., a cohort of a clinical trial) each receive a medication or other therapy for a first time period (e.g., a week), the system may review daily monitoring data provided by the devices of the users. The survey responses of user and the sensor data shows how the users have tolerated the drug, if there are any indications of toxicity (e.g., large increases in heart rate, behavioral changes, etc.), and the level of effectiveness of the therapy. The monitoring data also includes information about the context of the users, their environments, and their behaviors. From the data collected, the system evaluates health risks for the different users. The system may determine that for one subset of users, treatment is effective and may be continued unchanged. For a second subset of users, however, the system may determine that treatment is not effective and should be adjusted to increase the likelihood of effectively managing a risk or disease of the users. The actual adjustments the system determines for users may vary according to the different genetic features and epigenetic features, as well as their respective responses to treatment.

For example, within the second subset of users, one subgroup that showed positive but insufficient response to therapy may have the administration profile changed to increase dosage. A second subgroup for which the treatment was not effective may have a genetic characteristic and/or measured environmental factor that indicates that an increased dose would increase a health risk or is unlikely to be effective, requiring a different change to the administration of the therapy. The system may determine that for a third subset of users, the collected data indicates a new or increased health risk, which may or may not be related to the effectiveness of the therapy being provided. For example, even if treatment is effective for some users, the system may determine that the genetic and epigenetic factors together result in a high risk (or increased risk since the beginning of the period) of a serious side effect, and so the administration of therapy can be changed to reduce the risk of the side effect (e.g., to reduce dosage, to add a drug to mitigate the likelihood of the side effect, to add a behavioral or environmental change to the therapy, etc.).

Optionally, the first monitoring profile for one or more users may be adjusted to a second monitoring profile for the user. In the case of a monitoring profile, the one or more health monitoring devices change from monitoring the user for a first set of health data to monitoring the user to collect second types of health data. For example, the second monitoring profile may cause health data to be monitored by the health monitoring devices more frequently or less frequently than directed by the first monitoring profile, resulting in larger or smaller sets of health data. Alternatively, different types of health data may be monitored by the health monitoring devices. Other changes in monitoring can also be made.

The process 420 can include receiving, over a second time period, for the at least one of the users, a second set of health data from one or more health monitoring devices for the at least one of the users (430). For example, after the parameters of therapy are changed for at least some users in the group, the system continues monitoring to determine the effectiveness of the therapy with the changes to the administration of the therapy. The system stores, for each of the at least one of the users, the second set of health data in the health profile of the at least one of users. The second set of health data is health data that is associated with the second administration profile, so the system can use the monitoring results received to update the records and models characterizing the effectiveness of the treatment variation as well as to identify the genetic and epigenetic features that cause a user to be indicated or contraindicated for the updated version of the therapy.

This enables the system to discern whether the second administration profile is effective (or ineffective) for its intended objective. For example, the second administration profile may be based on a person's particular genetics and phenotype, and the objective may be to reduce (or preclude) a high blood pressure side effect resulting from a particular drug. While the data monitored during the second time period may be the same as the data monitored during the first time period, the data monitored during the second time period may be flagged, based on the time of the second administration profile, to be evaluated or compared to other data to determine the efficacy of the second administration profile.

As discussed above, the process 420 can include monitoring of users to generate health data, e.g., to monitor health status generally, to detect response (or lack of response) of the patient to therapy provided, to detect when and if therapy was actually provided (e.g., to track medication adherence, compliance with a treatment regimen, etc.), and to monitor the status of different epigenetic factors selected by the system as relevant to the effectiveness of therapy provided and/or to the health condition or health risk of the user. To perform this monitoring, and also to adjust the monitoring, the system may techniques as described with respect to the process 700 shown in FIG. 7 and described below. For example, the process 420 may include any or all of the steps of the process 700, or may use at least some of the techniques described to carry out one or more of the steps of the process 420.

The techniques described herein can enable pharmaceutical companies to develop more targeted or more precise drugs. The techniques enable researchers and clinicians to detect how individuals with different combinations of genetic and epigenetic factors. The data sets generated by the system allow a drug developer to tailor drug formulations and/or administration regimens for different subgroups or populations. For example, the developer can use the information learned by the system and the monitoring results generated by the system to determine that, for user having certain genetic features, a certain drug formulation, dosage, or administration regimen is most effective. Further, the data sets can demonstrate that even among individuals with a particular genetic feature (e.g., a certain gene variant), different formulations, dosages, or administration parameters are preferred when certain epigenetic factors are present (e.g., differences in environment, behavior, etc.). As a result, one regimen or dosage can be determined to be more effective for users having the combination of a particular genetic profile and certain habits (e.g., high exercise and moderate sleep levels), where another regimen or dosage is more effective for users with other habits (e.g., moderate exercise and low sleep levels).

The system enables adjustment to the administration profile for a therapy, which can include medication, for people with certain epigenetic and/or genetic characteristics. The system can use what is observed about risks and interactions of genetic and epigenetic factors with treatment parameters to generate specific profiles for different types of user and different situations. In the context of pharmaceuticals, the different administration profiles can have differences in the formulations, dosages, schedules for administration, combinations of drugs used, medication interactions to avoid, indications or contraindications, and more. More generally, the administration profiles can correspond to differing levels of effectiveness overall.

The techniques discussed can enable pharmaceutical companies to prove better efficacy of their drugs, with increased evidence of how well a therapy is working as well as the specific genetic and epigenetic contexts where a therapy is most effective. In a similar manner, the system enables a physician, consumer, or other health care provider be able to determine or assess efficacy of treatment in the same manner.

In some implementations, the administration profile directs administration of digital therapeutics. Digital therapeutics can deliver medical interventions directly to patients using evidence-based software to treat, manage, and prevent a broad spectrum of diseases and disorders. These techniques can deliver therapies using smartphones, tablets, wearable devices, and other devices, which increases patient access to clinically safe and effective therapies. Digital therapeutics have been shown to be effective in treating a variety of medical conditions, such as anxiety, depression, ADHD, insomnia, substance abuse, obesity, hypertension, and more. Similarly, digital therapeutics can assist user in managing diseases such as diabetes, cancer, heart disease, chronic obstructive pulmonary disease (COPD), and so on. Digital therapeutics are also provided as a preventive measure for patients who are at risk of developing more serious conditions. For example, a patient with prediabetes may be prescribed digital therapeutics as a method to change their diet and behavior that could otherwise lead to a diabetes diagnosis.

Digital therapeutics interventions can include various interactions, including those made remotely through a smartphone or other user device. In many cases, the interactions can be initiated automatically by software on a user device or by a server system sending instructions to cause the user device to provide the interactions. As a result, digital therapeutics can be provided automatically, without a user having to manually open an application and seek out interaction. In many instances, digital therapeutics and other health care programs can operate in an "always on" manner, initiating interactions automatically based on a schedule, based on the context of a user device, or based on detected conditions or triggers (e.g., sensor measures or user inputs that indicate predetermined indicators or markers for certain behaviors, situations, physiological characteristics, and so on).

As a few examples of interactions made through digital therapeutics, the system can inform a user of a health risk, provide media, generate an interactive form such as a survey, provide a test or assessment, send a notification message, provide recommendations, provide content from a social media platform, provide instructional activities or games, and so on. In some cases, the system can prompt a user to set, adjust, or view a goal, or challenge, remind, or inform the user about a goal. Similarly, the system may prompt a user to take an action, record a measurement from a device, provide content for a user to read or view, initiate a challenge for a user to change behavior (or to perform a specific action or task). The system may communicate with family of a user, friends of a user, or others regarding a user's goals or status, including with health service providers. In general, interactions may involve visual output, audio output, haptic output, typed or touchscreen input, voice input, gesture input, and other input/output modalities. The media provided as part of the interactions can include content such as text, videos, audio segments, images, interactive instructional materials, messages (e.g., indicating encouragement, reminders, etc.), games, and other content.

To make better predictions and provide more accurate diagnostic and treatment recommendations, the system can provide interventions that prompt users to complete an assessment at specific times during the day or in response to specific situations or contexts. Examples include ecological momentary assessments (EMA). The system can also support passive ascertainment of changes in clinical status, in behavior, or in other aspects. The system can be configured to behavioral support, such as self-management strategies, immediately following assessments or detection of triggering conditions. The approaches to data collection and treatment can be highly personalized. The system can tailor or personalize digital health interventions based on each individual's characteristics (e.g., race, gender, socio-economic status, etc.) for disease prevention, presentation, management, and outcomes and that ultimately contribute to a more individualized approach to health care.

The system can be used to monitor the effectiveness of treatment of the user and adjust treatment accordingly. For example, if provided digital therapeutics do not result in the expected or desired improvements in physiological attributes or user behaviors, the server 104 can select and provide different digital therapeutics interventions. As another example, if medications provided do not yield the desired effects, or if the collected data indicates that there are problematic side effects, the server 104 can recommend changes to the medication regimen, such as changing the dose, type of medication, frequency or timing of administration, and so on. In making treatment decisions and recommendations, the server 104 can use data indicating medical research results and best practices, for example, to provide actions based on clinically validated and evidence-based treatment steps that can be captured in rules, look-up tables, databases, or other data structures.

Figure 4C:
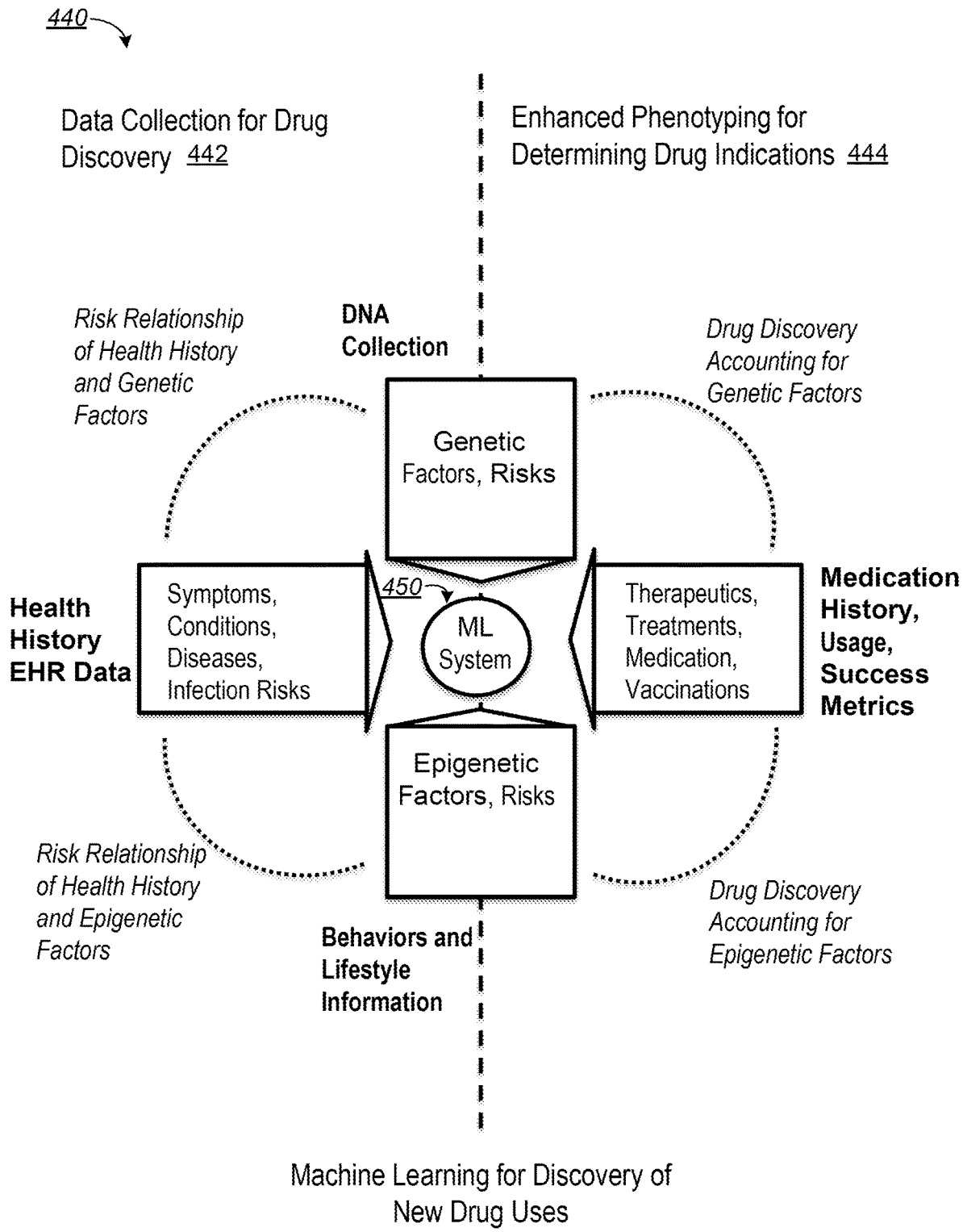
FIG. 4C is a machine learning system architecture.

FIG. 4C is a machine learning system architecture 440 for a machine learning system 450. The machine learning system 450 implements machine learning for discovery of new drug uses (e.g., drug repositioning). In some implementations, the architecture 440 creates a relationship between the data collection and the discoveries made and provides training data from the collected information into a machine learning system 450. Any appropriate machine learning model may be used, e.g., a deep learning neural network, a convolutional neural network, etc.

The circular relationship model has two primary components, the left side, which represents the data collection for drug discovery 442, and the right side, which represents the enhanced phenotyping for determining drug indications 444. For example, information from learned sources, e.g., the National Library of Medicine, may be catalogued and correlated in a database for comparing health reported information and epigenetic data. The relationship between the DNA collection and health history across a population and research is modeled within the databases and overall architecture of the system. As more information is collected about a participant's behaviors and lifecycles, an epigenetic relationship is made between the health history, and furthermore the genetic/DNA collection. As data is collected about the medication history, drug discovery is then mapped back to both the genetic and epigenetic factors/risks that have been identified.

By way of a further example, consider the gene SERPINC1 in the context of a vaccine. The gene is single nucleotide polymorphism (SNP) rs2227589. The presence of this gene provides an increased risk of Cerebral Venous Thrombosis (CVT), which occurs in the cerebral venous sinuses and blocks drainage of blood thereby creating a thrombus or clot that can result in a stroke or death. Two components describe a thrombus, the fibrin or protein that creates a chain to help trap the red blood cells and platelets that create mass. Where arteries are responsible for carrying oxygen from the heart to the body, veins return the blood back to the heart for reoxygenation. A thrombus can occur in both arteries and veins, and while fibrin has significance typically in veins, platelets have significance in arteries.

Based on the type of thrombus, there are two classifiers that describe antithrombotic drugs: anticoagulants and antiplatelets. Examples of anticoagulants are Heparin, Warfarin, Apixaban, Dabigatran, Edoxaban, Enoxaparin, and Rivaroaxaban; examples of antiplatelets are Aspirin, Ticlopidine, Prasugrel, Clopidogrel, and Ticagrelor.

Antithrombotic therapy plans have reduced the risk of blood clots in deep-vein thrombosis (DVT) patients and the risk of death from heart attacks, and has made surgery possible for bypass surgery and dialysis by blocking clotting in external tubing.

Antiplatelets can increase risk of bleeding. Alternatives when considering anti-hypertension or high blood pressure risks might be to use alpha-blockers that reduce nerve impulses causing vessels to tighten, or Angiotensin-Converting Enzymes (ACE) inhibitors which reducing the bodies hormone development of Angiotensin II allowing blood vessels to remain more relaxed. ACE inhibitors also have side effects, such as coughing, which Angiotensin II receptor blockers (ARBs) can be used to block the effect of the angiotensin II hormone. While the impact of anti-hypertension medication will not replace antithrombotic drugs, adjustments to care plan may be required based on newly introduced medications where an anti-hypertension medication may need to be replaced for an alternative medication when considering antiplatelets for instance.

Fibrin counts can be a type of marker in many areas of the body related to cancer treatments in determining whether the cancer treatment is working. Additionally, in rheumatoid arthritis, fibrins play a role with their interaction with inflammatory cells.

Accordingly, classification of these risk factors for thromboembolisms is comprised of Genetic and Epigenetic components: genetic risk factors and epigenetic risk factors. Genetic risk factors include ntithrombin (gene: SERPINC1), Protein C and Protein S, Coagulation factor V Leiden, Prothrombin gene (coagulation factor II), Factor XIII These risk factors are determined from DNA analysis.

Epigenetic risk factors (e.g., environmental/behavior/acquired phenotypic changes) for SERPINC1 and associated CVT risk include age, immobilization, surgery/trauma, travel distance, cancer, oral contraceptives, hormone replacement therapy, pregnancy, and the like. In other words, the values for these types of data can significantly increase or decrease the risk level for a person with the SERPINC1 SNP. For a person without SERPINC1, limited or restricted movement for a day may have a negligible effect on likelihood of developing CVT. However, for a person with SERPINC1, the same limited or restricted movement for a day may result in a much greater risk, potentially rising to dangerous levels if other factors (e.g., age, presence of other chronic conditions) are accounted for. Given the relationship between these factors and the risks of SERPINC1, these factors are determined to be epigenetic factors that can be monitored for individuals that have the SERPINC1 sequence to assess CVT risk.

Additionally, Serpin Family C Member 1 (SERPINC1) encodes the protein antithrombin III. This protein inhibits thrombin. Mutations of this gene are known to cause antithrombin-III deficiency and create a strong risk factor for thrombosis. Severe cases of COVID-19 are associated with a reduction of this protein. This may also be the primary risk factor for individuals that are susceptible to CVT during vaccination. Nevertheless, even individuals that each have SERPINC1 face different levels of risk depending on their environment, behaviors, and physiological state, and so the epigenetic data, e.g., monitoring results for the epigenetic factors for SERPINC1, is important in providing an accurate, personalized risk level that the system can use to adjust monitoring and treatment for the individual.

Figure 4D:
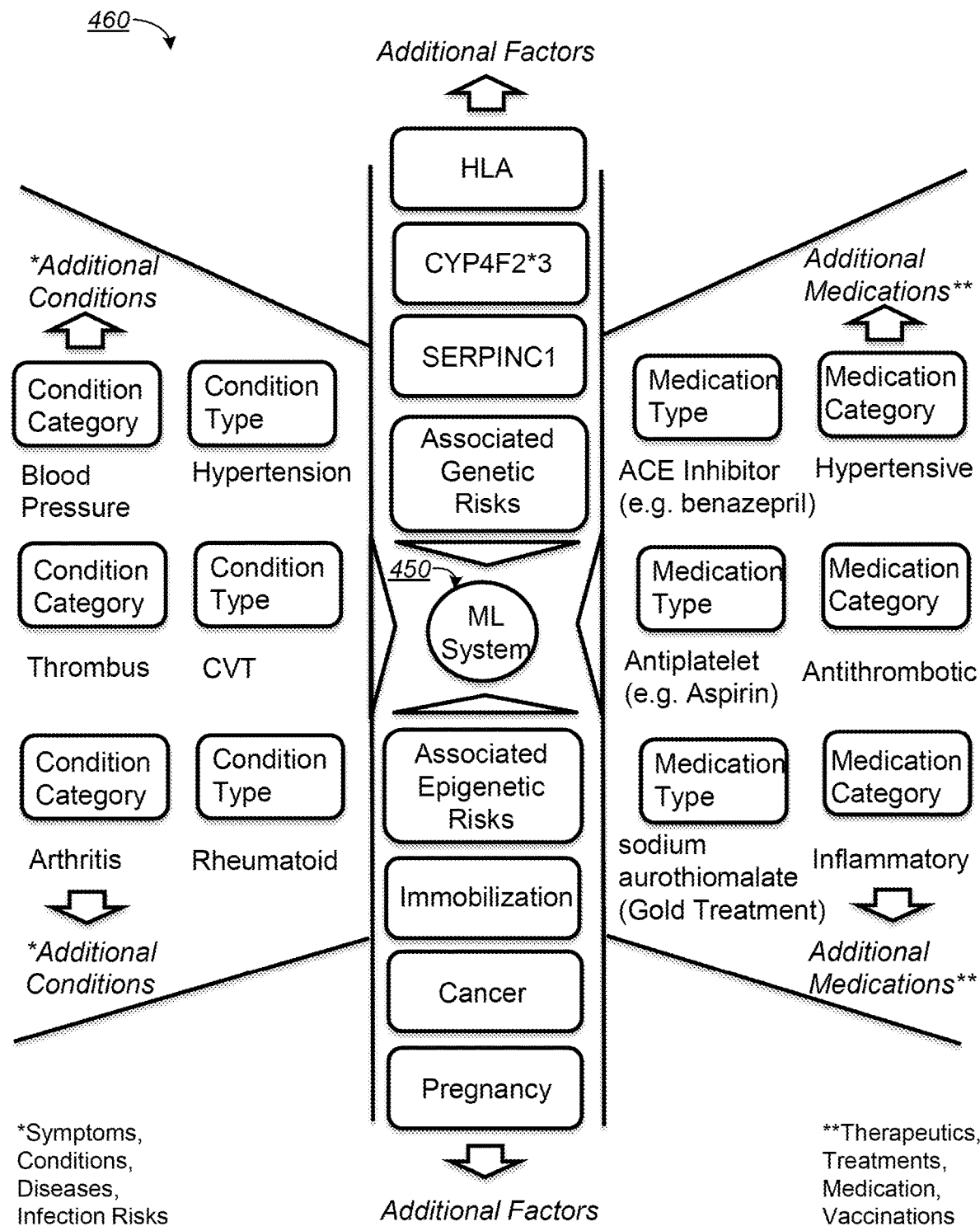
FIG. 4D is an example set of inputs for the system architecture of FIG. 4C.

Applying this information to the architecture 440, a set of inputs for the machine learning system 450 can be derived. One such example set of inputs is illustrated in FIG. 4D. Genetic and epigenetic factors are show as the inputs above and below the machine learning system 450, respectively. To left side inputs relate to symptoms, conditions, disease and infection risks, and the right side inputs relate to therapeutics, treatments, medications and vaccinations.

Figure 5A:
FIG. 5A is an illustration of a user interface showing an adjustment to an administration profile.

Using the machine learning system 450, a researcher or health care provider can identify links in the information collected or in the execution of the research study. For instance, as an exemplary embodiment, the researcher analyzes the current drug category, treatment category, indications, to find a drug that will help manage the risks associated. In doing this, the researcher identifies a risk for a COVID-19 vaccination that can cause thrombocytopenia, and for some patients depending on health history and genetic correlation with associated risks, may be prescribed aspirin as a suitable drug. Patients can be then notified, treatments adjusted, or inclusion/exclusion can change their participation in each study. For example, as shown in FIG. 5A, a user interface may display the findings, and an adjustment to an administration profile. The user interface 500 of FIG. 5A surfaces inferences made by the machine learning system 450 about interactions among the genetic data, health data, and epigenetic data. For example, given the healthcare providers' specification of 'Reduced Risk' interaction for risks 'TTS' (thrombocytopenia with thrombosis syndrome), the user interface 500 displays a summary report including a potential correction of risk of TTS with Aspirin, which is a change to an administration profile by adding an additional drug to be taken by the patient or subject. The healthcare providers can schedule an appointment with a particular patient or subject via the user interface 500 and organize treatment plans.

Figure 5B:
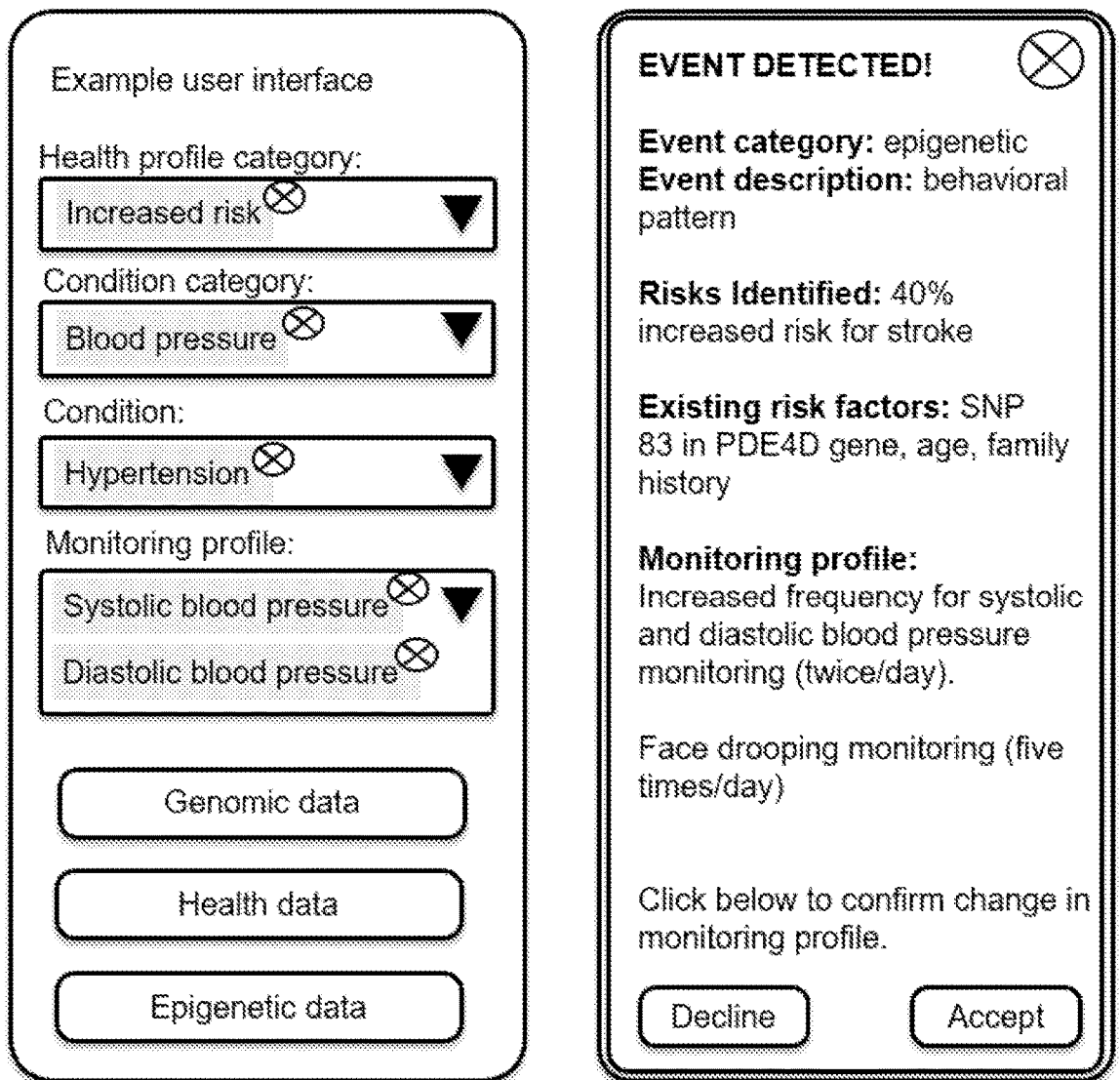
FIG. 5B is an illustration of a user interface showing an adjustment to a monitoring profile.

FIG. 5B show another example user interface 550, which shows an adjustment to a monitoring profile. The user interface 550 displays a health profile category (e.g., increased risk), a condition category (e.g., blood pressure), and a condition (e.g., hypertension) where the user specifies a health risk, and a monitoring profile (e.g., systolic and diastolic blood pressure). The monitoring profile can also include corresponding health monitoring devices 102 that monitor each health data. The user interface 500 includes 'Genetic data', 'Health data', and 'Epigenetic data' user selectable elements, where the user can view summary of their genetic data, health data, and epigenetic data on the user interface. For example, upon determining that the user selects the 'Epigenetic data' user selectable element, the user interface 550 displays the graph of systolic blood pressure monitored over a specified period, e.g., past 2 weeks.

The user interface 550 can display information about detected event including event category (e.g., epigenetic), event description (e.g., behavioral pattern), risks identified (e.g., 40% increased risk for stroke), existing risk factors (e.g., SNP 83 in PDE4D gene, age, family history), and a new monitoring profile (e.g., increased frequency for systolic and diastolic blood pressure monitoring to twice daily). The new monitoring profile can include monitoring health data that were previously not monitored, e.g., face drooping monitoring in this case. The user can decline or accept the new monitoring profile on the user interface 550, e.g., by selecting 'Decline' or 'Accept' user selectable elements. In some implementations, the system (e.g., the monitoring engine 144) bypasses the user's permission and applies the new monitoring profile. In some implementations, the event detection engine 146 alerts the user for the detected event via the user interface 550.

Figure 6:
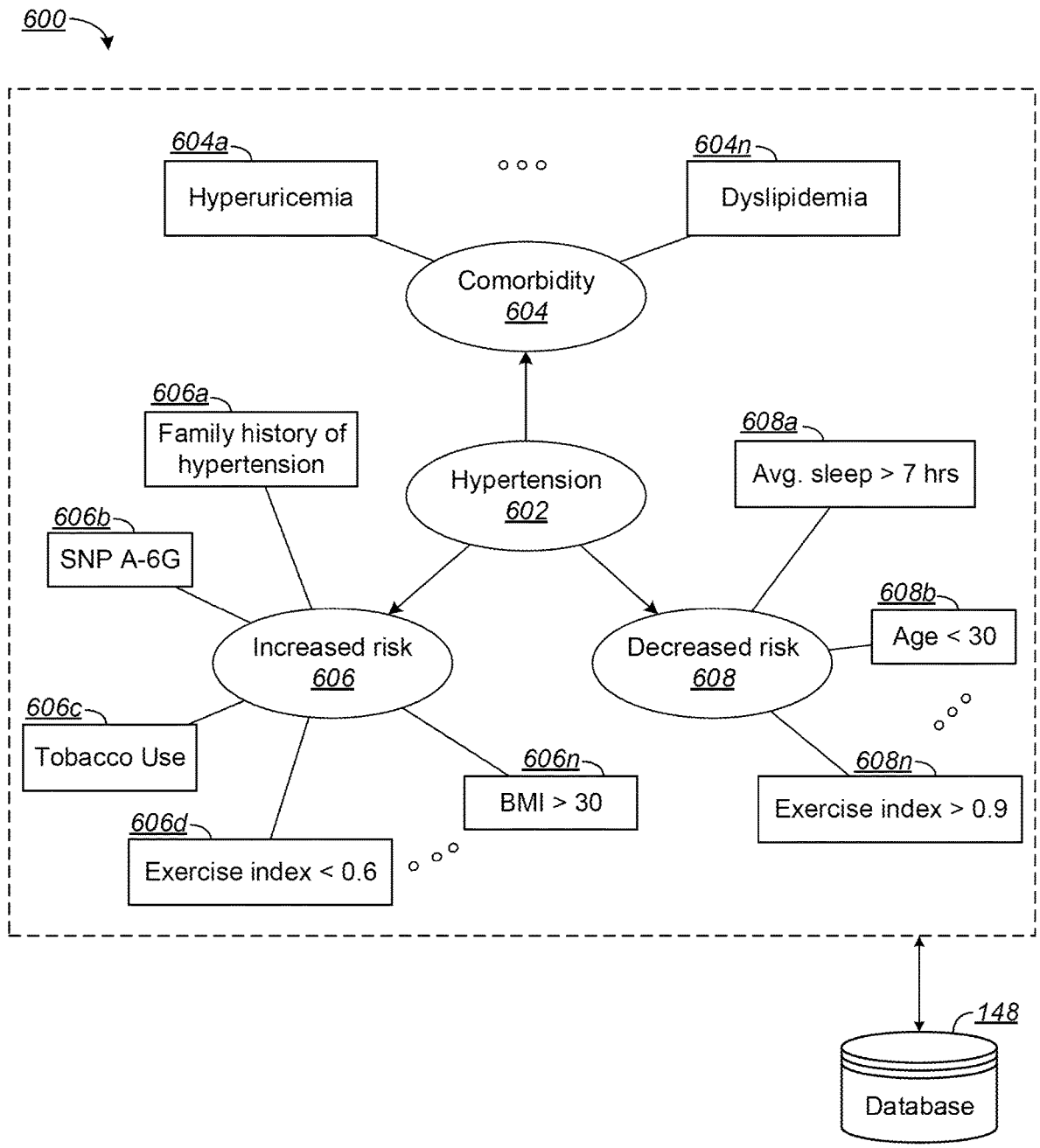
FIG. 6 is an illustration an example knowledge graph.

In other implementations, a knowledge graph can be used instead, or in additional to, a machine learning system. FIG. 6 shows an example knowledge graph 600. The system 100 can generate the knowledge graph 600 based on the genetic data, the health data, and the epigenetic data of users. The knowledge graph is a set of tuples that specify nodes connected by relations. The knowledge graph 600 includes a health risk node 602 (e.g., hypertension) connected by a node representing comorbidity and nodes representing factors increasing or decreasing the health risk. The comorbidity node 604 includes conditions/diseases linked to the health risk node 602, e.g., hyperuricemia 604a to dyslipidemia 604n. The increased risk node 606 includes factors 606a-606n that contribute to the increased risk of the health risk (e.g., in this case, hypertension). The decreased risk node 608 includes factors 608a-608n that contribute to the decreased risk of the health risk. The system can learn adequate thresholds to use for each factor to classify into the increased risk and the decreased risk. For example, the system determines that age less than 30 is linked to decreased risk for hypertension, based on scientific findings (e.g., literature support). While discrete categories are shown for increased or decreased risk, in some implementations, the system quantifies the risk at a granular level (e.g., with a score or percentage, such as 40% increased risk for hypertension; or with a category of risk, such as high, medium, low, etc.). For example, the system can combine how many of risk factors the user has and determines the risk based on the weighted average (e.g., equal weighting of factors 606a-606n). The knowledge graph 600 can be stored in the database 148 or a separate database other than the database 148.

Figure 7:
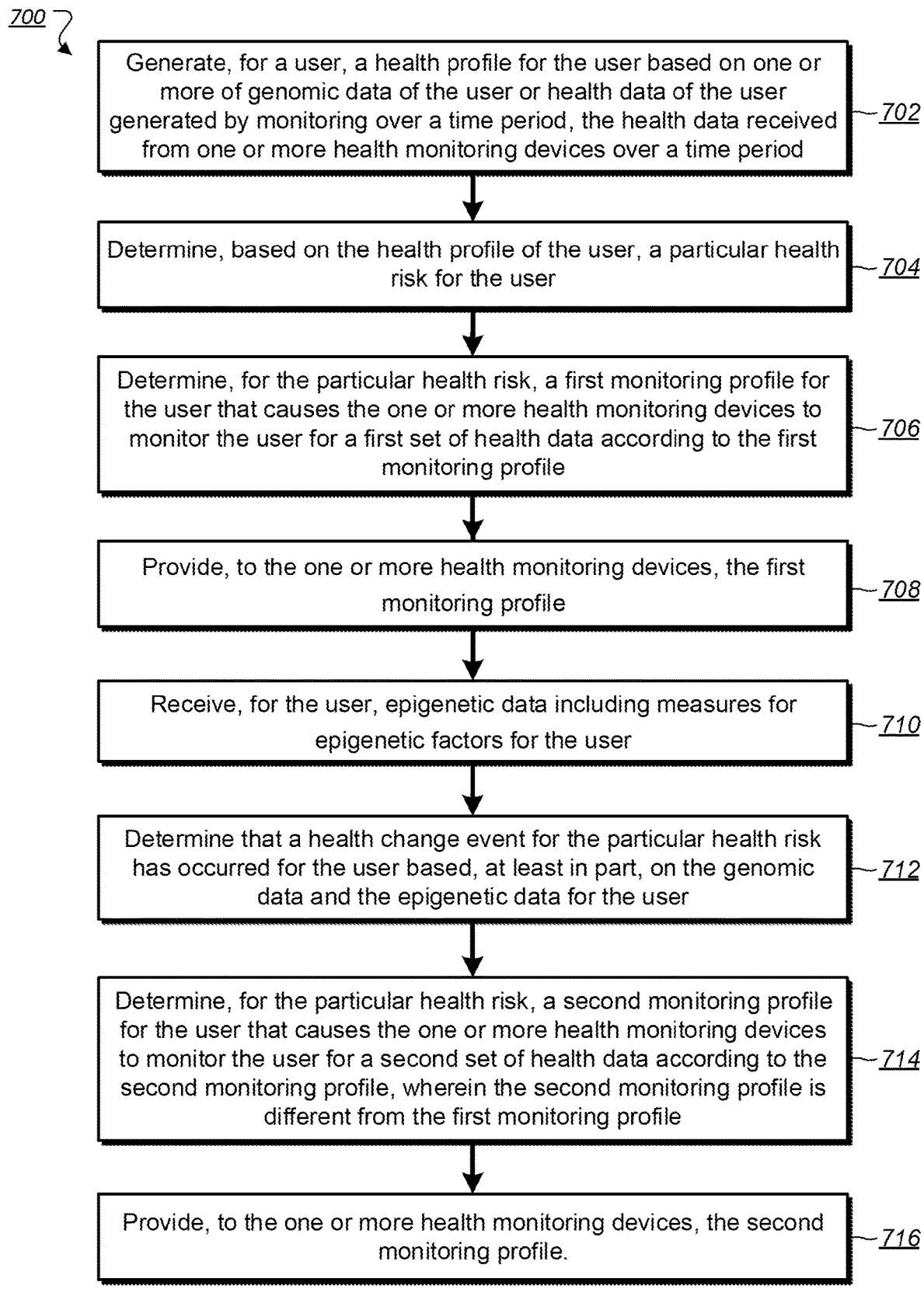
FIG. 7 is a flow diagram of an example process of adjusting end device monitoring profiles.

FIG. 7 is a flowchart of an example process 700 for customizing monitoring at end devices using genetic data and epigenetic data. The process will be described as being performed by a system of one or more computers programmed appropriately in accordance with this specification. For example, the system 100 of FIG. 1 can perform at least a portion of the example process.

The system generates a health profile for the user (702). The health profile can store information about the current health status of the user and in some cases also health history for the user. In some implementations, the health profile is a repository of health information about a specific individual. The health profile can be describe any of various aspects of health, such as nutrition, sleep, exercise, medications, drug use, relationships, mental health, and more. The health profile includes information the system uses to evaluate the user's risks of acquiring diseases or other health conditions. The health profile can be generated by compiling information from various sources to describe characteristics such as the demographic characteristics, physiological state, behavior, mental health, medical history, or other aspects of health. For example, to generate the health profile, the system may obtain health data from one or more sources (e.g., an enrollment survey, EHR data, mobile device data, physician visit records, insurance records, medical history survey, etc.) and may convert or map the data to standardized data fields or to a predefined data schema for a database for storing health data. The health profile can store health data for the individual, as well as determinations that the system makes based on the health data (e.g., a likelihood or risk category for a disease, an indication of health conditions stated in or inferred from health data, etc.).

The health profile can be based on genetic data of the user. For example, from the genetic data, the system can identify genetic characteristics of the user that make the user more susceptible to or more resistant to different diseases or health conditions. As discussed above, the genetic data can provide various types of information about the genome of the user to indicate aspects of the genotype of the user. The genetic data can describe various types of genome characteristics, such as including gene sequences (e.g., partial or whole genome sequencing results), indicating gene variants or SNPs present in the user's genome, indicating classifications or categories determined based on the user's genome, and so on.

The health profile may include indicators of health risks derived from the genetic data. For example, the system may store records that indicate different health conditions (e.g., heart attack, stroke, CVT, DVT, diabetes, lung cancer, etc.) and associate those health conditions with corresponding genome characteristics (e.g., particular gene variants, particular SNPs, combinations of alleles, etc.) that affect the development of the health conditions. The records can indicate the strength of the relationship between health conditions and genome characteristics (e.g., scores or statistics indicating how likely the genetic characteristics are to lead to the health condition), to capture the varying level of influence that genetic characteristics have on different health conditions. The relationships indicated in the records can be sourced from medical research databases, such as gene-disease databases such as The Online Mendelian Inheritance in Man (OMIM) database, the Ensembl genome database project, and the Gene Disease Associations Database (DisGeNET). The system may also mine records of longitudinal health studies that have genetic data for the subjects studied so that the system may identify correlations that indicate or at least suggest interactions of genes with specific health conditions.

The health profile can also be generated based on health data of the user captured through monitoring the user's health over a time period. For example, a user upon enrollment in a health management program, treatment program, or clinical trial may be instructed to begin health monitoring with a general (e.g., basic or default) or default monitoring procedure that captures a set of physiological and behavioral health indicators using surveys, sensors, and other techniques. Health data can be captured by and reported back to the system from one or more health monitoring devices (e.g., phone, watch, activity tracker, glucometer, weight scale, etc.) over an initial time period (e.g., a week, a month, etc.). This can provide the information to establish or confirm the current state of health of the user and to establish baseline measures for the user's physiological attributes, behaviors, environment, and so on.

The system determines, based on the health profile of the user, a particular health risk for the user (704). In some implementations, the system compares data in the health profile of the user with data specifying risk factors for different health risks (e.g., obesity, substance abuse, different diseases, impaired mental health, etc.). The system can store reference statistics or models (including predictive machine learning models) for different health risks, which enabling the system to (1) identify the attributes that affect different health risks, and (2) use values for those attributes, as specified in the health profile, to calculate scores or other measured for the risks. For example, the system can generate likelihood scores for each of various health conditions as well as scores for the potential severity or impact on the user if the health condition were to occur. The system can then assign a risk level or risk category to the different actual or potential health conditions for the user, based on the likelihood, severity, and other measures calculated. For health conditions that meet at least a minimum threshold risk level, by having at least a minimum likelihood and/or predicted severity, the system can determine that assessment and monitoring for the health condition is needed. The system may determine the health risks of a user at various points in time, including doing so repeatedly over time to dynamically adjust which health risks are assessed and monitored for by the system.

In some cases, the system may be able to derive a health risk for the user directly from the health profile. The system may use stored rules to identify the presence of some health conditions. Many health risks or risks or certain health conditions, or even the current presence of some health conditions, can be identified through rules that evaluate the data in specific fields or areas of a health profile. For example, the health profile may indicate height and weight of the user, and based on a simple calculation of body mass index, the system can determine whether the user is overweight and thus whether this presents a health risk. Similarly, in some cases, a user may be diagnosed diabetes or cancer, and this condition may be indicated in the health profile. Indeed, in some cases, the system supports prevention, management, or treatment for a specific health condition, such as diabetes or heart disease, so the user is known to or can be assumed to have a particular health risk.

In some implementations, the system identifies a health risk based on the health data for other individuals. For example, the system can have data describing longitudinal tracking of health status and health outcomes for individuals, or may have more discrete "snapshots" of health data indicating health status and outcomes at discrete times. From these records, the system can identify the ranges of values and combinations of values for different attributes that correspond to the current presence of, or future development of, different health conditions. For example, the system can identify individuals that have had a heart attack, and from records for these individuals determine the sets of attribute values that have been present for the individuals prior to a heart attack, by an amount of 1 month, 1 year, 5 years, or another time period. The system can determine the averages and distributions for these sets of attribute values, and then compare the similarity of the user's attributes (as stated in the health profile) with the composite or aggregate information about health states that preceded heart attacks. When the user's health profile has at least a minimum level of similarity, the user can be identified has having a sufficient level of heart attack risk to justify further monitoring and analysis of the health risk for the user.

In some implementations, the system receives a set of health profiles of other users and information about the health conditions of those other users. The system can compare the health profile of the user with health profiles of the other users, and can identify a particular health risk for the user based on the comparison. For example, the system can perform clustering based on similarity of various aspects in the health profiles, and can determine health conditions that indicated in profiles for users in the cluster. The user can be inferred by the system to have a health risk of developing a health condition indicated by the profiles of other users in the same cluster that the user's health profile is assigned.

In some implementations, the system stores machine learning models that have been trained to predict the likelihood of an individual developing a health condition. These models can be trained based on examples of individuals that did develop a health condition and individuals that did not develop the health condition. Once the model has been trained, the system provides data derived from the health profile as input (e.g., a vector of feature scores for a defined set of input features) to the machine learning model trained to determine a health risk based on the input. The system receives, as output of the trained machine learning model, data indicating the likelihood of the particular health risk for the user, such as a probability value, classification and confidence score, and so on.

The machine learning system can be trained on a subset of users' health profiles to predict health risks, e.g., using supervised machine learning to make predictions. The machine learning model can learn relationships between health profiles and health risks during training. For example, the model can learn to predict health risks associated with a certain combinations of genetic data, health data, and/or epigenetic data.

The machine learning models discussed herein can be, for example, neural networks or classifiers. Other types of models that may be used include support vector machines, regression models, reinforcement learning models, clustering models, decision trees, random forest models, genetic algorithms, Bayesian models, and Gaussian mixture models. Different types of models can be used together as an ensemble or for making different types of predictions. Other types of models can be used, even if they are not of the machine learning type. For example, statistical models and rule-based models can be used.

The system can analyze the examples in a database to determine relationships (e.g., between health attributes and likelihoods of health conditions, between genome characteristics and likelihood of health conditions, between behavioral and environmental factors and genome characteristics, etc.), either through explicit analysis or through machine learning training, e.g., so that a model implicitly learns the predictive value of different data items on current or future readiness. Training can incrementally or iteratively update the values of parameters in the models to learn the impact of different factors on predicted outputs. In the case of neural networks, backpropagation can be used to alter neural network weights for neurons or nodes at various layers of the neural network model.

The system determines, for the particular health risk, a first monitoring profile for the user that causes the one or more health monitoring devices to monitor the user to generate first set of health data according to the first monitoring profile (706). A monitoring profile specifies various parameters that set how a health monitoring device performs monitoring. As discussed above, the health monitoring device can be a computing device such as a smart phone or smart watch or a medical device such as a glucometer. A monitoring profile can be configured to cause a device to automatically perform the monitoring specified, for example, to perform repeated measurements on a periodic or scheduled basis, or in a context-driven manner as the device detects certain contexts occurring. The health monitoring device can have an application installed that is configured to receive and interpret monitoring profiles, and to carry out the monitoring directed by the monitoring profile. To direct the monitoring performed by an end device, a monitoring profile may include parameter values, configuration data for hardware or software, instructions, and/or rules for directing actions by the device (e.g., conditioning actions on the device detecting certain factors or patterns). In some cases, the monitoring profile may include or may link to software modules or executable code that can be run by a receiving device to configure the device to perform the monitoring desired.

The first monitoring profile can be, but is not required to be, the initial monitoring profile used to monitor data for the health risk for the user. Accordingly, the first monitoring profile may be a generalized or default monitoring profile for the health risk. Alternatively, the first monitoring profile may be one provided after one or more prior monitoring profiles have been provided, potentially even profiles for monitoring the same health risk. In this case, the first monitoring profile may represent one monitoring scheme in a series of various monitoring schemes that have been used for the user, and the first monitoring program may represent an incremental adjustment or adaptation to a prior monitoring scheme for the user.

In some implementations, the first monitoring program is selected to or is generated to cause monitoring of items that the server 104 has selected as epigenetic factors corresponding to genome characteristics of the user. In other words, the first set of health data can represent measurements for a set of items that the server 104 selects for the user based on the user's genetic data and the server's records indicating epigenetic factors for the genome characteristics of the user. For example, the system can use the genetic data for the user to identify genes, gene variants, SNPs, or other genome characteristics of the user that relate to (e.g., affect the likelihood or severity of) the health risk. Then, for each of the various relevant genome characteristics identified, the system can compile a list of factors that alter the risk level for individuals that have the genome characteristic. These can be epigenetic factors that have been confirmed through research to cause epigenetic changes or those that have been predicted to or suspected to influence the health risk in the presence of the genome characteristics (e.g., based on correlations identified or machine learning modeling based on data sets involving various individuals genetic data and health outcomes). The system can filter the identified factors to limit the set of items to be monitored to those having the greatest impact on the health risk. For example, the server 104 can apply thresholds to scores for the factors that indicate the magnitude of effect the factors have, to retain only factors that, according to statistical data or machine learning models, have at least a minimum level of effect on the health risk for individuals having the identified genome characteristics. The system combines the epigenetic factors determined for the genome characteristics identified as relevant, to obtain a set of epigenetic factors to be monitored for the user. The system can combine this set of epigenetic factors with general monitoring factors for the health risk (e.g., a general base level of monitoring for the health risk, regardless of a user's genome), to obtain a first set of data types to be monitored. The first monitoring profile is then generated, or selected from among a set of predetermined monitoring profiles, so that it causes a device to capture and return health data for that first set of data types.

In addition to selecting the types of data to monitor, the system can also adjust other parameters of monitoring based on the user's genetic data. For example, the relative impact of the identified epigenetic factors for the user on the health risk can be used to adjust the frequency or precision of monitoring. For a particular SNP of the user, the system may identify two epigenetic factors, such as physical activity level and sleep quality level. For these factors, there can be various levels of intensity or frequency of monitoring. For example, physical activity and sleep could be assessed with a weekly survey with one question each, a daily survey, a more detailed daily survey. Similarly, different sensor measurements could be used, e.g., using step count from a single device (e.g., phone), from multiple devices (e.g., phone and smart watch), using accelerometer data over time, monitoring hourly step count, and so on. Depending on the severity of the health risk for the user (e.g., an overall risk score or risk category for the user)—and/or based on the strength of correlation between the different factors and the particular SNP and/or the health risk—the system can select from among the different monitoring levels for the identified factors. As a result, even for two individuals being monitored for the same health risk and the same general type of data (e.g., physical activity and sleep quality), the system can customize the monitoring profiles so that the monitoring technique (e.g., survey, sensors, or both), frequency of monitoring, precision or granularity of measurements, and so on may be different according to each user's genome and health status.

To facilitate the generation of monitoring profiles, the server 104 can store data that defines a taxonomy of different items that can be monitored (e.g., the categories or types of data) and corresponding monitoring program elements (e.g., parameter values, commands, API calls, code snippets, etc.) that cause monitoring of that data item. For example, under the category of physical activity, the server 104 can have different data types such as daily step count, weekly step count, and level of movement in the last hour. A table or other data structure can map each of the different data types to content of a monitoring profile that instructs the corresponding data to be collected. To generate a monitoring profile, the server 104 can identify the types of data to be monitored as discussed above, use the tables to look up the parameter values or other content specified for the identified types of data, and incorporate (e.g., append, combine, etc.) those retrieved parameter values or other content into the monitoring profile.

A monitoring profile can specify many parameters that affect monitoring, including which types of data to collect and how to collect the data. These parameters may include, for example, the type of data to collect (e.g., heart rate, blood pressure, body weight, ambient temperature, ambient sound level, ambient light level, movement amount, location, etc.), a sensor to use in the data collection (e.g., accelerometer, camera, microphone, etc.), a survey instrument to provide (e.g., a PHQ-9 survey to measure depression symptoms, a specific EMA for a particular context), the frequency data collection (e.g., hourly, daily, etc.), conditions or triggers to initiate the data collection, and more. As an example, a first monitoring profile may identify a particular health device 212a (e.g., a smart watch) to perform monitoring, a type of data to collect 212b (e.g., heart rate), and parameters for carrying out the monitoring 212c (e.g., specifying monitoring frequency, such as automatically capturing a measurement every hour).

In some implementations, the first monitoring profile can be a general profile for the health risk detected for the user. The system may have a set of predetermined monitoring profiles used for different health risks or health conditions, e.g., different monitoring profiles respectively used for monitoring risks of heart disease, diabetes, stroke, obesity, etc. The system can select and send the monitoring profile that corresponds to the risk identified for the user. In other implementations, the system can generate a monitoring profile configured to collect the types of data that the system identifies as relevant to the health condition or to genome characteristics of the user that relate to the health condition. In some cases, the system can store monitoring procedures or types of data to collect for different health risks, and then the system combines the monitoring procedures for the health risks to be identified for the user. For example, if the user is determined to have a significant risk of stroke and heart disease, the system can combine the default monitoring procedures for each of these two risks, while avoiding duplication of monitoring for items in common for both. The system then generates a monitoring profile that instructs monitoring according to the combined monitoring scheme.

The monitoring profile can cause an end device to initiate interactions with a user and initiate collection of sensor data by the devices. Examples of sensors that can be used include accelerometers, light sensors, cameras, microphones, inertial measurement units (IMUs), GPS receivers, and compass sensors. Other devices can include other sensors, such as pulse or heart rate sensors, EKG sensors, photoplethysmography sensors, and so on. The monitoring profile can also cause user interactions through presentation of a survey, a notification, a prompt, an EMA, or other user interface or through automatic opening or execution of an application or software module by a user's device.

The system can generate and send monitoring profiles that are configured to cause a device that receives the profile to initiate monitoring and reporting of data to a server, such as the server 104, over a communication network such as the Internet. For example, a monitoring profile can cause a device to collect sensor data on a periodic basis or in response to the occurrence of certain conditions or triggers. The monitoring profile can also cause a user device that receives the monitoring profile to initiate interactions with a user, such as to present a survey or electronic form for receiving information from a user. Information about user interactions, e.g., user input provided in response to a survey, is then reported to a server, such as the server 104. In some implementations, a monitoring profile includes software or configuration data to direct data collection and reporting and interactions with the user. In addition, or as an alternative, the module can include software or configuration data that cause a user device to carry out data collection, reporting, and user interactions as directed by one or more servers, such as the server 104, which may specify different user device behavior and different user interactions at different times.

As discussed further below, the monitoring profile can automatically cause various different changes in the configuration or operation of a user device. These changes include changing device operation to support monitoring, such as: changing parameters that set when the device enters or exits a sleep or idle state; changing which sensors are active (e.g., powered on and active) as well as what frequency they become active and for what duration, as well as which modes of operation of the sensors are used; changing the types of data stored and the precision of measurements; changing which surveys and interactive interfaces are shown to the user, altering or customizing the content presented in those interactions, and the parameters for initiating data-gathering interactions with the user; and so on.

The system provides, to the one or more health monitoring devices, the first monitoring profile (708). The first monitoring profile can instruct a device what to measure for a user (e.g., heart rate, blood pressure, sleep duration) and how to measure these items (e.g., hourly heart rate measurements with a smart watch; daily blood pressure measurements with a blood pressure cuff; sleep duration using passive sensing of movement, sound, and light levels using a smartphone along with a sleep survey each morning).

The system transmits the first monitoring profile from the server 104 to one or more health monitoring devices 102a-102n of the user via the network 106, e.g., as shown in FIG. 1. The monitoring profile can be pushed to devices by the server 104, or devices may have software configured to periodically connect to the server 104 to check for and download updated monitoring profiles for the account of the user. The server 104 can store data that identifies device identifiers or electronic addresses for devices 102a-102n of different users to determine which devices should receive which profiles. In some implementations, when an application to support health monitoring is installed or when a user logs in, the server 104 registers the device as corresponding to the user. In addition, devices 102a-102n can communicate with the server 104 periodically over an API to request updates, provide monitoring data, and receive profiles and other instructions. The user can be logged in to an application on his device, enabling the application to access the user's account, and by virtue of the authentication of the user to the application the server can identify that the application or device is used for that user.

The transmission of a monitoring profile over the network (whether for the first monitoring profile or for subsequent monitoring profiles) can cause one or more remote devices alter their operation to carry out monitoring as directed in the profile. The monitoring profile can be configured to adjust operation of the remote health monitoring devices to set or change sensor parameters used by the remote device to perform sensor measurements using one or more sensors, including changing at least one of a set of sensors used, a type of property or characteristic measured, a timing or schedule at which sensor measurements occur, a frequency of the sensor measurements, durations that the sensors are powered on and active, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements.

The monitoring profile can be configured to adjust operation of the remote devices to set or change data storage parameters used by the remote device to format or store acquired data to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements.

The monitoring profile can be configured to adjust operation of the remote devices to set or change network communication parameters used by the remote device to report acquired data to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data.

The monitoring profile can cause remote devices to perform various changes or configuration actions, often doing so automatically upon receipt of the monitoring profile and without requiring user action. The actions can include: enabling or disabling a sensor of the remote device or a device communicatively coupled to the remote device; setting or changing sensor parameters used by the remote device to conduct sensor measurements using one or more sensors, including changing at least one of a set of sensors used, a type of property measured, a timing of the sensor measurements, a frequency of the sensor measurements, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements; setting or changing data storage parameters used by the remote device to format or store acquired data to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements; setting or changing network communication parameters used by the remote device to report acquired data to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data; setting or changing power usage parameters of the remote device, including changing a device power state or sleep setting of the remote device; altering a user interface of an application installed at the remote device, including changing a set of interactive user input controls presented in the user interface; setting or changing interactive content to be presented by the remote device, the interactive content including at least one survey, prompt, or electronic form; or setting or changing parameters for presenting the interactive content that includes at least one of timing, frequency, format, triggers, or contexts for providing the interactive content.

The system receives epigenetic data including measures for epigenetic factors for the user (710). For example, the epigenetic data can be monitoring results sent to the server 104 over the network 106 by the one or more health monitoring devices 102a-102n for the user. In particular, the epigenetic data may be included in the first health data that the first monitoring profile directed the one or more health monitoring devices 102a-102n for the user to collect.

In some implementations, the first monitoring profile is selected or generated to cause the user's device(s) to collect data for items that the server 104 selected, prior to sending the first monitoring profile, as epigenetic factors corresponding to one or more genome characteristics identified in the user's genome. The epigenetic data can include values (e.g., measurements, sensor data, ratings, scores, indicators, text entered by the user, etc.) that characterize the state of the user for the epigenetic factors that the server 104 had previously selected as relevant to both the user's genome and the health risk being monitored. For example, the server 104 may determine that a user has a particular gene variant that causes increased risk of heart disease, and may select air quality and sugar intake as epigenetic factors to monitor (e.g., because longitudinal data for individuals with the particular gene variant indicates that these items are likely to alter the level of risk for these individuals). The epigenetic data may be air quality measurement values from an air quality sensor and sugar intake results from user surveys, where collection of both of these may be caused by the first monitoring profile. Thus, as a user's device(s) carry out monitoring directed by the first monitoring profile, the first health data that is reported to the server 104 may include measures for the epigenetic factors that the server 104 had identified or predicted to be relevant to the user's genome and the health risk being addressed.

In some implementations, the epigenetic data received may be results of monitoring items that were not identified in advance as epigenetic factors for the user's genome characteristics, but are later identified by the server 104 as epigenetic influences. For example, in the case where the first monitoring profile is a generalized or default monitoring profile for the health risk, the server 104 may obtain a variety of monitoring results, some of which are for epigenetic factors and some are not. Nevertheless, the server 104 can use its records and models to identify and extract from a set of monitoring data items that the server 104 subsequently selects as epigenetic factors for the user. Even from an initial generalized set of monitoring results (e.g., that may not be based on the user's genetic data or personal health risk level), the server 104 can assess the results to recognize and extract the items that the server 104 identifies as epigenetic factors. In other words, the server 104 uses the relationships between genes and epigenetic factors in the processing and analysis of data received about the user to identify which types of monitoring results represent epigenetic factors and to use these in assessing health risks.

As discussed above, the epigenetic data can describe the state of the user (e.g., attributes, measures, indicators, etc.) for various types of epigenetic factors, including environment, behavior, physiology, and more. Epigenetic factors can include environmental characteristics and behavioral characteristics for an individual. Measurement can be performed for a variety of aspects of a user's environment (e.g., air quality, sound levels, light, temperature, water quality, chemical exposure, etc.) and a user's behavior (e.g., sleep, diet, exercise, travel, social activity, etc.). Physiological measures (e.g., blood pressure, heart rate, respiration rate, blood oxygenation level, blood sugar level, weight, body temperature, etc.), demographic factors (e.g., age, sex, etc.), and other health measures (e.g., medications taken, chronic conditions, medical history, etc.) can also be epigenetic factors. Also, as discussed above, epigenetic factors can encompass factors that alter the likelihood of a phenotype (e.g., health outcome or observable result) when in the presence of a certain genome characteristic (e.g., a particular gene variant, SNP, combination of sequences, etc.), even if the factor is not known to alter DNA structure or use by a known method (e.g., methylation).

The system determines that a health change event for the particular health risk has occurred for the user based, at least in part, on the genetic data and the epigenetic data for the user (712). For example, the system receives the first set of health data from the one or more health monitoring devices and determines that the health change event for the particular health risk has occurred for the user based on the genetic data, the epigenetic data, and the first set of health data. The system determines that a change in the health risk that meets a change threshold has occurred. For example, the system determines that the epigenetic data that indicates the epigenetic factor for the user (e.g., behavioral pattern) has caused an increase in the health risk that meets an increase threshold.

A health change event can be a change in the likelihood of the health risk or the actual occurrence of health condition or health state related to the health risk. Examples of determining health change events include the server 104 detecting that the likelihood of the health risk has increased or decreased. In particular, the server 104 can determine that the likelihood has increased or decreased to a predetermined threshold, so that on an absolute scale the likelihood has changed to achieve a particular threshold (e.g., likelihood of at least 20% within a year) or enter a particular range (e.g., enter a range of between 20% to 30%). Similarly, the server can determine when the change in the likelihood has increased or decreased, so that the magnitude of change relative to previous risk meets a threshold (e.g., risk increased by at least 25% compared to the previous week or month, risk decreased by at least 10%).

Other examples of determining health change events include detecting a health outcome or state of health related to the risk. For example, for monitoring diabetes risk, determining that the user's body mass index (BMI) has increased to reach threshold level (e.g., a BMI of 25, 30, 35 or other threshold level). In a similar manner, any of various types of data can cause the serer 104 to detect a change in health that constitutes a health change event. For example, a user reporting a symptom of a disease, the user experiencing a side effect of medication, a user failing to adhere to a medication regimen or therapy regimen, and other events can be identified as health change events that either cause a change to a health risk or are a signal of changed level of risk.

In some cases, determining a health change event may involve detecting an adverse outcome (e.g., onset of an asthma attack, heart attack, weight increasing beyond a threshold level, etc.) or detecting a positive health outcome (e.g., reduced disease symptoms, blood pressure lowered to a healthy range, reduced frequency or severity of anxiety or depression symptoms, a change in user habits to improve nutrition, sleep, exercise, etc.).

In some cases, changes to monitoring results for one or more epigenetic factors lead to the health change event. For example, the user may have a particular SNP that increases risk of DVT, and the system can identify physical activity as an epigenetic factor that has a strong effect on whether users with that SNP experience a DVT. As a result, the system can instruct the user's device to monitor physical activity frequently, e.g., more than for typical patients or even for others with risk of DVT that do not have the particular SNP. The system uses the monitoring results for physical activity (e.g., survey results asking about user movement, GPS location data, accelerometer data, step count, etc.) to calculate how the user's particular level of physical activity increases his risk, given the known presence of the particular SNP. If the system receives monitoring data indicating low physical activity that increases the DVT risk to a level above a threshold (e.g., moving the user from a "moderate risk" category to a "high risk" category), the system may consider the increase in likelihood of DVT as a health change event that the system should respond to. In this situation, a change in the epigenetic data for a user (e.g., change from normal activity to low activity) is the change that causes or indicates the health change event.

Health change events can be determined by the system using various rules, thresholds, or models, which can be different for different health risks. For example, the system can repeatedly generate scores for a health risk as monitoring data is received. The system can repeatedly calculate the likelihood of an adverse health event over time, and determine when updated information about the user causes the likelihood to change in a significant way (e.g., to reach a threshold level or to change by at least a threshold amount).

Health change events can be detected through new information, such as monitoring data that indicates a changed behavior, environmental condition, physiological state, etc. that alters the likelihood for a health risk. Alternatively, health change events may be determined even when monitoring data does not show a change, such as when a user's condition or habits are stable, but the behaviors persisting over an increasing period of time without improvement cause increasing risk. As another example, events predicted or identified for the user can also change the risk. For example, for a person at risk for CVT, when the server 104 detects that the user has an upcoming vaccine appointment, the server 104 may calculate the risk that the new appointment adds, in combination with the user's risk factors from genome characteristics and epigenetic factors, to determine the total risk. If the risk expected with the vaccine is predicted to increase risk by a sufficient amount or to a particular level, then the scheduling of the appointment (or the server 104 obtaining information about the appointment) can be considered a health change event.

The health change event can be detected based on the genetic data and the epigenetic data for the user. Both the genetic data and the epigenetic data are used to determine the risk level for a user. The risk level can be calculated based on the presence of epigenetic factors (e.g., certain environmental or behavioral factors) and their influence when present in combination with specific gene sequences or other features of the genotype. Rather than looking at genetic factors and behavioral and/or environmental factors separately (e.g., as unrelated factors affecting health risk), the system can perform analysis that weights or adjusts risk levels based on the known or predicted interaction of genetic factors and environmental and/or behavioral factors. The system can thus calculate risk levels in a manner that weights or conditions the effect of a measured factor (e.g., environmental, behavioral, physiological) according to the varying level of impact that it has on the health risk for different genome characteristics. For some gene variants, a behavior may have minimal impact on risk while for other gene variants the same behavior may have a much larger impact on the risk. Beyond considering the presence of a gene sequences or the presence of certain behaviors to separately increase risk, the system determines the risk that the behavior has, conditional on the presence of the particular gene sequence of the user.

As an example, for individuals monitored for risk of stroke, increased blood pressure may be known to be a contributing factor generally (e.g., regardless of the user's genome). Nevertheless, the system can interpret a moderately high blood pressure level (e.g., 130/90) differently depending on the genome characteristics of the individual. For some sets of genetic features, this may represent a low risk (e.g., +5% compared to an average blood pressure level). When certain genetic features are present, however, the system can determine that the same moderately high blood pressure may present a higher risk (e.g., +50%). As discussed above, the actual risk level may be determined from statistical analysis or machine learning analysis of data sets showing heath data, genetic data, and health outcomes for many individuals, enabling the system to determine how, when certain genetic features are present, certain environmental and behavioral attributes (or values or ranges of those attributes) have an outsized impact on risk, and so can be identified as epigenetic factors of particular relevance to specific genes, gene variants, SNPs, etc. Machine learning models can be very effective at considering the complex interrelationships of many variables. Nevertheless, the system may also use a statistical approach, such as to aggregate a combination of identified markers of risk, both genetic and epigenetic, to calculate a risk level for a user. For example, the system may identify three gene sequences present for a user that increase risk of heart disease by differing amounts (e.g., +5%, +9%, and +2%) compared to a base level of risk, as well as epigenetic factors that increase or lessen those risks (e.g., poor air quality experienced by the user doubling the increase in risk of the first gene sequence (e.g., from +5% to +10%), and a high exercise level present for the user counteracting the risk of the third gene sequence entirely). By aggregating these different risk level modifiers, the system can determine an overall level of risk for the user.

In response to detecting the health change event, the system determines, for the particular health risk, a second monitoring profile for the user that causes the one or more health monitoring devices to monitor the user for a second set of health data according to the second monitoring profile (714). The second monitoring profile is different from the first monitoring profile, in a manner that causes health monitoring devices to perform different monitoring than the first monitoring profile. For example, when the health change event is an increase in likelihood for a health risk, the second monitoring profile can increase a frequency of monitoring or add an additional item (e.g., type or category of data to be collected) to be monitored. As another example, when the health change event is a decrease in likelihood for a health risk, then the second monitoring profile can decrease a frequency of monitoring or remove item from the set of items to be monitored. This conserves resources of the end devices (e.g., battery power, processor utilization, network bandwidth, and data storage space). Overall, these features allow the system to automatically make changes to incrementally increase or decrease the granularity, precision, and comprehensiveness of monitoring commensurate with the risk level for the user. Users who have high or increasing risks are thus provided high or increasing levels of monitoring, while those who have low or decreasing risks have low or decreasing levels of monitoring.

As discussed above, the monitoring is adjusted in a manner that is more accurate and safer than prior approaches, because the risk level on which the monitoring is based takes into account the interaction of genome characteristics and known or inferred epigenetic factors. In other words, the risk level (and consequently the monitoring level determined from the risk level) is made more accurate than in prior approaches by the system setting the risk level based on the user's genome characteristics, but modulating the risk presented by the genetic features based on the values of epigenetic factors for those genetic features. In particular, the system can set and adjust monitoring to capture monitoring data for selected sets of epigenetic factors that are known or predicted to have strong influence (e.g., at least a minimum threshold) on risk in the specific context of specific genetic features being present.

In some implementations, the system adjusts the first monitoring profile to generate a second monitoring profile that causes the one or more health monitoring devices to monitor the user for a set of health data at a frequency that is greater than the frequency specified in the first monitoring profile (e.g., every hour rather than twice a day). In some implementations, the system generates the monitoring profile to cause the one or more health monitoring devices to monitor the user to collect (1) first types of health data specified in the first monitoring profile, and (2) one or more additional types of health data not in the first types of health data. The system can store data indicating a hierarchy or taxonomy of measurement techniques and parameter values for different categories of information to be gathered. For example, there can be different levels of monitoring exercise that show increasing granularity or intensity of monitoring, such as basic monitoring amount (e.g., daily step count), a second monitoring level (e.g., accelerometer data and daily step count), a third monitoring level (e.g., accelerometer data and hourly step counts and a daily exercise survey for the user), etc. The system can store tables that map different types or categories of health risks, or different risk levels, to different monitoring levels. As a result, a user that has a high risk can be assigned monitoring for relevant health data types at a high monitoring level, while a user that has a moderate risk can be assigned monitoring for the health data types at a lower monitoring level.

Using the techniques discussed above for step 706, the server 104 can generate or select the second monitoring profile based on the genetic data and epigenetic data for the user. For example, the genetic characteristics of the user can influence which environmental and behavioral characteristics are monitored, as different characteristics can have different levels of influence (e.g., ability to cause epigenetic change) for different genetic characteristics. Similarly, the server 104 can use the measured values for an epigenetic factor already measured to adjust monitoring of that factor. For example, even if blood pressure is already monitored, the system may determine that results indicating a high blood pressure measurement justify more frequent monitoring of this factor, since values in some ranges may have stronger or more negative effect on development of a phenotype that others.

The system provides the second monitoring profile to the one or more health monitoring devices (716). The server 104 can transmit the second monitoring profile to the one or more health monitoring devices over the network 106, as discussed for step 708. The second monitoring profile can include content of the type discussed above for steps 706 and 708. The second monitoring profile can cause any of the various types of changes to configuration and/or operation of the devices that receive the second monitoring profile, as discussed above, to cause devices to change the monitoring that they perform.

After the second monitoring profile is provided, the server 104 receives, from the one or more health monitoring devices, a second set of health data generated through the monitoring performed by the health monitoring devices according to the second monitoring profile. The server 104 can use the received data to further re-calculate the likelihood of the health risk and consequently adjust monitoring further. In this manner, the system can dynamically adjust the type and level of monitoring dynamically based on the changes to the risk level that the system calculates.

The systems discussed herein used in any of the examples and implementations discussed above can include a variety of information from a variety of sources. Data can be collected for categories representing a variety of individual, community, or public health conditions and behaviors. This data can include attributes that are biological, physical or physiological, mental, emotional, environmental, or social. The collected data can include biological attributes, such as genetic makeup, genomics, family history, sensory abilities (e.g., ability to see, perception of light and dark, perception of color, extent of ability to smell, ability to touch and sensitivity, ability to hear and sensitivity, etc.). These may reflect biological factors that a person cannot control. The collected data can include physical or physiological attributes, e.g., weight, muscle mass, heart rate, sleep, nutrition, exercise, lung capacity, brain activity, etc. Some physical attributes may result from the impact of lifestyle choices or things that a person can control. The collected data can include mental attributes, such as interpretation of brain related signals, indications of chemical imbalances, education levels, results of mental tests, etc. The collected data can include emotional attributes, such as interpretation of selfreported data, or classified audio or video related data that suggests individual responses to stimuli. The collected data can include environmental data, such as location data, air quality, audible noise, visual noise, temperature, humidity, movement (and potentially effects of movement such as motion sickness, etc. The collected data can include social attributes, such as whether a subject is socially engaged, exhibits social avoidance, experiences the impact of acceptance or responsiveness emotionally, and so on.

The data collected and used by the system to monitor health and determine a user's status with respect to epigenetic factors (e.g., to use in adjusting monitoring, assessing health risks, assessing responses to treatments, training models, identifying and characterizing epigenetic factors with respect to genetic features and/or health risks and health conditions, as epigenetic factors, etc.) can include various other types of data including:

Lab and diagnostic data (e.g., assay data, blood test results, tissue sample results, endocrine panel results);

Omics data (e.g., data relating to genomics, proteomics, pharmacogenomics, epigenomics, metabolomics, biointeractomics, interactomics, lifeomics, calciomics, chemogenomics, foodomics, lipidomics, metabolomics, bionomics, econogenomics, connectomics, culturomics, cytogenomics, fermentanomics, fluxomics, metagenomics, metabonomics, metallomics, O-glcNAcomics, glycomics, glycoproteomics, glycosaminoglycanomics, immunoproteomics, ionomics, materiomics, metalloproteomics, metaproteogenomics, metaproteomics, metatranscriptomics, metronomics, microbiomics, microeconomics, microgenomics, microproteomics, miRomics, mitogenomics, mitoproteomics, mobilomics, morphomics, nanoproteomics, neuroeconomics, neurogenomics, neuromics, neuropeptidomics, neuroproteomics, nitroproteomics, nutrigenomics, nutrimetabonomics, oncogenomics, orthoproteomics, pangenomics, peptidomics, pharmacoeconomics, pharmacometabolomics, pharmacoproteomics, pharmaeconomics, phenomics, phospholipidomics, phosphoproteomics, phylogenomics, phylotranscriptomics, phytomics, postgenomics, proteogenomics, proteomics, radiogenomics, rehabilomics, retrophylogenomics, secretomics, surfaceomics, surfomics, toxicogenomics, toxicometabolomics, toxicoproteomics, transcriptomics, vaccinomics, variomics, venomics, antivenomics, agrigenomics, aquaphotomics);

Biologically sampled data (e.g., data describing blood, urine, saliva, breath sample, skin scrape, hormone levels, ketones, glucose levels, breathalyzer, DNA, perspiration, and other biological samples and derived data);

Cardiac-related biodata (e.g., data from ECG/EKG monitors, heart rate monitors, blood pressure monitors);

Respiratory-related biodata (e.g. data from spirometers, pulse oximeters);

Neurological-related biodata (e.g. data from EEG monitors);

Behavior data (e.g. movement patterns, gait, social avoidance);

Drug data (e.g., prescription information, pharmacological data);

Substance use data (e.g., alcohol, medication, insulin, recreational drugs, tobacco);

Sleep data (e.g., motion data, heart rate data, body temperature, perspiration, breathing data, ambient light, ambient sound, ambient temperature);

Exercise data (e.g. performance data, distance covered, activity, VO2 Max),

Physical activity data (e.g., step counts, heart rate, flights climbed, altitude, other data from fitness trackers);

Mood data (e.g., happiness, depression, PHQ9, BMIS data and other scales/reporting mechanism);

Positioning and location data (e.g., GPS data, gyroscope, altimeter, accelerometer, linear acceleration, received signal strength indicator from nearby emitters such as WiFi access points, Bluetooth sensors and sensor networks and Cellular towers);

Environmental data (e.g., air quality data, ozone data, weather data, water-quality data, audible decibel levels, interpreting measured audio data, measuring luminance lux, interpreting measured light wavelengths, measuring temperature and gases or particles—such as formaldehyde (Molecular Formula: $H_2CO$ or $CH_2O$); alcohol vapor (Molecular Formula: hydroxyl group-OH, e.g., Isopropyl$C_3H_8O$ or $C_3H_7OH$, as well as Ethanol: $C_2H_6O$ or $C_2H_5OH$); benzene ($C_6H_6$); Hexane ($C_6H_{14}$); Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CHCH_3$ or $C_4H_{10}$ or $(CHC_4H_{10})_2$ $CHCH_3$); propane (Molecular Formula: $CH_3CH_2CH_3$ or $C_3H_8$); natural coal or town gas which could include of methane or natural gas (Molecular Formula: $CH_4$); carbon dioxide (Molecular Formula: $CO_2$); hydrogen (Molecular Formula: $H_2$); carbon monoxide or possibly smoke (Molecular Formula: CO); and oxygen (Molecular Formula: $O_2$) in the environment surrounding an individual inside and outside the contextual location of the potential subjects such as home, office, and including vehicle data—such as speed, location, amount of time driving, mood while driving, environmental data in the car).

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a standalone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A computer-implemented method, comprising:
for each user of a first plurality of users:
generating a health profile for the user based on genetic data of the user and (ii) health data of the user resulting from monitoring over a time period, the health data of the user being received from one or more health monitoring devices of the user over a time period;
determining, based on the health profile of the user, a particular health risk for the user;
determining, for the particular health risk, a first monitoring profile for the user that causes the one or more health monitoring devices to monitor the user to obtain one or more first types of health data according to the first monitoring profile, wherein the first monitoring profile includes first instructions that cause at least one of the one or more health monitoring devices to collect the one or more first types of health data;
providing the first monitoring profile to the one or more health monitoring devices of the user;
receiving, from the one or more health monitoring devices of the user, epigenetic data including measures of one or more epigenetic factors for the user;
determining whether a health change event for the particular health risk has occurred for the user based, at least in part, on the genetic data of the user and the epigenetic data of the user, wherein the health change event is a change of the particular health risk of the user from a first level to a second level;
for each user of a second plurality of users for which the health change event has been determined to have occurred, wherein the second plurality of users is a subset of the first plurality of users:
determining, for the particular health risk determined for the user, a second monitoring profile for the user that causes the one or more health monitoring devices of the user to monitor the user to obtain one or more second types of health data according to the second monitoring profile, wherein the second monitoring profile is different from the first monitoring profile and includes second instructions that cause at least one of the one or more health monitoring devices of the user to collect the one or more second types of health data, wherein:
the second instructions are executable instructions that are configured to be executed by the one or more health monitoring devices of the user to automatically initiate monitoring of the user to obtain the one or more second types of health data, and that, upon execution of the second instructions by the one or more health monitoring devices of the user, direct the one or more health monitoring devices of the user to change an amount of monitoring performed by the one or more health monitoring devices according to the change in the particular health risk for the user; and
providing, to the one or more health monitoring devices of the user, the second monitoring profile to cause the one or more health monitoring devices of the user to monitor the user to obtain the one or more second types of health data, wherein the one or more second types of health data are different from the one or more first types of health data.

2. The computer-implemented method of claim 1, further comprising:
receiving, from the one or more health monitoring devices, a first set of health data for the first types of health data; and
determining whether the health change event for the particular health risk has occurred for the user based, at least in part, on the genetic data and the epigenetic data for the user comprises determining that the health change event for the particular health risk has occurred for the user based on the genetic data, the epigenetic data, and the first set of health data.

3. The computer-implemented method of claim 1, further comprising receiving, from the one or more health monitoring devices, a second set of health data for the second types of health data monitored by the health monitoring devices according to the second monitoring profile.

4. The computer-implemented method of claim 1, wherein determining a particular health risk for the user comprises:
- comparing the health profile of the user with data specifying genetic and health risk factors; and
- identifying a particular health risk for the user based on the comparison.

5. The computer-implemented method of claim 1, wherein determining a particular health risk for the user comprises:
- receiving a set of health profiles of other users;
- comparing the health profile of the user with the set of health profiles of other users; and
- identifying a particular health risk for the user based on the comparison.

6. The computer-implemented method of claim 1, wherein determining a particular health risk for the user comprises:
- providing data from the health profile as input to a trained machine learning model trained to determine a health risk based on the input; and
- receiving, from the trained machine learning model, data identifying the particular health risk.

7. The computer-implemented method of claim 1, wherein determining whether the health change event for the particular health risk has occurred for the user comprises:
- determining, based, at least in part, on the genetic data and the epigenetic data for the user, that a change in the health risk that meets a change threshold has occurred.

8. The computer-implemented method of claim 7, wherein:
- determining, based, at least in part, on the genetic data and the epigenetic data for the user, that a change in the health risk that meets a change threshold has occurred comprises determining that the epigenetic data that indicates the epigenetic factor for the user has caused an increase in the health risk that meets an increase threshold; and
- determining, for the particular health risk, the second monitoring profile for the user comprises adjusting the first monitoring profile to cause the one or more health monitoring devices to monitor the user for a set of health data at an increased frequency from a frequency specified in the first monitoring profile.

9. The computer-implemented method of claim 7, wherein:
- determining, based, at least in part, on the genetic data and the epigenetic data for the user, that a change in the health risk that meets a change threshold has occurred comprises determining that the epigenetic data that indicates the epigenetic factor for the user has caused an increase in the health risk that meets an increase threshold; and
- determining, for the particular health risk, the second monitoring profile for the user comprises generating the monitoring profile to cause the one or more health monitoring devices to monitor the user for the one or more first types of health data and one or more additional types of health data not in the one or more first types of health data, wherein the one or more first types of health data and the one or more additional types of health data not in the first types of health data comprise the one or more second types of health data.

10. The method of claim 1, wherein the second monitoring profile changes the amount of monitoring by the one or more health monitoring devices according to the change in the particular health risk for the user by one or more of (i) adding a health monitoring device to collect a type of health data not included in the one or more first types of health data or (ii) removing a health monitoring device to end collection of a type of health data included in the one or more first types of health data.

11. The method of claim 1, wherein the second monitoring profile is configured to cause the one or more second types of health data to be collected using a type of interaction or technique different from the type of interaction or technique used to obtain the one or more first types of health data for the user.

12. The method of claim 1, wherein (i) one of the one or more first types of health data or the one or more second types of health data is collected using user input to the one or more health monitoring devices of the user, and (ii) the other of the one or more first types of health data or the one or more second types of health data is collected using a sensor of the one or more health monitoring devices of the user.

13. The method of claim 1, wherein the first instructions of the first monitoring profile are configured to cause the one or more first types of health data to be collected by a first device, sensor, or survey; and
- wherein the second instructions of the second monitoring profile are configured to cause the one or more second types of health data to be collected by a second device, sensor, or survey, wherein the second device, sensor, or survey is different from the first device, sensor, or survey.

14. The method of claim 1, wherein the second monitoring profile changing the amount of monitoring by the one or more health monitoring devices according to the change in the particular health risk for the user includes changing a frequency of collecting health data for the user.

15. A system comprising one or more computers and one or more storage devices storing instructions that, when executed by the one or more computers, cause the one or more computers to perform operations comprising:
- for each user of a first plurality of users:
  - generating a health profile for the user based on (i) genetic data of the user and (ii) health data of the user resulting from monitoring over a time period, the health data of the user being received from one or more health monitoring devices of the user over a time period;
  - determining, based on the health profile of the user, a particular health risk for the user;
  - determining, for the particular health risk, a first monitoring profile for the user that causes the one or more health monitoring devices to monitor the user to obtain one or more first types of health data according to the first monitoring profile, wherein the first monitoring profile includes first instructions that cause at least one of the one or more health monitoring devices to collect the one or more first types of health data;
  - providing the first monitoring profile to the one or more health monitoring devices of the user;
  - receiving, from the one or more health monitoring devices of the user, epigenetic data including measures of one or more epigenetic factors for the user;
  - determining whether a health change event for the particular health risk has occurred for the user based, at least in part, on the genetic data of the user and the epigenetic data of the user, wherein the health change event is a change of the particular health risk of the user from a first level to a second level;

for each user of a second plurality of users for which the health change event has been determined to have occurred, wherein the second plurality of users is a subset of the first plurality of users:
    determining, for the particular health risk determined for the user, a second monitoring profile for the user that causes the one or more health monitoring devices of the user to monitor the user to obtain one or more second types of health data according to the second monitoring profile, wherein the second monitoring profile is different from the first monitoring profile and includes second instructions that cause at least one of the one or more health monitoring devices of the user to collect the one or more second types of health data, wherein:
        the second instructions are executable instructions that are configured to be executed by the one or more health monitoring devices of the user to automatically initiate monitoring of the user to obtain the one or more second types of health data, and that, upon execution of the second instructions by the one or more health monitoring devices of the user, direct the one or more health monitoring devices of the user to change an amount of monitoring performed by the one or more health monitoring devices according to the change in the particular health risk for the user; and
    providing, to the one or more health monitoring devices of the user, the second monitoring profile to cause the one or more health monitoring devices of the user to monitor the user to obtain the one or more second types of health data, wherein the one or more second types of health data are different from the one or more first types of health data.

16. The system of claim 15, the operations further comprising:
    receiving, from the one or more health monitoring devices, a first set of health data for the first types of health data; and
    determining whether the health change event for the particular health risk has occurred for the user based, at least in part, on the genetic data and the epigenetic data for the user comprises determining that the health change event for the particular health risk has occurred for the user based on the genetic data, the epigenetic data, and the first set of health data.

17. The system of claim 15, the operations further comprising receiving, from the one or more health monitoring devices, a second set of health data for the second types of health data monitored by the health monitoring devices according to the second monitoring profile.

18. The system of claim 15, wherein determining a particular health risk for the user comprises:
    comparing the health profile of the user with data specifying genetic and health risk factors; and
    identifying a particular health risk for the user based on the comparison.

19. The system of claim 15, wherein determining a particular health risk for the user comprises:
    receiving a set of health profiles of other users;
    comparing the health profile of the user with health profiles in the set of health profiles of other users; and
    identifying a particular health risk for the user based on the comparison.

20. The system of claim 15, wherein determining a particular health risk for the user comprises:
    providing data from the health profile as input to a trained machine learning model that has been trained to determine a health risk based on the input; and
    receiving, from the trained machine learning model, data identifying the particular health risk.

21. The system of claim 15, wherein determining whether the health change event for the particular health risk has occurred for the user comprises:
    determining, based, at least in part, on the genetic data and the epigenetic data for the user, that a change in the health risk that meets a change threshold has occurred.

22. The system of claim 21, wherein:
    determining, based, at least in part, on the genetic data and the epigenetic data for the user, that a change in the health risk that meets a change threshold has occurred comprises determining that the epigenetic data that indicates the epigenetic factor for the user has caused an increase in the health risk that meets an increase threshold; and
    determining, for the particular health risk, the second monitoring profile for the user comprises adjusting the first monitoring profile to cause the one or more health monitoring devices to monitor the user for a set of health data at an increased frequency from a frequency specified in the first monitoring profile.

23. One or more non-transitory computer storage media storing instructions that, when executed by one or more computers, cause the one or more computers to perform operations comprising:
    for each user of a first plurality of users:
        generating a health profile for the user based on (i) genetic data of the user and (ii) health data of the user resulting from monitoring over a time period, the health data of the user being received from one or more health monitoring devices of the user over a time period;
        determining, based on the health profile of the user, a particular health risk for the user;
        determining, for the particular health risk, a first monitoring profile for the user that causes the one or more health monitoring devices to monitor the user to obtain one or more first types of health data according to the first monitoring profile, wherein the first monitoring profile includes first instructions that cause at least one of the one or more health monitoring devices to collect the one or more first types of health data;
        providing the first monitoring profile to the one or more health monitoring devices of the user;
        receiving, from the one or more health monitoring devices of the user, epigenetic data including measures of one or more epigenetic factors for the user;
        determining whether a health change event for the particular health risk has occurred for the user based, at least in part, on the genetic data of the user and the epigenetic data of the user, wherein the health change event is a change of the particular health risk of the user from a first level to a second level;
    for each user of a second plurality of users for which the health change event has been determined to have occurred, wherein the second plurality of users is a subset of the first plurality of users:
        determining, for the particular health risk determined for the user, a second monitoring profile for the user that causes the one or more health monitoring devices of the user to monitor the user to obtain one or more second types of health data according to the second monitoring profile, wherein the second monitoring profile is different from the first monitoring profile and includes second instructions that cause at least one of the one or more health monitoring devices of the user to collect the one or more second types of health data, wherein:

the second instructions are executable instructions that are configured to be executed by the one or more health monitoring devices of the user to automatically initiate monitoring of the user to obtain the one or more second types of health data, and that, upon execution of the second instructions by the one or more health monitoring devices of the user, direct the one or more health monitoring devices of the user to change an amount of monitoring performed by the one or more health monitoring devices according to the change in the particular health risk for the user; and providing, to the one or more health monitoring devices of the user, the second monitoring profile to cause the one or more health monitoring devices of the user to monitor the user to obtain the one or more second types of health data, wherein the one or more second types of health data are different from the one or more first types of health data.

24. The one or more non-transitory computer storage media of claim 23, further comprising:
based on the genetic data for the user, identifying, by the one or more computers, a genome characteristic that increases a likelihood of the particular health risk for the user; and
selecting, by the one or more computers, a set of epigenetic factors for the user based on the identified genome characteristic, wherein the epigenetic factors comprise environmental, behavioral, or physiological attributes that are determined to or are predicted to affect a likelihood or severity of the health risk for individuals having the genetic characteristic;
wherein determining the first monitoring profile comprises generating or selecting the first monitoring profile to include monitoring of the set of epigenetic factors selected for the user;
wherein providing the first monitoring profile causes the one or more health monitoring devices to initiate measurements for the set of epigenetic factors using sensors of the one or more health monitoring devices or using surveys presented by the one or more health monitoring devices; and
wherein receiving the epigenetic data comprises receiving data indicating measures of each of the epigenetic factors in the set of epigenetic factors that were selected for the user.

* * * * *